US008609402B2

(12) United States Patent
Havenga et al.

(10) Patent No.: US 8,609,402 B2
(45) Date of Patent: *Dec. 17, 2013

(54) MULTIVALENT VACCINES COMPRISING RECOMBINANT VIRAL VECTORS

(75) Inventors: Menzo Jans Emco Havenga, Alphen aan den Rijn (NL); Ronald Vogels, Linschoten (NL); Jerald C. Sadoff, Bethesda, MD (US); David Hone, Bethesda, MD (US); Yasir Abdul Wahid Skeiky, Silver Spring, MD (US); Katarina Radoševic, Rotterdam (NL)

(73) Assignees: Aeras Global TB Vaccine Foundation, Rockville, MD (US); Crucell Holland B.V, Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/134,206

(22) Filed: May 31, 2011

(65) Prior Publication Data

US 2011/0256166 A1  Oct. 20, 2011

Related U.S. Application Data

(63) Continuation of application No. 11/667,975, filed as application No. PCT/EP2005/055984 on Nov. 15, 2005, now Pat. No. 8,012,467.

(60) Provisional application No. 60/651,113, filed on Feb. 8, 2005, provisional application No. 60/628,253, filed on Nov. 16, 2004.

(30) Foreign Application Priority Data

Nov. 25, 2004  (EP) .................................. 04106074

(51) Int. Cl.
| C12N 15/00 | (2006.01) |
| C12N 15/09 | (2006.01) |
| C12N 15/48 | (2006.01) |
| C12N 15/52 | (2006.01) |
| C12N 15/867 | (2006.01) |

(52) U.S. Cl.
USPC ..... 435/320.1; 435/69.3; 435/93.2; 435/93.6; 424/93.2; 536/23.72; 536/24.1; 536/23.4

(58) Field of Classification Search
None
See application file for complete search history.

(56) References Cited

U.S. PATENT DOCUMENTS

| 5,916,558 A | 6/1999 | Content et al. |
| 5,955,077 A | 9/1999 | Andersen et al. |

(Continued)

FOREIGN PATENT DOCUMENTS

| EP | 1449922 A2 | 8/2004 |
| EP | 0 792 358 B1 | 6/2005 |

(Continued)

OTHER PUBLICATIONS

Baldwin et al., Evaluation of New Vaccines in the Mouse and Guinea Pig Model of Tuberculosis, Infection and Immunity, Jun. 1998, pp. 2951-2959, vol. 66, No. 6.

(Continued)

Primary Examiner — Maria Marvich
(74) Attorney, Agent, or Firm — TraskBritt, P.C.

(57) ABSTRACT

The invention relates to vaccines comprising recombinant vectors, such as recombinant adenoviruses. The vectors comprise heterologous nucleic acids encoding for at least two antigens from one or more tuberculosis-causing bacilli. Also described is the use of specific protease recognition sites linking antigens through which the encoded antigens are separated upon cleavage. After cleavage, the antigens contribute to the immune response in a separate manner. The recombinant vectors may comprise a nucleic acid encoding the protease cleaving the linkers and separating the antigens. Further described is the use of genetic adjuvants encoded by the recombinant vectors, wherein such genetic adjuvants may also be cleaved through the presence of the cleavable linkers and the specific protease.

18 Claims, 35 Drawing Sheets

(56) References Cited

U.S. PATENT DOCUMENTS

| | | | |
|---|---|---|---|
| 6,083,716 A | 7/2000 | Wilson et al. | |
| 6,290,969 B1 | 9/2001 | Reed et al. | |
| 6,338,852 B1 | 1/2002 | Reed et al. | |
| 6,350,456 B1 | 2/2002 | Reed et al. | |
| 6,384,018 B1 | 5/2002 | Content et al. | |
| 6,458,366 B1 | 10/2002 | Reed et al. | |
| 6,465,633 B1 | 10/2002 | Skeiky | |
| 6,544,522 B1 | 4/2003 | Skeiky et al. | |
| 6,555,653 B2 | 4/2003 | Alderson et al. | |
| 6,592,877 B1 | 7/2003 | Reed et al. | |
| 6,596,281 B1 | 7/2003 | Gennaro et al. | |
| 6,599,510 B1 | 7/2003 | Horwitz et al. | |
| 6,613,881 B1 | 9/2003 | Alderson et al. | |
| 6,627,198 B2 | 9/2003 | Reed et al. | |
| 6,641,814 B1 | 11/2003 | Andersen et al. | |
| 7,666,656 B2 * | 2/2010 | Sun et al. | 435/253.1 |
| 8,012,467 B2 * | 9/2011 | Havenga et al. | 424/93.2 |
| 8,202,723 B2 * | 6/2012 | Havenga et al. | 435/320.1 |
| 2002/0150592 A1 | 10/2002 | Horwitz | |
| 2002/0176867 A1 | 11/2002 | Andersen et al. | |
| 2003/0138459 A1 | 7/2003 | Wang | |
| 2003/0219458 A1 | 11/2003 | Wang | |
| 2004/0057963 A1 | 3/2004 | Andersen et al. | |
| 2004/0185064 A9 | 9/2004 | Wang | |
| 2004/0265336 A9 | 12/2004 | Wang | |
| 2006/0216272 A1 | 9/2006 | Emini et al. | |
| 2006/0286128 A1 | 12/2006 | Agger | |
| 2007/0065912 A1 | 3/2007 | Carson et al. | |

FOREIGN PATENT DOCUMENTS

| | | |
|---|---|---|
| WO | WO 92/14823 A1 | 9/1992 |
| WO | WO 95/01441 A1 | 1/1995 |
| WO | WO 95/14713 A2 | 6/1995 |
| WO | WO 96/15241 A2 | 5/1996 |
| WO | WO 96/37219 A1 | 11/1996 |
| WO | WO 97/09428 A2 | 3/1997 |
| WO | WO 97/09429 A2 | 3/1997 |
| WO | WO 98/16645 A2 | 4/1998 |
| WO | WO 98/16646 A2 | 4/1998 |
| WO | WO 98/31388 A1 | 7/1998 |
| WO | WO 98/44119 A1 | 10/1998 |
| WO | WO 98/53075 A2 | 11/1998 |
| WO | WO 98/53076 A2 | 11/1998 |
| WO | WO 99/04005 | 1/1999 |
| WO | WO 99/045005 A1 | 1/1999 |
| WO | WO 99/24577 A1 | 5/1999 |
| WO | WO 99/42076 A3 | 8/1999 |
| WO | WO 99/42118 A2 | 8/1999 |
| WO | WO 99/51748 A3 | 10/1999 |
| WO | WO 00/21983 A2 | 4/2000 |
| WO | WO 00/39301 A3 | 7/2000 |
| WO | WO 00/55194 A3 | 9/2000 |
| WO | WO 00/70071 A1 | 11/2000 |
| WO | WO 01/04151 A2 | 1/2001 |
| WO | WO 01/23421 A3 | 4/2001 |
| WO | WO 01/24820 A1 | 4/2001 |
| WO | WO 01/25401 A2 | 4/2001 |
| WO | WO 01/62893 A2 | 8/2001 |
| WO | WO 01/70991 A1 | 9/2001 |
| WO | WO 01/79274 A2 | 10/2001 |
| WO | WO 01/98460 A2 | 12/2001 |
| WO | WO 02/40665 A2 | 5/2002 |
| WO | WO 02/092132 A | 11/2002 |
| WO | WO 02/098360 A2 | 12/2002 |
| WO | WO 03/000851 A2 | 1/2003 |
| WO | WO 03/046124 A2 | 6/2003 |
| WO | WO 03/070187 A2 | 8/2003 |
| WO | WO 03/104467 A1 | 12/2003 |
| WO | WO 2004/001032 A2 | 12/2003 |
| WO | WO 2004/006952 A2 | 1/2004 |
| WO | WO 2004/037294 A2 | 5/2004 |
| WO | WO 2004/083418 A1 | 9/2004 |
| WO | WO 2005/017149 A1 | 2/2005 |
| WO | WO 2005/061534 A | 7/2005 |
| WO | WO 2006/053871 A2 | 5/2006 |

OTHER PUBLICATIONS

Kamath et al., Differential Protective Efficacy of DNA Vaccines Expressing Secreted Proteins of *Mycobacterium tuberculosis*, Infection and Immunity, Apr. 1999, pp. 1702-1707, vol. 67, No. 4.

Skjot et al., Comparative Evaluation of Low-Molecular-Mass Proteins from *Mycobacterium tuberculosis* Identifies Members of the ESAT-6 Family as Immunodominant T-Cell Antigens, Infection and Immunity, Jan. 2000, pp. 214-220, vol. 68, No. 1.

Xing, The Hunt for New Tuberculosis Vaccines: Anti-TB Immunity and Rational Design of Vaccines, Current Pharmaceutical Design, 2001, pp. 1015-1037, vol. 7.

Skjot et al., Epitope Mapping of the Immunodominant Antigen TB10.4 and the Two Homologous Proteins TB10.3 and TB12.9, Which Constitute a Subfamily of the esat-6 Gene Family, Oct. 2002, pp. 5446-5453, vol. 70, No. 10.

Tian et al., Protection of Mice with a Divalent Tuberculosis DNA Vaccine Encoding Antigens Ag85B and MPT64, Acta Biochimica et Biophysica Sinica, 2004, pp. 269-276, vol. 36, No. 4.

Wang et al., Single Mucosal, but Not Parenteral, Immunization with Recombinant Adenoviral-Based Vaccine Provides Potent Protection from Pulmonary Tuberculosis, The Journal of Immunology, 2004, pp. 6357-6365, vol. 173.

* cited by examiner

Stimulation: none
A. CD4
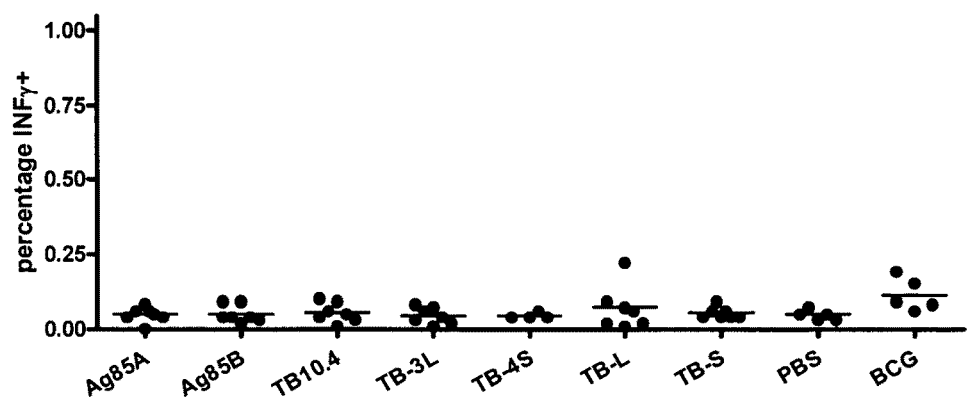
B. CD8
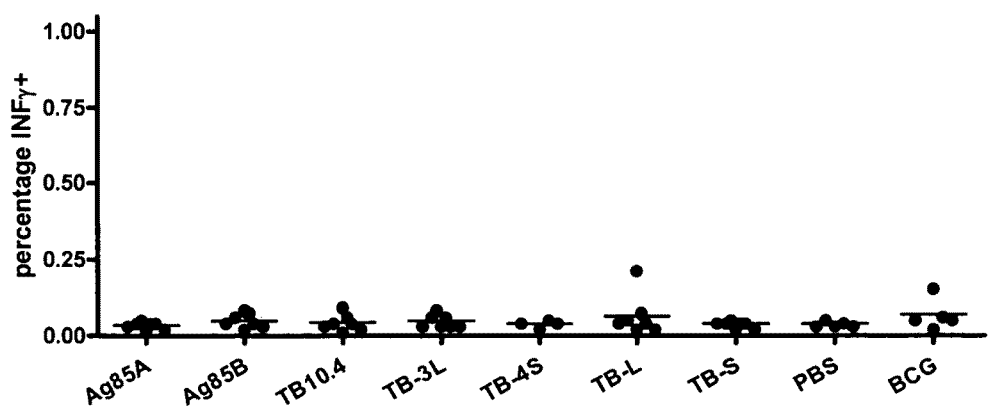
FIG. 12

Stimulation: Ag85A peptides
A. CD4
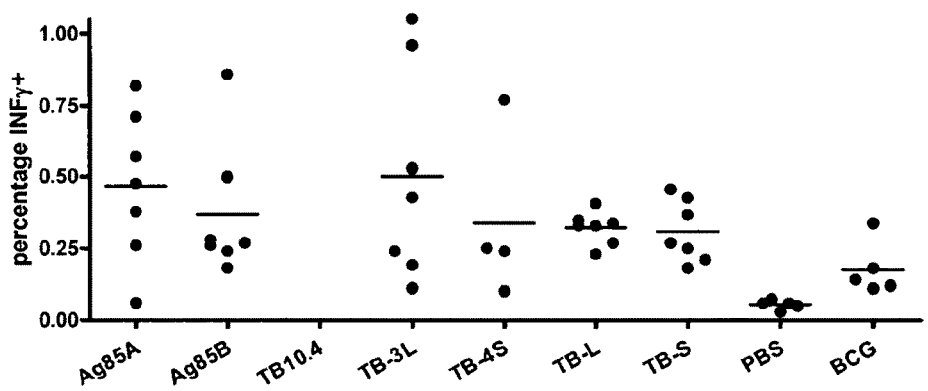
B. CD8
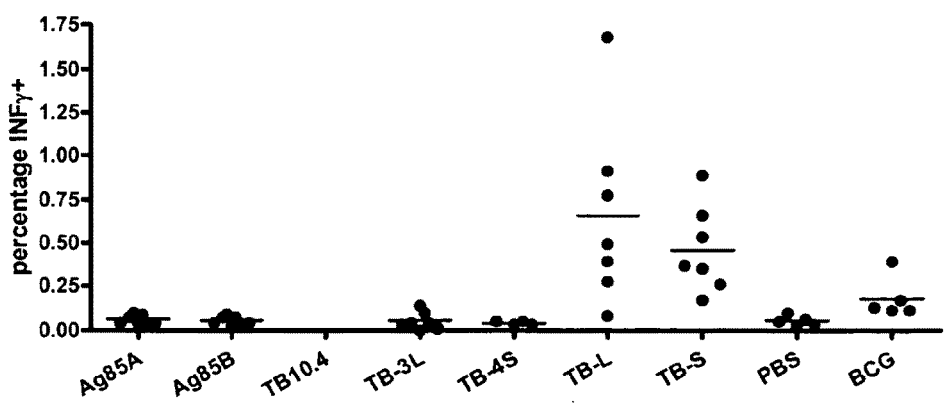
FIG. 13

Stimulation: Ag85B peptides
A. CD4
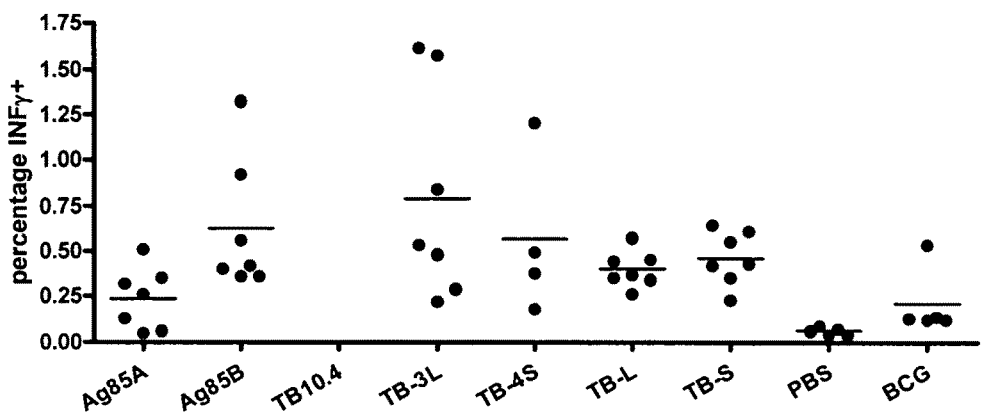
B. CD8
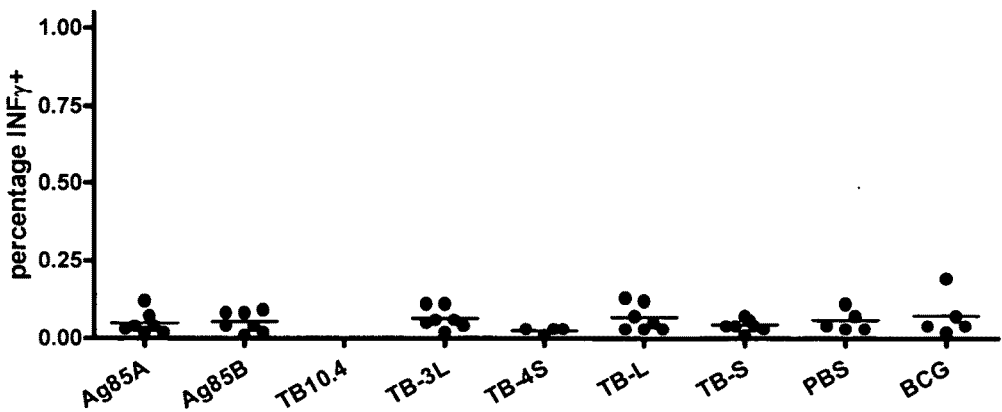
FIG. 14

Stimulation: 10.4 peptides
A. CD4
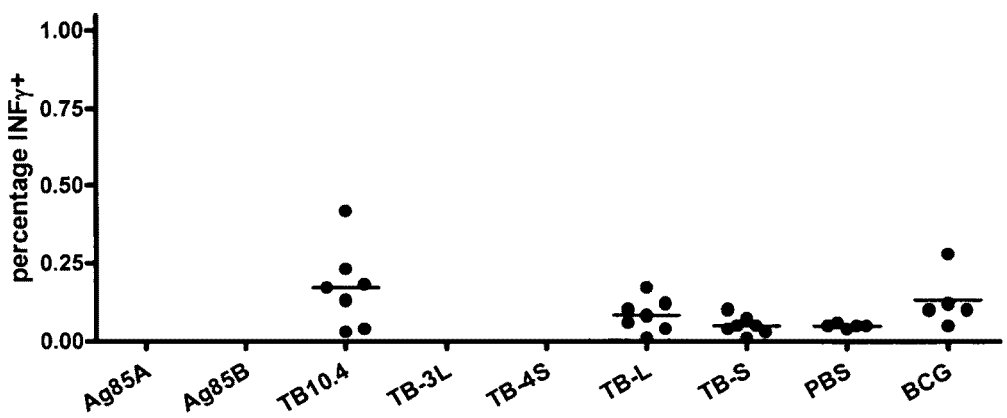
B. CD8
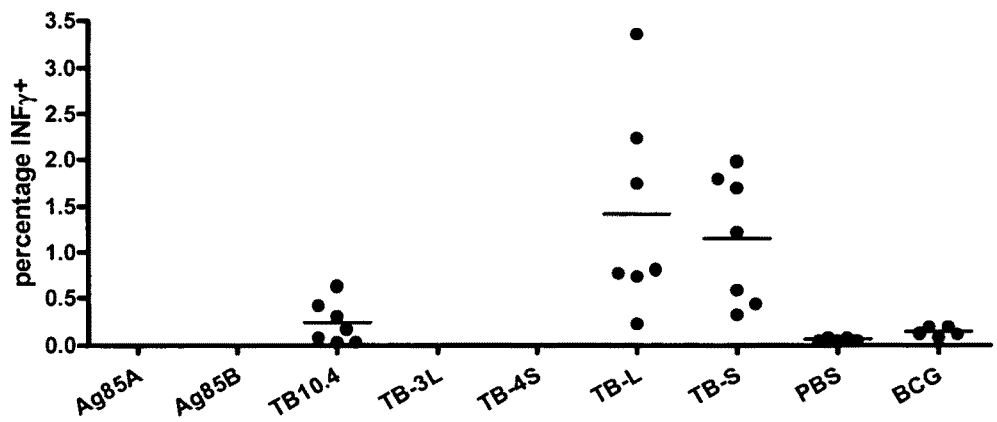
FIG. 15

Overview CD4 and CD8 responses (triple inserts)
A.
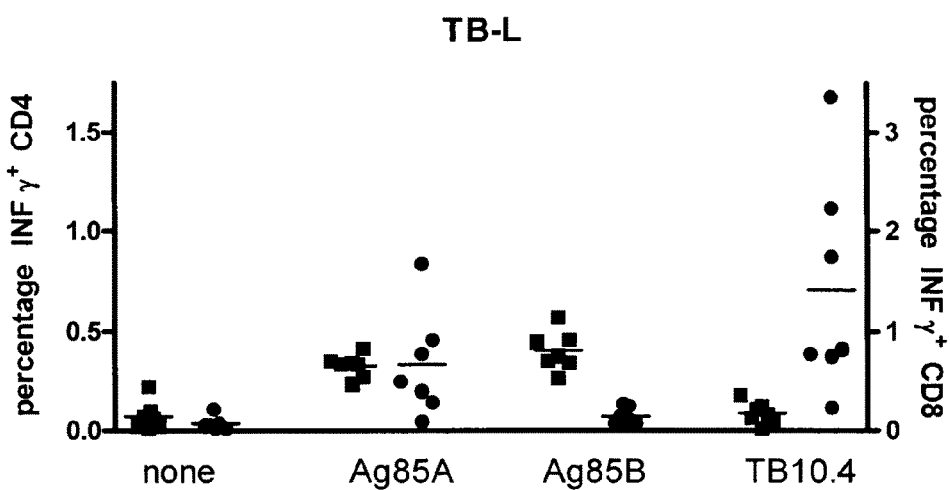
B.
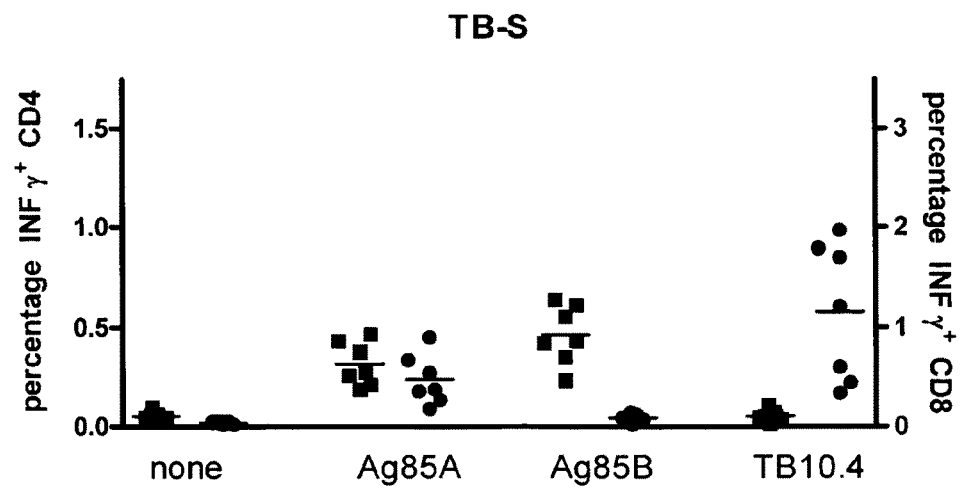
FIG. 16

Ag85B stimulation, CD4

Ag85B stimulation, CD8

TB-LM DNA sequence (SEQ ID NO:3)

```
aagcttgcca ccatgctggc catgaccatg gagcaccggg accggcccct ggtgagagtg    60
atcctgacca acaccggcag ccaccccgtg aagcagcgga gcgtgtacat caccgccctg   120
ctggacagcg gagccgacat caccatcatc agcgaggagg actggcccac cgactggccc   180
gtggtggaca ccgcaaccc ccagatccac ggcatcggcg aggcatccc catgcggaag    240
agccgggaca tgatcgagct gggcgtgatc aacgggacg cagcctgga gcggccctg     300
ctgctgttcc ccgccgtggc catggtgcgg ggcagcatcc tgggccggga ctgcctgcag   360
ggcctgggcc tgcggctgac caacctgggc agcagcggcc cctggcctgc ccccgagccc   420
cctgccgtga gcctggctat gacaatggaa cacagagaca gaccctggt gttcagcaga    480
cccggcctgc ccgtggagta cctgcaggtg cccagcccca gcatgggccg ggacatcaaa   540
gtgcagttcc agagcggcgg agccaacagc cctgccctgt acctgctgga cggcctgcgg   600
gcccaggacg acttcagcgg ctgggacatc aacacccccg ccttcgagtg gtacgaccag   660
agcggcctga gcgtggtgat gcccgtgggc ggccagagca gcttctacag cgactggtat   720
cagcccgcct gcggcaaggc cggctgccag acctacaagt gggagacctt cctgaccagc   780
gagctgcccg gctggctgca ggccaaccgg cacgtgaagc ccaccggcag cgccgtggtg   840
ggcctgagca tggccgccag cagcgccctg accctggcca tctaccaccc ccagcagttc   900
gtgtacgccg gagccatgag cggcctgctg gaccccagcc aggccatggg ccccaccctg    960
atcggcctgg ccatgggcga cgccggaggc tacaaggcca gcgacatgtg gggccccaag   1020
gaggacccc cctggcagcg gaacgacccc ctgctgaacg tgggcaagct gatcgccaac   1080
aacacccgcg tgtgggtgta ctgcggcaac ggcaagccca gcgacctggg cggcaacaac   1140
ctgccgcca gttcctgga gggcttcgtg cggaccagca acatcaagtt ccaggacgcc    1200
tacaacgccg gaggcggcca acggcgtg ttcgacttcc ccgacagcgg cacccacagc    1260
tgggagtact ggggagccca gctgaacgcc atgaagcccg acctgcagcg ggccctgggc   1320
gccacccca acaccggccc tgccccccag ggcgctcccc cagcaagag caagaagggc    1380
ggagccgccg ctatgagcag cgccatccag cccctggtga tggccgtggt gaaccgggag   1440
cgggacggcc agaccggctt cagccggcct ggcctgctg tggaatatct gcaggtgccc   1500
tcccctcta tgggccgcga tattaaagtg cagtttcagt ccggcggcaa caatagccca   1560
gccgtgtatc tgctggatgg gctgagagcc caggacgatt acaatggctg ggatatcaat   1620
acacctgcct ttgagtggta ctatcagtct ggcctgtcca tcgtgatgcc tgtgggagga   1680
cagtccagct tctactctga ctggtactct cctgcctgtg gcaaagccgg atgtcagaca   1740
tacaaatggg aaacatttct gacctccgag ctgcccagt ggctgagcgc caacagagcc   1800
gtgaagccta caggctctgc cgccatcggc ctgtctatgg ccggcagctc tgccatgatc   1860
ctggccgcct atcaccctca gcagtttatc tacgccggca cctgtctgc cctgctggat   1920
ccctctcagg gcatgggccc ttctctgatt ggactggcta ggggacgc tggcggatac    1980
aaggccgccg atatgtgggg acccagcagc gaccctgcct gggagagaaa cgaccccacc   2040
cagcagatcc ccaaactggt ggccaacaat accaggctgt gggtgtactg tggaaatggc   2100
acccccaacg agctgggagg cgccaacatc cccgccgagt tctggagaa cttcgtgaga   2160
agcagcaacc tgaagtttca ggatgccat aatgccgccg gaggccacaa tgccgtgttc   2220
aattttcccc ccaacggcac ccactcttgg aatattggg gcgctcagct gaatgctatg   2280
aagggggacc tgcagagcag cctgggagcc ggccctccca gcaagtctaa gaaggaggc   2340
gccgctgcca tgtctagcgc cattcagcct ctggtgatgg ctgtggtgaa cagagaggg   2400
gacgggcaga ctggcatgag ccagatcatg tacaactacc ccgccatgct gggccacgcc   2460
ggcgacatgg ccggctacgc cggcacactg cagagcctgg gcgccgagat cgccgtggag   2520
caggccgccc tgcagtctgc ctggcagggc gacaccggca tcacctacca ggcctggcag   2580
gcccagtgga accaggccat ggaggacctg gtgcgggcct accacgccat gagcagcacc   2640
cacgaggcca acaccatggc catgatggcc cgggacaccg ccgaggccgc caagtgggc   2700
ggcagcaaga aaaccgagca gaagctgatc tccgaggagg acctgtgata atctaga      2757
```

FIG. 19

TB-SM DNA sequence (SEQ ID NO:4)

```
aagcttgcca ccatgttcag cagacccggc ctgccgtgg  agtacctgca ggtgcccagc    60
cccagcatgg gccgggacat caaagtgcag ttccagagcg gcggagccaa cagccctgcc   120
ctgtacctgc tggacggcct gcgggcccag gacgacttca gcggctggga catcaacacc   180
cccgccttcg agtggtacga ccagagcggc ctgagcgtgg tgatgcccgt gggcggccag   240
agcagcttct acagcgactg gtatcagccc gcctgcggca aggccggctg ccagacctac   300
aagtgggaga ccttcctgac cagcgagctg cccggctggc tgcaggccaa ccggcacgtg   360
aagcccaccg gcagcgccgt ggtgggcctg agcatggccg ccagcagcgc cctgaccctg   420
gccatctacc accccagca gttcgtgtac gccggagcca tgagcggcct gctggacccc   480
agccaggcca tgggccccac cctgatcggc ctggccatgg gcgacgccgg aggctacaag   540
gccagcgaca tgtggggccc caaggaggac cccgcctggc agcggaacga ccccctgctg   600
aacgtgggca agctgatcgc caacaacacc cgcgtgtggg tgtactgcgg caacggcaag   660
cccagcgacc tgggcggcaa caacctgccc gccaagttcc tggagggctt cgtgcggacc   720
agcaacatca agttccagga cgcctacaac gccggaggcg gccacaacgg cgtgttcgac   780
ttccccgaca gcggcaccca cagctgggag tactgggag  cccagctgaa cgccatgaag   840
cccgacctgc agcgggccct gggcgccacc cccaacaccg gccctgcccc caggggcgct   900
ttcagccggc ctggcctgcc tgtggaatat ctgcaggtgc cctcccctc  tatgggccgc   960
gatattaaag tgcagtttca gtccggcggc aacaatagcc agccgtgta  tctgctggat  1020
gggctgagag cccaggacga ttacaatggc tgggatatca atacacctgc ctttgagtgg  1080
tactatcagt ctggcctgtc catcgtgatg cctgtgggag acagtccag  cttctactct  1140
gactggtact ctcctgcctg tggcaaagcc ggatgtcaga catacaaatg gaaacattt   1200
ctgacctccg agctgcccca gtggctgagc gccaacagag ccgtgaagcc tacaggctct  1260
gccgccatcg gcctgtctat ggccggcagc tctgccatga tcctggccgc ctataccct   1320
cagcagttta tctacgccgg cagcctgtct gccctgctgg atccctctca gggcatgggc  1380
ccttctctga ttggactggc tatgggggac gctggcggat acaaggccgc cgatatgtgg  1440
ggacccagca gcgaccctgc ctgggagaga acgaccccca cccagcagat ccccaaactg  1500
gtggccaaca ataccaggct gtgggtgtac tgtggaaatg gcaccccaa  cgagctggga  1560
ggcgccaaca tccccgccga gtttctggag aacttcgtga gaagcagcaa cctgaagttt  1620
caggatgcct ataatgccgc cggaggccac aatgccgtgt tcaatttccc ccccaacggc  1680
acccactctt gggaatattg gggcgctcag ctgaatgcta tgaaggggga cctgcagagc  1740
agcctggag  ccggcatgag ccagatcatg tacaactacc ccgccatgct gggccacgcc  1800
ggcgacatgg ccggctacgc cggcacactg cagagcctgg gcgccagat  cgccgtggag  1860
caggccgccc tgcagtctgc ctggcagggc gacaccggca tcacctacca ggcctggcag  1920
gcccagtgga accaggccat ggaggacctg gtgcgggcct accacgccat gagcagcacc  1980
cacgaggcca acaccatggc catgatggcc cggacaccg  ccgaggccgc caagtggggc  2040
ggcagcaaga aaaccgagca gaagctgatc tccgaggagg acctgtgata atctaga     2097
```

FIG. 20

TB-FLM DNA sequence (SEQ ID NO:5)

```
aagcttgcca ccatgttcag cagacccggc ctgcccgtgg agtacctgca ggtgcccagc    60
cccagcatgg gccgggacat caaagtgcag ttccagagcg gcggagccaa cagccctgcc   120
ctgtacctgc tggacggcct gcgggcccag gacgacttca gcggctggga catcaacacc   180
cccgccttcg agtggtacga ccagagcggc ctgagcgtgg tgatgcccgt gggcggccag   240
agcagcttct acagcgactg gtatcagccc gcctgcggca aggccggctg ccagacctac   300
aagtgggaga ccttcctgac cagcgagctg cccggctggc tgcaggccaa ccggcacgtg   360
aagcccaccg gcagcgccgt ggtgggcctg agcatggccc cagcagcgc cctgaccctg   420
gccatctacc accccagca gttcgtgtac gccggagcca tgagcggcct gctggacccc   480
agccaggcca tgggccccac cctgatcggc ctggccatgg gcgacgccgg aggctacaag   540
gccagcgaca tgtgggccc caaggaggac cccgcctggc agcggaacga ccccctgctg   600
aacgtgggca agctgatcgc caacaacacc cgcgtgtggg tgtactgcgg caacggcaag   660
cccagcgacc tgggcggcaa caacctgccc gccaagttcc tggagggctt cgtgcggacc   720
agcaacatca agttccagga cgcctacaac gccggaggcg ccacaacgg cgtgttcgac   780
ttccccgaca gcggcaccca cagctgggag tactggggag cccagctgaa cgccatgaag   840
cccgacctgc agcgggcc t gggcgccacc cccaacaccg gccctgcccc ccagggcgct   900
ggcaccggcg gcagcggcgg caccggcagc ggcacaggcg gctctgtgtt cagccggcct   960
ggcctgcctg tggaatatct gcaggtgccc tccccctcta tgggccgcga tattaaagtg  1020
cagtttcagt ccggcggcaa caatagccca gccgtgtatc tgctggatgg gctgagagcc  1080
caggacgatt acaatggctg ggatatcaat acacctgcct ttgagtggta ctatcagtct  1140
ggcctgtcca tcgtgatgcc tgtgggagga cagtccagct tctactctga ctggtactct  1200
cctgcctgtg gcaaagccgg atgtcagaca tacaaatggg aaacatttct gacctccgag  1260
ctgccccagt ggctgagcgc caacagagcc gtgaagccta caggctctgc cgccatcggc  1320
ctgtctatgg ccggcagctc tgccatgatc ctggccgcct atcaccctca gcagtttatc  1380
tacgccggca gcctgtctgc cctgctggat ccctctcagg catgggccc ttctctgatt  1440
ggactggcta tggggacgc tggcggatac aaggccgccg atatgtgggg acccagcagc  1500
gaccctgcct gggagagaaa cgaccccacc cagcagatcc ccaaactggt ggccaacaat  1560
accaggctgt gggtgtactg tggaaatggc accccccaacg agctgggagg cgccaacatc  1620
cccgccgagt ttctggagaa cttcgtgaga agcagcaacc tgaagtttca ggatgcctat  1680
aatgccgccg gaggccacaa tgccgtgttc aatttccccc caacggcac ccactcttgg  1740
gaatattggg gcgctcagct gaatgctatg aaggggggacc tgcagagcag cctgggagcc  1800
ggcggcaccg gaggctctgg cggcacaggc tctggcaccg gcggatctgt gatgagccag  1860
atcatgtaca actaccccgc catgctgggc cacgccggcg acatggccgg ctacgccggc  1920
acactgcaga gcctgggcgc cgagatcgcc gtggagcagg ccgccctgca gtctgcctgg  1980
cagggcgaca ccggcatcac ctaccaggcc tggcaggccc agtggaacca ggccatggag  2040
gacctggtgc gggcctacca cgccatgagc agcacccacg aggccaacac catggccatg  2100
atggcccggg acaccgccga ggccgccaag tggggcggca gcaagaaaac cgagcagaag  2160
ctgatctccg aggaggacct gtgataatct aga                                2193
```

FIG. 21

TB-LM protein sequence (SEQ ID NO:6)

```
MLAMTMEHRD RPLVRVILTN TGSHPVKQRS VYITALLDSG ADITIISEED WPTDWPVVDT    60
ANPQIHGIGG GIPMRKSRDM IELGVINRDG SLERPLLLFP AVAMVRGSIL GRDCLQGLGL   120
RLTNLGSSGP WPAPEPPAVS LAMTMEHRDR PLVFSRPGLP VEYLQVPSPS MGRDIKVQFQ   180
SGGANSPALY LLDGLRAQDD FSGWDINTPA FEWYDQSGLS VVMPVGGQSS FYSDWYQPAC   240
GKAGCQTYKW ETFLTSELPG WLQANRHVKP TGSAVVGLSM AASSALTLAI YHPQQFVYAG   300
AMSGLLDPSQ AMGPTLIGLA MGDAGGYKAS DMWGPKEDPA WQRNDPLLNV GKLIANNTRV   360
WVYCGNGKPS DLGGNNLPAK FLEGFVRTSN IKFQDAYNAG GGHNGVFDFP DSGTHSWEYW   420
GAQLNAMKPD LQRALGATPN TGPAPQGAPP SKSKKGGAAA MSSAIQPLVM AVVNRERDGQ   480
TGFSRPGLPV EYLQVPSPSM GRDIKVQFQS GGNNSPAVYL LDGLRAQDDY NGWDINTPAF   540
EWYYQSGLSI VMPVGGQSSF YSDWYSPACG KAGCQTYKWE TFLTSELPQW LSANRAVKPT   600
GSAAIGLSMA GSSAMILAAY HPQQFIYAGS LSALLDPSQG MGPSLIGLAM GDAGGYKAAD   660
MWGPSSDPAW ERNDPTQQIP KLVANNTRLW VYCGNGTPNE LGGANIPAEF LENFVRSSNL   720
KFQDAYNAAG GHNAVFNFPP NGTHSWEYWG AQLNAMKGDL QSSLGAGPPS KSKKGGAAAM   780
SSAIQPLVMA VVNRERDGQT GMSQIMYNYP AMLGHAGDMA GYAGTLQSLG AEIAVEQAAL   840
QSAWQGDTGI TYQAWQAQWN QAMEDLVRAY HAMSSTHEAN TMAMMARDTA EAAKWGGSKK   900
TEQKLISEED L                                                       911
```

FIG. 22

TB-SM protein sequence (SEQ ID NO:7)

```
MFSRPGLPVE YLQVPSPSMG RDIKVQFQSG GANSPALYLL DGLRAQDDFS GWDINTPAFE    60
WYDQSGLSVV MPVGGQSSFY SDWYQPACGK AGCQTYKWET FLTSELPGWL QANRHVKPTG   120
SAVVGLSMAA SSALTLAIYH PQQFVYAGAM SGLLDPSQAM GPTLIGLAMG DAGGYKASDM   180
WGPKEDPAWQ RNDPLLNVGK LIANNTRVWV YCGNGKPSDL GGNNLPAKFL EGFVRTSNIK   240
FQDAYNAGGG HNGVFDFPDS GTHSWEYWGA QLNAMKPDLQ RALGATPNTG PAPQGAFSRP   300
GLPVEYLQVP SPSMGRDIKV QFQSGGNNSP AVYLLDGLRA QDDYNGWDIN TPAFEWYYQS   360
GLSIVMPVGG QSSFYSDWYS PACGKAGCQT YKWETFLTSE LPQWLSANRA VKPTGSAAIG   420
LSMAGSSAMI LAAYHPQQFI YAGSLSALLD PSQGMGPSLI GLAMGDAGGY KAADMWGPSS   480
DPAWERNDPT QQIPKLVANN TRLWVYCGNG TPNELGGANI PAEFLENFVR SSNLKFQDAY   540
NAAGGHNAVF NFPPNGTHSW EYWGAQLNAM KGDLQSSLGA GMSQIMYNYP AMLGHAGDMA   600
GYAGTLQSLG AEIAVEQAAL QSAWQGDTGI TYQAWQAQWN QAMEDLVRAY HAMSSTHEAN   660
TMAMMARDTA EAAKWGGSKK TEQKLISEED L                                  691
```

FIG. 23

TB-FLM protein sequence (SEQ ID NO:8)

```
MFSRPGLPVE YLQVPSPSMG RDIKVQFQSG GANSPALYLL DGLRAQDDFS GWDINTPAFE    60
WYDQSGLSVV MPVGGQSSFY SDWYQPACGK AGCQTYKWET FLTSELPGWL QANRHVKPTG   120
SAVVGLSMAA SSALTLAIYH PQQFVYAGAM SGLLDPSQAM GPTLIGLAMG DAGGYKASDM   180
WGPKEDPAWQ RNDPLLNVGK LIANNTRVWV YCGNGKPSDL GGNNLPAKFL EGFVRTSNIK   240
FQDAYNAGGG HNGVFDFPDS GTHSWEYWGA QLNAMKPDLQ RALGATPNTG PAPQGAGTGG   300
SGGTGSGTGG SVFSRPGLPV EYLQVPSPSM GRDIKVQFQS GGNNSPAVYL LDGLRAQDDY   360
NGWDINTPAF EWYYQSGLSI VMPVGGQSSF YSDWYSPACG KAGCQTYKWE TFLTSELPQW   420
LSANRAVKPT GSAAIGLSMA GSSAMILAAY HPQQFIYAGS LSALLDPSQG MGPSLIGLAM   480
GDAGGYKAAD MWGPSSDPAW ERNDPTQQIP KLVANNTRLW VYCGNGTPNE LGGANIPAEF   540
LENFVRSSNL KFQDAYNAAG GHNAVFNFPP NGTHSWEYWG AQLNAMKGDL QSSLGAGGTG   600
GSGGTGSGTG GSVMSQIMYN YPAMLGHAGD MAGYAGTLQS LGAEIAVEQA ALQSAWQGDT   660
GITYQAWQAQ WNQAMEDLVR AYHAMSSTHE ANTMAMMARD TAEAAKWGGS KKTEQKLISE   720
EDL                                                                723
```

FIG. 24

MULTIVALENT VACCINES COMPRISING RECOMBINANT VIRAL VECTORS

CROSS-REFERENCE TO RELATED APPLICATIONS

This application is a continuation of U.S. patent application Ser. No. 11/667,975, filed May 16, 2007, now U.S. Pat. No. 8,012,467 (Sep. 6, 2011), which application is a national phase entry of PCT International Patent Application No. PCT/EP2005/055984, filed on Nov. 15, 2005, designating the United States of America, and published, in English, as PCT International Pubin. No. WO 2006/053871 A2 on May 26, 2006, which itself claims the benefit under Article 8 of the PCT to European Patent Appln. EP 04106074.0, filed Nov. 25, 2004, and under 35 U.S.C. §119(e) of U.S. Provisional Patent Appln. 60/651,113, filed Feb. 8, 2005, and U.S. Provisional Patent Application 60/628,253, filed Nov. 16, 2004, the entire disclosure of each of which is hereby incorporated herein by this reference.

JOINT RESEARCH AGREEMENT

The claimed invention was made by or on behalf of the following parties to a joint research agreement: Crucell Holland B.V. and Aeras Global TB Vaccine Foundation. The agreement was in effect on or before the date the claimed invention was made, and the claimed invention was made as a result of activities undertaken within the scope of the agreement.

FIELD OF THE INVENTION

The invention relates to the field of recombinant DNA and viral vector vaccines. Specifically, it relates to recombinant DNA and viral vectors harboring nucleic acids encoding multiple antigens and/or adjuvants.

BACKGROUND OF THE INVENTION

Tuberculosis (TB) has been a major worldwide threat to human health for several thousands of years. TB caused by *Mycobacterium tuberculosis* is an infectious disease of the lung caused by infection through exposure to air-borne *M. tuberculosis* bacilli. These bacilli are extremely infectious and it has been estimated that currently approximately one-third of the world population (2 billion people) are infected. It has been further estimated that TB kills over 2 million people worldwide on an annual basis. Only 5 to 10% of the immunocompetent humans are susceptible to TB, and over 85% of them will develop the disease exclusively in the lungs, while HIV-infected humans may also develop systemic diseases that will more easily lead to death.

Approximately 90% of *M. tuberculosis*-infected humans will not develop the disease. However, in these latently infected individuals, the bacilli can survive for many years and become reactivated, for instance, in the case of a weakened immune system, such as after an HIV infection. Due to the latent nature, infected individuals generally have to be treated by administration of several antibiotics for up to 12 months. This is not a very attractive treatment in general and due to costs and the possible occurrence of multi-drug resistance, it is also not a very effective treatment in most developing countries.

One relatively successful TB vaccine has been developed: the bacilli Calmette-Guerin (BCG) vaccine was generated in the early years of the twentieth century and was first given to individuals in 1921. The BCG vaccine is an attenuated strain of bacteria based on a *Mycobacterium bovis* isolate obtained from a cow. It is a relatively safe vaccine, which is easily, and rather inexpensively, produced. In the year 2000, BCG vaccination covered 86% of the world population. However, the vaccine appears to not be extremely effective for adult pulmonary TB and many regions in developing countries still have very high rates of TB, despite the BCG vaccine programs. It has been estimated that BCG vaccine prevents only 5% of all vaccine-preventable deaths by TB (Kaufmann, 2000).

Due to the rather low protection rate of the BCG vaccine in general and due to the specific protection with respect to childhood and disseminated TB, more efforts were put in the development of new, more broadly applicable, vaccines against TB, which were based on other systems and knowledge acquired in other fields, such as vaccination against other tropical infectious diseases and HIV (review by Wang and Xing, 2002).

Different approaches were taken to develop new TB vaccines, ranging from subunit vaccines and DNA vaccines to modified *mycobacterium* strains. Moreover, recombinant viral-based vaccines were also generated, enabling the transfer of *M. tuberculosis* antigens to antigen-presenting cells through gene delivery vehicles, such as Modified Vaccinia Ankara (MVA) vectors and replication-defective adenovirus vectors.

Naked DNA vaccines against TB have been described in WO 96/15241 (see also EP 0792358), whereas many reports describe the use of numerous antigens from *Mycobacterium tuberculosis* in either recombinant or purified form for their application in vaccines: WO 95/01441, WO 95/14713, WO 96/37219, U.S. Pat. No. 6,599,510, WO 98/31388, WO 98/44119, WO 99/04005, WO 99/24577, WO 00/21983, WO 01/04151, WO 01/79274, WO 2004/006952, US 2002/0150592. The use of fusion proteins comprising different TB antigens has also been suggested. See WO 98/44119, EP 0972045 and EP 1449922, disclosing the use of a fusion polypeptide between ESAT-6 and MPT59 (MPT59 is also referred to as Ag85B or the 85B antigen).

Despite all these and other efforts in generating a vaccine against tuberculosis that ensures both a strong cellular and a strong humoral response, as well as a long-lasting high protection rate, no such vaccine is yet available.

SUMMARY OF THE INVENTION

Described are recombinant viral vectors, preferably replication-defective adenoviruses, more preferably recombinant human adenovirus serotypes Ad11, Ad24, Ad26, Ad34, Ad35, Ad48, Ad49, and Ad50, wherein the viral vectors comprise a heterologous nucleic acid sequence encoding for (fusion) polypeptides of at least two antigens from one or more tuberculosis-causing bacilli. The encoded antigens may be directly linked, i.e., forming one single polypeptide. In one typical embodiment, the antigens are present in a precursor polyprotein, in the sense that they are connected via a linker sequence recognized by a specific protease that is co-expressed. The heterologous nucleic acid may comprise the gene encoding the protease. The fusion proteins with the direct linkages elicit desired immune responses due to the antigens present in the fusion product, whereas the proteins comprising the protease sites are cleaved into separate discrete antigen forms, each contributing to the desired immune response. The protease is preferably linked to the antigens by a protease-recognition site recognized by a cellular protease. Both set-ups provide additional or even synergistic effects in comparison to vaccination or therapy in which viral vectors are used that comprise only a single transgene-encoding unit. More generally, also described are viral vectors comprising a heterologous nucleic acid sequence encoding multiple antigens separated by protease-specific cleavage sites. It is to be understood that such antigens may be from a wide variety of sources including, but not limited to, infectious agents such as viruses, bacteria and parasites, and are thus, according to this aspect of the invention, not limited to antigens from tuberculosis-causing bacilli. The antigens from *Tuberculosis mycobacterium* serve as non-limiting examples of how such multivalent viral vector vaccines are generated and how, upon entry into the host cell, the antigens are separated, and they are able to contribute to the immune response.

Also described is the use of genetic adjuvants that are co-expressed from the viral vector. These adjuvants are encoded by a nucleic acid, which is part of the heterologous nucleic acid sequence introduced into the viral vector genome. The adjuvant is expressed together with the specific antigen(s) and is thereby able to stimulate the immune response towards the antigen(s). Clearly, the sequence encoding the adjuvant may be linked directly to the sequence encoding the antigen(s), but is preferably separated from the sequence encoding one or more antigen(s) by the linker sequence encoding the protease recognition site. In the latter case, the adjuvant is present in the host separately from the antigen(s) and is able to provide its immune-stimulatory effects along with the antigen(s).

BRIEF DESCRIPTION OF THE DRAWINGS

FIG. 12: Percentages of antigen-specific splenocytes that stain positive for interferon-gamma production (IFNγ+) upon stimulation with no peptide (Panel A: CD4+ cells; Panel B: CD8+ cells).
FIG. 13: Percentages of antigen-specific splenocytes that stain positive for interferon-gamma production (IFNγ+) upon stimulation with a pool of peptides relevant for the Ag85A antigen (Panel A: CD4+ cells; Panel B: CD8+ cells).
FIG. 14: Percentages of antigen-specific splenocytes that stain positive for interferon-gamma production (IFNγ+) upon stimulation with a pool of peptides relevant for the Ag85B antigen (Panel A: CD4+ cells; Panel B: CD8+ cells).
FIG. 15: Percentages of antigen-specific splenocytes that stain positive for interferon-gamma production (IFNγ+) upon stimulation with a pool of peptides relevant for the TB10.4 antigen (Panel A: CD4+ cells; Panel B: CD8+ cells).
FIG. 16: Overview of percentages of CD4+ and CD8+ splenocytes that stain positive in ICN, in sera obtained from mice injected with the triple inserts TB-L (Panel A) and TB-S (Panel B).
FIG. 19: Nucleotide sequence of TB-LM.
FIG. 20: Nucleotide sequence of TB-SM.
FIG. 21: Nucleotide sequence of TB-FLM.
FIG. 22: Amino acid sequence of TB-LM.
FIG. 23: Amino acid sequence of TB-SM.
FIG. 24: Amino acid sequence of TB-FLM.

DETAILED DESCRIPTION

Figure 1:
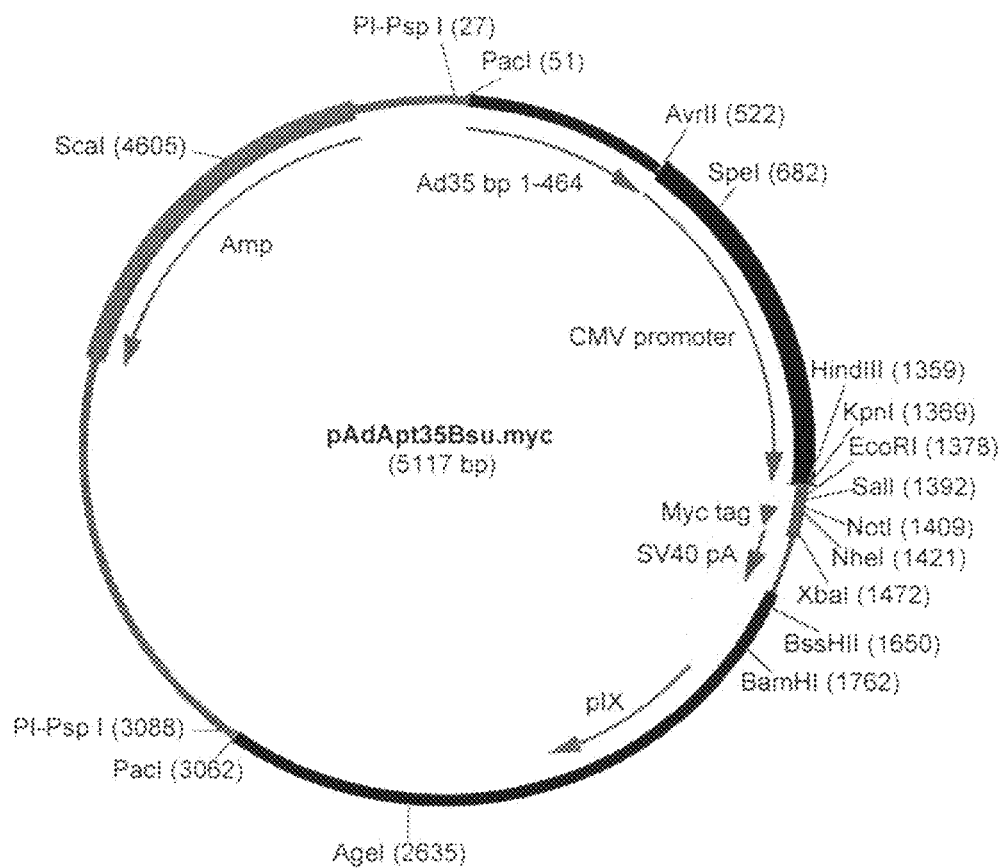
FIG. 1: Map of pAdApt35Bsu.myc.

Described are multivalent vaccines comprising a recombinant viral vector. A typical viral vector is a recombinant Adenovirus (Ad) vector. The recombinant adenoviral vector hereof comprises a heterologous nucleic acid sequence encoding at least two different antigens. The antigens may be within a single polypeptide. These determinants may be either antigens from viral, bacterial and parasitic pathogens, or host antigens, such as, but not limited to, autoimmune antigens or tumor antigens. In a typical embodiment, the antigens are from tuberculosis (TB)-causing bacilli, more preferably from *Mycobacterium tuberculosis, M. africanum* or *M. bovis* or from a combination thereof. The antigens may be the full-length native protein, chimeric fusions between the antigen and a host protein or mimetic, a fragment or fragments thereof or of an antigen that originates from the pathogen, or other mutants that still elicit a desired immune response. Genes encoding TB antigens that may typically be used in the viral vectors of the invention include, but are not limited to: Ag85A (MPT44), Ag85B (MPT59), Ag85C (MPT45), TB10.4 (CFP7), ESAT-6, CFP7A, CFP7B, CFP8A, CFP8B, CFP9, CFP10, CFP10A, CFP11, CFP16, CFP17, CFP19, CFP19A, CFP19B, CFP20, CFP21, CFP22, CFP22A, CFP23, CFP23A, CFP23B, CFP25, CFP25A, CFP26 (MPT51) CFP27, CFP28, CFP29, CFP30A, CFP30B, CWP32, CFP50, MPT63, MTC28, LHP, MPB59, MPB64, MPT64, TB15, TB18, TB21, TB33, TB38, TB54, TB12.5, TB20.6, TB40.8, TB10C, TB15A, TB17, TB24, TB27B, TB13A, TB64, TB11B, TB16, TB16A, TB32, TB32A, TB51, TB14, TB27, HBHA, GroEL, GroES (WO 95/01441, WO 98/44119, U.S. Pat. No. 6,596,281, U.S. Pat. No. 6,641,814, WO 99/04005, WO 00/21983, WO 99/24577), and the antigens disclosed in WO 92/14823, WO 95/14713, WO 96/37219, U.S. Pat. No. 5,955,077, U.S. Pat. No. 6,599,510, WO 98/31388, US 2002/0150592, WO 01/04151, WO 01/70991, WO 01/79274, WO 2004/006952, WO 97/09428, WO 97/09429, WO 98/16645, WO 98/16646, WO 98/53075, WO 98/53076, WO 99/42076, WO 99/42118, WO 99/51748, WO 00/39301, WO 00/55194, WO 01/23421, WO 01/24820, WO 01/25401, WO 01/62893, WO 01/98460, WO 02/098360, WO 03/070187, U.S. Pat. Nos. 6,290,969, 6,338,852, 6,350,456, 6,458,366, 6,465,633, 6,544,522, 6,555,653, 6,592,877, 6,613,881, 6,627,198. Antigen fusions that may be of particular use are those disclosed for the first time herein (such as Ag85A-Ag85B-TB10.4 and combinations thereof), but also known fusions such as ESAT-6-MPT59 and MPT59-ESAT-6 disclosed in WO 98/44119 and in the above-referenced documents.

One approach for applying multiple antigens may be to have two or more separate expression cassettes present in one vector, each cassette comprising a separate gene of interest. This approach clearly has disadvantages, e.g., related to space availability in the vector: separate cassettes generally comprise separate promoters and/or inducers and separate polyadenylation signal sequences. Such cassettes typically require separate positions in the viral vector, resulting in more laborious cloning procedures, whereas a phenomenon known as "promoter interference" or "squelching" (limited availability of cellular factors required by the promoters to act) may restrict the expression levels from the different promoters.

As exemplified by the recombinant viral vectors disclosed herein relating to fusions between multiple TB antigens, one is now able to make recombinant adenoviral vectors comprising several nucleic acids encoding more than one antigen, which viral vector elicits a strong immune response, whereas the use of single inserts elicit limited effects. Clearly, these vectors encode recombinant genetic chimeras that express the two or more antigens in a single cistronic mRNA, for example, in the form of a fusion protein. This approach can be effective when DNA vaccines or the viral vectors are being used to invoke T cell immunity to the passenger antigens. However, such fusion proteins may have additional drawbacks that cannot always be envisioned beforehand. It was found that such fusions might skew immunodominant patterns and do not always invoke immunity to all target antigens with equal potency. A second and perhaps more significant drawback to expression of genetic fusions is that the individual components may not fold to a native conformation due to the close presence of their fusion partner or other reasons. As a result of this, genetic fusions may invoke antibody responses to nonsense epitopes and such antibodies do not recognize native epitopes displayed by the founder pathogens and may be poor at combating infection.

We have now developed a system wherein multiple antigens are encoded by a single heterologous nucleic acid sequence, wherein the expressed polyprotein is processed into the discrete antigenic polypeptides. Thus, in one embodiment, the invention relates to viral vectors that enable the expression of multiple antigens that are subsequently processed into the discrete antigens, thus avoiding the possible limitations associated with genetic fusions, while also excluding the need for separate expression cassettes.

Heretofore, no compositions or methods have been described that enable precise processing of viral vector-expressed genetic fusions into discrete antigens. The expression of multiple antigens encoded by nucleic acids comprised in a DNA or viral vector, which antigens are subsequently processed into discrete antigens, is demonstrated by the use of a protease (PR), such as the viral protease encoded by Avian Leucosis Virus (ALV; referred to as PR-ALV herein). In ALV, ALV-PR forms the C-terminal domain of the gag protein, which is known to catalyze the processing of gag and gag-pol precursors, a critical step during ALV replication (reviewed by Skalka, 1989).

A unique ALV-PR-directed processing system was created. A polyprotein containing ALV-PR and given antigens is expressed by DNA or viral vectors, in which ALV-PR preferably forms the N-terminus of a polyprotein followed by antigen sequences that are linked with ALV-PR digestion sites. Two different cleavage sites are preferably used in the system. One cleavage site (SEQ ID NO:22) is to release ALV-PR and the other cleavage site (SEQ ID NO:21) is recognized by ALV-PR and used to separate the other encoded antigens in discrete polypeptides.

Alternatively, the PR and its cleavage sites may be encoded by or based on other retroviruses such as Human Immunodeficiency Virus (HIV), murine leukemia virus, Simian Immunodeficiency Virus (SIV) and Rous Sarcoma Virus.

According to a typical embodiment, the invention discloses recombinant viral vectors comprising nucleic acid sequences encoding multiple antigens from *Mycobacterium tuberculosis*, wherein the different nucleic acid sequences are separated from each other by sequences encoding the ALV protease recognition site. In this, the discrete TB antigens are produced as a polyprotein and subsequently processed, such that they are cleaved into discrete antigenic polypeptides, each contributing to the immune response. It is to be understood that the ALV protease system is not to be limited to the use of TB-specific antigens. A person skilled in the art will appreciate the possibility that the system has for applying other antigens, different from or in combination with TB antigens, and its applicability in other therapeutic settings such as gene therapy and tumor vaccination.

Preferably, the viral vector comprising the multiple antigen-encoding sequences separated by protease sites is an adenoviral vector. The viral vector may be the viral particle itself, whereas the term viral vector also refers to the nucleic acid encoding the viral particle. The adenoviral vector is preferably a recombinant vector based on, or derived from, an adenovirus species or serotype that encounters neutralizing activity in a low percentage of the target population. Such adenoviruses are also sometimes referred to as "rare" adenoviruses as they generally do not regularly circulate within the human population. Typical serotypes are, therefore, Ad11, Ad24, Ad26, Ad34, Ad35, Ad48, Ad49 and Ad50.

As used herein, "antigen" means a protein or fragment thereof that, when expressed in an animal or human cell or tissue, is capable of triggering an immune response. Examples include, but are not limited to, viral proteins, bacterial proteins, parasite proteins, cytokines, chemokines, immunoregulatory agents, and therapeutic agents. The antigen may be a wild-type protein, a truncated form of that protein, a mutated form of that protein or any other variant of that protein, in each case capable of contributing to immune responses upon expression in the animal or human host to be vaccinated. It is to be understood that when antigens are directly fused, this fusion is the result of recombinant molecular biology; thus, a direct fusion of two antigens as used herein does not refer to two antigenic parts of a single wild-type protein as it occurs in nature. For the sake of clarity, when two antigenic parts of a single wild-type protein (which two parts are normally directly linked within the protein) are linked via linkers as disclosed herein (such as through the ALV protease site, as discussed below), such fusion is part of the invention. In typical embodiments, the invention relates to different proteins (having antigenic activity) that are either directly linked or that are linked through one or more protease sites. In a more typical embodiment, the gene encoding the protease is linked to the protein(s) of interest, even more preferably through yet another protease site.

The different antigens are not necessarily from one pathogenic species. Combinations of different antigens from multiple species, wherein the different antigens are encoded by nucleic acid sequences within a single vector, are also encompassed.

A "host antigen" means a protein or part thereof that is present in the recipient animal cell or tissue, such as, but not limited to, a cellular protein, an immunoregulatory agent, or a therapeutic agent.

The antigen may be encoded by a codon-optimized, synthetic gene and may be constructed using conventional recombinant DNA methods.

As mentioned, the antigen that is expressed by the recombinant viral vector comprising the ALV protease system can be any molecule that is expressed by any viral, bacterial, or parasitic pathogen prior to or during entry into, colonization of, or replication in their animal host. These pathogens can be infectious in humans, domestic animals or wild animal hosts.

The viral pathogens from which the viral antigens are derived include, but are not limited to: Orthomyxoviruses, such as influenza virus; Retroviruses, such as RSV, HTLV-1, and HTLV-II, Herpesviruses such as EBV; CMV or herpes simplex virus; Lentiviruses, such as HIV-1 and HIV-2; Rhabdoviruses, such as rabies virus; Picornaviruses, such as Poliovirus; Poxviruses, such as vaccinia virus; Rotavirus; and Parvoviruses, such as Adeno-Associated Viruses (AAV).

Examples of viral antigens can be found in the group including, but not limited to, the Human Immunodeficiency Virus (HIV) antigens Rev, Pol, Nef, Gag, Env, Tat, mutant derivatives of Tat, such as Tat-Δ31-45, T- and B-cell epitopes of gp120, chimeric derivatives of HIV-1 Env and gp120, such as a fusion between gp120 and CD4, a truncated or modified HIV-1 Env, such as gp140 or derivatives of HIV-1 Env and/or gp140. Other examples are the hepatitis B surface antigen, rotavirus antigens, such as VP4 and VP7, influenza virus antigens, such as hemagglutinin, neuraminidase, or nucleoprotein, and herpes simplex virus antigens such as thymidine kinase.

Examples of bacterial pathogens from which the bacterial antigens may be derived include, but are not limited to, *Mycobacterium* spp., *Helicobacter pylori, Salmonella* spp., *Shigella* spp., *E. coli, Rickettsia* spp., *Listeria* spp., *Legionella pneumoniae, Fansicella* spp., *Pseudomonas* spp., *Vibrio* spp., and *Borellia burgdorferi*.

Examples of protective antigens of bacterial pathogens include the somatic antigens of enterotoxigenic *E. coli*, such as the CFA/I fimbrial antigen and the nontoxic B-subunit of the heat-labile toxin; pertactin of *Bordetella pertussis*, adenylate cyclase-hemolysin of *B. pertussis*, fragment C of tetanus toxin of *Clostridium tetani*, OspA of *Borellia burgdorferi*, protective paracrystalline-surface-layer proteins of *Rickettsia prowazekii* and *Rickettsia typhi*, the listeriolysin (also known as "Llo" and "Hly") and/or the superoxide dismutase (also known as "SOD" and "p60") of *Listeria monocytogenes*, urease of *Helicobacter pylori*, and the receptor-binding domain of lethal toxin and/or the protective antigen of *Bacillus anthrax*.

The parasitic pathogens from which the parasitic antigens are derived include, but are not limited to: *Plasmodium* spp. such as *Plasmodium falciparum, Trypanosome* spp. such as *Trypanosoma cruzi, Giardia* spp. such as *Giardia intestinalis, Boophilus* spp., *Babesia* spp. such as *Babesia microti, Entamoeba* spp. such as *Entamoeba histolytica, Eimeria* spp. such as *Eimeria maxima, Leishmania* spp., *Schistosome* spp., *Brugia* spp., *Fascida* spp., *Dirofilaria* spp., *Wuchereria* spp., and *Onchocerea* spp.

Examples of protective antigens of parasitic pathogens include the circumsporozoite (CS) or Liver Stage Specific (LSA) antigens LSA-1 and LSA-3 of *Plasmodium* spp. such as those of *P. bergerii* or *P. falciparum*, or immunogenic mutants thereof; the merozoite surface antigen of *Plasmodium* spp., the galactose-specific lectin of *Entamoeba histolytica*, gp63 of *Leishmania* spp., gp46 of *Leishmania major*, paramyosin of *Brugia malayi*, the triose-phosphate isomerase of *Schistosoma mansoni*, the secreted globin-like protein of *Trichostrongylus colubriformis*, the glutathione-S-transferase of *Frasciola hepatica, Schistosoma bovis* and *S. japonicum*, and KLH of *Schistosoma bovis* and *S. japonicum*.

As mentioned earlier, the recombinant viral vectors comprising nucleic acids encoding the ALV or ALV-like protease may encode host antigens, which may be any cellular protein, immunoregulatory agent, or therapeutic agent, or parts thereof, that may be expressed in the recipient cell including, but not limited to, tumor, transplantation, and autoimmune antigens, or fragments and derivatives of tumor, transplantation, and autoimmune antigens thereof. Thus, in the invention, viral vectors may encode tumor, transplant, or autoimmune antigens, or parts or derivatives thereof. Alternatively, the viral vectors may encode synthetic genes (made as described above) that encode tumor-specific, transplant, or autoimmune antigens or parts thereof. Examples of such antigens include, but are not limited to, prostate-specific antigen, MUC1, gp100, HER2, TAG-72, CEA, MAGE-1, tyrosinase, CD3, and IAS beta chain.

The ALV protease site technology as disclosed herein is also applicable for gene therapy applications by introducing multiple polypeptides in a single polyprotein and having the polyprotein processed into discrete polypeptides in hosts in need of these multiple (discrete) polypeptides.

As a means to further enhance the immunogenicity of the viral vectors, expression cassettes are constructed that encode at least one antigen and an adjuvant, and can be used to increase host responses to the antigen expressed by the viral vectors. Such adjuvants are herein also referred to as "genetic adjuvants" as genes encode the proteins that act as adjuvant. A typical use is made of the protease and the linking protease sites as described above to have the antigen cleaved from the adjuvant after translation, although in certain embodiments the adjuvant may also be directly linked to the antigen.

The particular adjuvant encoded by the viral vectors may be selected from a wide variety of genetic adjuvants. In a typical embodiment, the adjuvant is the A subunit of cholera toxin (CtxA; examples: GenBank accession no. X00171, AF175708, D30053, D30052), or functional parts and/or functional mutant derivatives thereof, such as the A1 domain of the A subunit of Ctx (CtxA1; GenBank accession no. K02679). Alternatively, any bacterial toxin that is a member of the family of bacterial adenosine diphosphate-ribosylating exotoxins may be used. Non-limiting examples are the A subunit of heat-labile toxin (EltA) of enterotoxigenic *E. coli*, and the pertussis toxin S1 subunit. Other examples are the adenylate cyclase-hemolysins such as the cyaA genes of *Bordetella pertussis, B. bronchiseptica* or *B. parapertussis*. Alternatively, the particular ADP-ribosyltransferase toxin may be any derivative of the A subunit of cholera toxin (i.e., CtxA), or parts thereof (i.e., the A1 domain of the A subunit of Ctx (i.e., CtxA1), from any classical *Vibrio cholerae* strain (e.g., strain 395) or E1 Tor *V. cholerae* (e.g., strain 2125) that display reduced ADP-ribosyltransferase catalytic activity but retain the structural integrity including, but not restricted to, replacement of arginine-7 with lysine (R7K), serine-41 with phenylalanine (S41F) serine-61 with lysine (S61K), serine-63 with lysine (S63K), valine-53 with aspartic acid (V53D), valine-97 with lysine (V97K) or tyrosine-104 with lysine (Y104K), or combinations thereof. Alternatively, the particular ADP-ribosyltransferase toxin may be any derivative of cholera toxin that fully assemble, but are nontoxic proteins due to mutations in the catalytic-site, or adjacent to the catalytic site, respectively. Such mutants are made by conventional site-directed mutagenesis procedures, as described below.

The ADP-ribosyltransferase toxin may be any derivative of the A subunit of heat-labile toxin (LtxA) of enterotoxigenic *Escherichia coli* isolated from any enterotoxigenic *E. coli* including, but not restricted to, *E. coli* strain H10407 that display reduced ADP-ribosyltransferase catalytic activity but retain the structural integrity including, but not restricted to, R7K, S41F, S61K, S63K, V53D, V97K or Y104K, or combinations thereof. Alternatively, the particular ADP-ribosyltransferase toxin may be any fully assembled derivative of cholera toxin that is nontoxic due to mutations in, or adjacent to, the catalytic site. Such mutants are made by conventional site-directed mutagenesis procedures, as described below.

Although ADP-ribosylating toxins are potent adjuvants, the adjuvant encoded by the viral vectors in the invention may also be any bioactive protein from viral, bacterial or protozoan organisms, immunoregulatory DNA, double-stranded RNA or small inhibitory RNA (herein referred to as siRNA). The particular bioactive protein can be selected from, but not restricted to, the following classes:

Class 1. This class of adjuvants induce apoptosis by inhibiting Rho, a host small GTPase. Inhibition of Rho has been clearly associated with the induction of apoptosis. Induction of apoptosis is a useful method to drive bystander T cell responses and a potent method for the induction of CTLs. This strategy has not been evaluated in any experimental system thus far. The active domain of SopE is contained in amino acids 78-240 and it only requires a 486 by gene for expression. The catalytic domain of *E. coli* CNF-1 is likely to possess similar properties.

Class 2. Bacterial porins have been shown to possess immune-modulating activity. These hydrophobic homotrimeric proteins form pores that allow passage of molecules of Mr<600 Da through membranes. Examples of porins include the OmpF, OmpC and OmpD proteins of the *Enterobacteriaceae.*

Class 3. Double-stranded RNA (dsRNA) activates host cells, including dendritic cells. Expression of an mRNA that encodes an inverted repeat spaced by an intro or ribozyme will result in the expression of dsRNA.

Class 4. The peptide motive [WYF]xx[QD]xx[WYF] is known to induce CD1d-restricted NK T cell responses (Kronenberg and Gapin, 2002). Expression of a peptide with this motif fused to a T4 fibritin coiled-coiled motif will produce trimeric peptide that will cross-link TCRs on CD1d-restricted T cells, thereby activating innate host responses.

Class 5. siRNA can be used to target host mRNA molecules that suppress immune responses (e.g., kir), regulate immune responses (e.g., B7.2) or prevent cross-presentation (e.g., Rho).

Class 6. siRNAs can be used for vaccines that target co-stimulatory molecules, e.g., CD80 and CD86. Inhibition of these molecules will prevent co-stimulation, thereby resulting in T cell anergy.

Surprisingly, it has been found that antigens from TB-causing bacilli, such as the TB10.4 protein, may not only act as an antigen in itself, but even act as an adjuvant towards other TB antigens, e.g., Ag85A. In the case where a triple insert was present (Ag85A-Ag85B-TB10.4), it was surprisingly found that the presence of TB10.4 in this construct stimulated the immune response towards Ag85A, whereas the absence of TB10.4 revealed a minor effect towards CD8+ see Example 4 and FIG. 13, Panel B). The adjuvant effect of TB10.4 was further investigated and it was found that TB10.4 stimulated the activation of CD8 cells directed against Ag85A when present in a triple construct, whereas an infection with separate vectors each encoding the separate antigens did not result in such stimulation, strongly suggesting that the TB10.4 antigen should be present, either in the same vector, or present within the same translated product.

Also described are viral vectors that encode at least one antigen and a cytokine fused by a protease recognition site. Such vectors are used to increase host responses to the passenger antigen(s) expressed by the viral vectors. Examples of cytokines encoded by the viral vectors are interleukin-4 (IL-4), IL-5, IL-6, IL-10, IL-$12_{p40}$, IL-$12_{p70}$, TGFβ, and TNFα.

Recombinant DNA and RNA procedures for the introduction of functional expression cassettes to generate viral vectors capable of expressing an immunoregulatory agent in eukaryotic cells or tissues are known in the art.

Herein, compositions and methods are described for the construction of viral vectors that express more than one antigen from a TB-causing bacillus, preferably *Mycobacterium tuberculosis, M. africanum* and/or *M. bovis.* Preferably, the viral vector is a replication-defective recombinant adenoviral vector. One extensively studied and generally applied adenovirus serotype is adenovirus 5 (Ad5). The existence of anti-Ad5 immunity has been shown to suppress substantially the immunogenicity of Ad5-based vaccines in studies in mice and rhesus monkeys. Early data from phase-1 clinical trials show that this problem may also occur in humans.

One promising strategy to circumvent the existence of pre-existing immunity in individuals previously infected with the most common human adenoviruses (such as Ad5), involves the development of recombinant vectors from adenovirus serotypes that do not encounter such pre-existing immunities. Human adenoviral vectors that were identified to be particularly useful are based on serotypes 11, 26, 34, 35, 48, 49, and 50 as was shown in WO 00/70071, WO 02/40665 and WO 2004/037294 (see also Vogels et al. 2003). Others have also found that adenovirus 24 (Ad24) is of particular interest as it is shown to be a rare serotype (WO 2004/083418). In a typical embodiment, the viral vector is thus an adenovirus derived from a serotype selected from the group consisting of: Ad11, Ad24, Ad26, Ad34, Ad35, Ad48, Ad49 and Ad50. The advantage of this selection of human adenoviruses as vaccine vectors lies clearly in the fact that humans are not regularly infected with these wild-type adenoviruses. As a consequence, neutralizing antibodies against these serotypes is less prevalent in the human population at large. This is in contrast to serotype 5, because humans are quite regularly infected with this wild-type serotype. The immune responses raised during an infection with a parental wild-type serotype can negatively impact the efficacy of the recombinant adenovirus serotype when used as a subsequent recombinant vaccine vector, such as a vaccine against malaria in which adenoviruses are applied. The spread of the different adenovirus serotypes in the human worldwide population differs from one geographic area to the other. Generally, the typical serotypes encounter a low neutralizing activity in hosts in most parts of the world, as outlined in WO 00/70071. In another typical embodiment, the adenovirus is a simian, canine or a bovine adenovirus, since these viruses also do not encounter pre-existing immunity in the (human) host to which the recombinant virus is to be administered. The applicability of simian adenoviruses for use in human gene therapy or vaccines is well appreciated by those of ordinary skill in the art. Besides this, canine and bovine adenoviruses were found to infect human cells in vitro and are, therefore, also applicable for human use. Particularly typical simian adenoviruses are those isolated from chimpanzee. Examples that are suitable include C68 (also known as Pan 9; U.S. Pat. No. 6,083, 716) and Pan 5, 6 and 7 (WO 03/046124); see also WO 03/000851.

Thus, choice of the recombinant vector is influenced by those that encounter neutralizing activity in a low percentage of the human population in need of the vaccination. The advantages of the invention are multi-fold. Recombinant viruses, such as recombinant adenoviruses, can be produced to very high titers using cells that are considered safe and that can grow in suspension to very high volumes, using medium that does not contain any animal- or human-derived components. Also, it is known that recombinant adenoviruses elicit a dramatic immune response against the protein encoded by the heterologous nucleic acid sequence in the adenoviral genome.

We realized that a vaccine comprising multiple antigens would provide a stronger and broader immune response towards the TB-causing bacillus. Moreover, despite the fact that a single antigen could by itself induce protection in inbred strains of mice, a cocktail comprising several antigens is conceivably a better vaccine for applications in humans as it is less likely to suffer from MHC-related unresponsiveness in a heterogeneous population.

However, from a practical standpoint of vaccine development, a vaccine consisting of multiple constructs would be very expensive to manufacture and formulate. In addition to simplifying the manufacturing process, a single construct may ensure equivalent uptake of the components by antigen-presenting cells and, in turn, generate an immune response that is broadly specific.

In one aspect, the replication-defective recombinant viral vector comprises a nucleic acid sequence coding for an antigenic determinant wherein the heterologous nucleic acid sequence is codon-optimized for elevated expression in a mammal, preferably a human. Codon-optimization is based on the required amino acid content, the general optimal codon usage in the mammal of interest and a number of aspects that should be avoided to ensure proper expression. Such aspects may be splice-donor or -acceptor sites, stop codons, Chi-sites, poly(A) stretches, GC- and AT-rich sequences, internal TATA boxes, etc. Methods of codon optimization for mammalian hosts are well known to the skilled person and can be found in several places in molecular biology literature.

Also described is a replication-defective recombinant adenoviral vector hereof, wherein the adenine plus thymine content in the heterologous nucleic acid, as compared to the cytosine plus guanine content, is less than 87%, preferably less than 80%, more preferably less than 59% and most preferably equal to approximately 45%.

The production of recombinant adenoviral vectors harboring heterologous genes is well-known in the art and typically involves the use of a packaging cell line, adapter constructs and cosmids and deletion of at least a functional part of the E1 region from the adenoviral genome (see also below for packaging systems and typical cell lines).

The vaccines herein are typically held in pharmaceutically acceptable carriers or excipients. Pharmaceutically acceptable carriers or excipients are well known in the art and used extensively in a wide range of therapeutic products. Preferably, carriers are applied that work well in vaccines. More preferably, the vaccines further comprise an adjuvant. Adjuvants are known in the art to further increase the immune response to an applied antigenic determinant.

Also described is the use of a kit as described herein in the therapeutic, prophylactic or diagnostic treatment of TB.

The recombinant viral vectors comprising TB antigens of the invention may be used in vaccination settings in which they are applied in combination with BCG. They may also be applied as a priming agent or a boosting agent, respectively preceding or following a BCG vaccination to increase the desired immune responses. It can also be envisioned that different viral vectors as disclosed herein are used in prime-boost setups, wherein one vector is followed by another. Moreover, vectors comprising directly linked antigens may be combined as such with vectors comprising the protease site-linked antigens. Prime-boost settings using one adenovirus serotype as a prime and another serotype as a boost (selected from the typical human, simian, canine or bovine adenoviruses) are also envisioned. The viral vectors hereof may also be used in combination with vaccines comprising purified (recombinantly produced) antigens and/or with vaccines comprising naked DNA or RNA encoding similar or the same antigens.

Thus, a recombinant replication-defective adenovirus comprising a nucleic acid sequence may encode two or more antigens from at least one tuberculosis- (TB-) causing bacillus. It is to be understood that a polypeptide may comprise several antigenic parts or antigenic fragments (=antigens). Also, a protein itself may be considered as being an "antigen." Preferably, the recombinant adenovirus is a human or a simian adenovirus. More preferably, the adenovirus used as a recombinant vector in the invention is selected from the group consisting of human adenovirus serotypes Ad11, Ad24, Ad26, Ad34, Ad35, Ad48, Ad49 and Ad50. The TB-causing bacillus used for providing the typical antigen(s) is preferably *Mycobacterium tuberculosis, Mycobacterium africanum* and/or *Mycobacterium bovis,* and two or more antigens are preferably selected from the group consisting of antigens encoded by the Ag85A, Ag85B, ESAT-6, f72 and TB10.4 open reading frames of *M. tuberculosis.* In a highly typical embodiment, the nucleic acid sequence encodes at least two antigens selected from the group consisting of antigens encoded by the Ag85A, Ag85B, and TB10.4 open reading frames of *M. tuberculosis.* In an even more typical embodiment, the adenovirus hereof comprises a nucleic acid sequence encoding the full length proteins Ag85A, Ag85B and TB10.4, wherein it is even more typical that these three proteins are encoded by a nucleic acid comprising a sequence in which the genes encoding the respective proteins are cloned in that 5' to 3' order (Ag85A-Ag85B-TB10.4).

Also described is a recombinant adenovirus, wherein at least two of the antigens are expressed from one polyprotein. In one typical embodiment, at least two of the antigens are linked so as to form a fusion protein. The linkage may be direct or via a connecting linker of at least one amino acid. Where a linker is used to connect two separate antigens and thus to provide a fusion protein of two or more antigens hereof, preferably one or more linkers according to SEQ ID NO:23 is used.

Also described is a multivalent TB vaccine comprising a recombinant adenovirus hereof or a recombinant polynucleotide vector hereof, further comprising a pharmaceutically acceptable excipient, and optionally an adjuvant. Many pharmaceutically acceptable recipients and adjuvants are known in the art.

Further described is a method of vaccinating a mammal for the prevention or treatment of TB, comprising administering to the mammal a recombinant adenovirus, a multivalent TB vaccine or a recombinant polynucleotide vector hereof. In one aspect, the invention relates to a method of vaccinating a mammal for the prevention or treatment of TB, comprising the steps of administering to the mammal a recombinant adenovirus, a multivalent TB vaccine, or a recombinant polynucleotide vector hereof as a priming vaccination, and administering to the mammal a recombinant adenovirus, a multivalent TB vaccine, or a recombinant polynucleotide vector hereof as a boosting vaccination. Also described is a recombinant adenovirus, a multivalent TB vaccine, or a recombinant polynucleotide vector hereof, either one for use as a medicament, preferably in the prophylactic, therapeutic, or diagnostic treatment of tuberculosis. Also described is the use of a recombinant adenovirus, a multivalent TB vaccine, or a recombinant polynucleotide vector hereof in the preparation of a medicament for the prophylactic or therapeutic treatment of tuberculosis.

In one particular aspect, a recombinant polynucleotide vector comprising a nucleic acid sequence encodes two or more antigens and a protease-recognition site, wherein the antigens are expressed as a polyprotein, the polyprotein comprising the protease recognition site separating at least two of the two or more antigens. The polynucleotide vector may be a naked DNA, a naked RNA, a plasmid, or a viral vector. In a typical embodiment, the viral vector is packaged into a replication-defective human or simian adenovirus. It is to be understood that a viral vector may be seen as two kinds of entities: the viral DNA encoding the virus may be used as a nucleic acid vector, while the virus (comprising the viral vector DNA) may also be used to transfer the nucleic acid of interest to a host cell through infection of the host cell.

Thus, a "vector" as used herein refers to a means for transferring a gene or multiple genes of interest to a host. This may be achieved by direct injections of the DNA, RNA, plasmid, or the viral nucleic acid vector, but may also be achieved by infecting host cells with a recombinant virus (which then acts as the vector). As exemplified herein, viruses may be used to immunize mammals (for example, mice), whereas the DNA (for instance, in the form of the adapter plasmid carrying the gene(s) of interest and a part of the viral DNA) may also be directly injected in the mammal for immunizing the mammal. Vaccines based on naked DNA, or RNA, or plasmids are known in the art, whereas vaccines based on recombinant viruses are also known. For clarity issues, all entities that deliver a gene or more genes of interest to a host cell are regarded as a "vector."

In one typical embodiment, the nucleic acid present in the vector comprises a sequence encoding a protease, wherein it is typical that the protease upon expression is expressed as part of the polyprotein and is linked to at least one of the antigens by a protease-recognition site.

Particularly typical protease-recognition sites comprise a sequence according to SEQ ID NO:21 or SEQ ID NO:22. More typical is a recombinant polynucleotide vector hereof, wherein the protease is from an Avian Leukosis Virus (ALV). In a typical aspect, the antigens that are linked through a protease recognition site are from at least one tuberculosis- (TB-) causing bacillus, wherein the TB-causing bacillus is preferably *Mycobacterium tuberculosis*, *Mycobacterium africanum* and/or *Mycobacterium bovis*. The two or more antigens are preferably selected from the group consisting of antigens encoded by the Ag85A, Ag85B, ESAT-6, and TB10.4 open reading frames of *M. tuberculosis*, wherein the heterologous nucleic acid sequence encodes most preferably at least two antigens selected from the group consisting of antigens encoded by the Ag85A, Ag85B, and TB10.4 open reading frames of *M. tuberculosis*. Even more typical are polynucleotides hereof wherein the antigens are the full length Ag85A, Ag85B and TB10.4 polypeptides, of which the encoding genes are cloned in that 5' to 3' order. Fusion proteins based on these and other tuberculosis antigens were described in U.S. Pat. No. 5,916,558, WO 01/24820, WO 03/070187 and WO 2005/061534. However, the use of the nucleic acids hereof, encoding the fusion proteins disclosed herein, for incorporation into recombinant adenoviral vectors was not disclosed.

Also described is a recombinant polynucleotide vector comprising a heterologous nucleic acid sequence encoding an antigen and a genetic adjuvant. The term "genetic adjuvant" refers to a proteinaceous molecule that is encoded by a nucleic acid sequence. The antigen and the genetic adjuvant may be linked directly or in another embodiment linked indirectly, for instance, by a connection comprising a first protease-recognition site. In another typical aspect, the polynucleotide vector is a naked DNA, a naked RNA, a plasmid, or a viral vector. The viral vector is preferably packaged into a replication-defective human or simian adenovirus, wherein the adenovirus is even more preferably selected from the group consisting of human adenovirus serotypes Ad11, Ad24, Ad26, Ad34, Ad35, Ad48, Ad49 and Ad50.

Also typical are nucleic acids comprising a sequence encoding a protease, wherein the protease is preferably linked to the antigen and/or to the genetic adjuvant by a second protease-recognition site. The typical second protease-recognition site comprises a sequence according to SEQ ID NO:22, whereas the typical first protease-recognition site comprises a sequence according to SEQ ID NO:21. A typical protease is a protease from an Avian Leukosis Virus (ALV), while the antigens are preferably from at least a tuberculosis- (TB-) causing bacillus, more preferably *Mycobacterium tuberculosis*, *Mycobacterium africanum* and/or *Mycobacterium bovis*. Typical antigens are selected from the group consisting of: Ag85A, Ag85B, ESAT-6 and TB10.4. A most typical embodiment is a vector wherein the heterologous nucleic acid sequence encodes at least two antigens selected from the group consisting of *M. tuberculosis* antigens Ag85A, Ag85B, and TB10.4, wherein it is further typical to have a fusion polypeptide comprising the full length Ag85A, Ag85B and TB10.4 proteins, in that order from N- to C-terminus.

As disclosed herein, the TB10.4 has unexpected adjuvant activity, as it was found that it stimulates the immune response towards the other (especially Ag85A) antigen present in the polyprotein. The TB10.4 adjuvant is a typical genetic adjuvant. Thus, the invention also provides a recombinant vector comprising a nucleic acid encoding the TB10.4 antigen with at least one other antigen, which antigen is preferably a tuberculosis antigen, more preferably the Ag85A antigen. In an even more typical embodiment, the vector comprises a nucleic acid encoding the TB10.4 antigen and at least the Ag85A and Ag85B antigens. As outlined below, the TB10.4 is suggested to increase the processing of the multiple-antigen translation product towards the proteosome, resulting in a highly significant increase in CD8 response. It is very likely that the effect is not limited to Ag85A and TB10.4 alone, with a wider applicability of the TB10.4 antigen than limited to tuberculosis vaccines alone. Thus, the invention, in yet another embodiment, also relates to a recombinant vector comprising a nucleic acid encoding TB10.4 and at least one other antigen, wherein the other antigen is not a *Mycobacterium* antigen. The invention discloses the use of the *Mycobacterium* TB10.4 antigen as a genetic adjuvant.

Moreover, disclosed is the use of the TB10.4 antigen in the manufacture of a medicament for the treatment, diagnosis and/or prophylaxis of a disease other than tuberculosis, and at least in a disease in which the immune response towards the antigen of interest needs to be stimulated by the action of an adjuvant. So, it is disclosed that an antigen within TB10.4 of *Mycobacterium tuberculosis* can act as an adjuvant towards other antigens, such as Ag85A. Thus, also described is the use of the *Mycobacterium* antigen TB10.4 as a genetic adjuvant.

Furthermore, in another embodiment, the invention relates to the use of the *Mycobacterium* antigen TB10.4 in the preparation of a medicament for the treatment or prophylaxis of a disease in which the immune response of a host towards a certain antigen or therapeutic component of interest needs to be stimulated. The skilled person would be able to determine the level of immune response towards a given antigen of interest and whether an extra stimulation by the use of an adjuvant, such as a genetic adjuvant, herein exemplified by TB10.4, might be beneficial in a treated subject.

The invention further relates to a recombinant polynucleotide vector hereof, wherein the genetic adjuvant comprises a cholera toxin (CtxA1) or a mutant derivative thereof, the mutant derivative comprising a serine to lysine substitution at amino acid position 63 ($A1_{K63}$). Also described is a multivalent TB vaccine comprising a recombinant polynucleotide vector hereof, further comprising a pharmaceutically acceptable excipient, and optionally an adjuvant.

EXAMPLES

Example 1

Construction of Ad35-based Adapter Plasmids Carrying *M. Tuberculosis Antigens*

Here, the construction of adapter plasmids suitable to generate E1-deleted Ad35-based vectors capable of expressing single or multiple TB antigens is described. The examples relate to TB antigens Ag85A (Swissprot #P17944), Ag85B (Swissprot #P31952) and TB10.4 (Swissprot #053693) as non-limiting examples of means and methods to generate single- and multi-antigen vaccine preparations using Adenovirus-based replication-defective vectors. As already stated above, the principles applied here can also be applied to any combination of prophylactic or therapeutic polypeptide.

Construction of pAdApt35Bsu.myc

Adapter plasmid pAdApt35Bsu is described in applicant's application WO 2004/001032. This plasmid contains the left part of the Ad35 genome (including the left Inverted Terminal Repeat (ITR)), further lacking a functional E1 region, and an expression cassette comprising a CMV promoter inserted into the E1 region. The adapter also comprises a functional pIX promoter and a region of Ad35 downstream of the E1 region, which region is sufficient for a homologous recombination event with a cosmid comprising the remaining part of the Ad35 genome, leading to the generation of a recombinant replication-defective adenovirus in a packaging cell, which packaging cell provides all necessary elements and functions for a functional replication and packaging of the virus to be produced. The generation of recombinant adenoviruses using such adapter plasmids is a process well known to the skilled person.

pAdApt35Bsu was digested with NheI and XbaI and the 5 kb vector-containing fragment was isolated from agarose gel using the QIAQUICK® gel extraction kit (Qiagen) according to the manufacturer's instructions. A double-stranded (ds) linker was prepared from the following single-stranded (ss) oligos (synthesized by Sigma): Myc-oligo 1: (SEQ ID NO:1) and Myc-oligo 2: (SEQ ID NO:2). The two oligonucleotides were mixed using 2 µl of 0.5 µg/µl stocks in a total volume of 20 µl annealing buffer (10 mM Tris-HCl pH 7.9, 10 mM $MgCl_2$, 1 mM Dithiotreitol), incubated at 98° C. for two minutes and subsequently cooled down to 4° C. at a rate of 0.6° C. per minute using a PCR machine. The resulting ds linker was then ligated with the above-prepared pAdApt35Bsu vector in 3×, 6× or 9× molar excess of the linker. Colonies were tested for insertion of the linker sequence in correct orientation by digestion with NheI or XbaI, sites that are restored only in correct orientation. Sequencing confirmed that the linker consisted of the expected sequence. The resulting adapter plasmid is named pAdApt35Bsu.myc (FIG. 1).

Below, methods for cloning a large set of different constructs is provided. An overview of all constructs and their respective inserts is found in Table I.

TABLE I

Construct names and their respective inserts comprising nucleic acids encoding TB antigens.

| Construct | Insert |
|---|---|
| TB-3 | ALV-dig*-Ag85A-dig-Ag85B |
| TB-3M | ALV-dig*-Ag85A-dig-Ag85B-myc |
| TB-4 | Ag85A-Ag85B |
| TB-4M | Ag85A-Ag85B-myc |
| TB-5 | Ag85A |
| TB-5M | Ag85A-myc |
| TB-6 | Ag85B |
| TB-6M | Ag85B-myc |
| TB-7 | TB10.4 |
| TB-7M | TB10.4-myc |
| TB-S | Ag85A-Ag85B-TB10.4 |
| TB-SM | Ag85A-Ag85B-TB10.4-myc |
| TB-L | ALV-dig*-Ag85A-dig-Ag85B-dig-TB10.4 |
| TB-LM | ALV-dig*-Ag85A-dig-Ag85B-dig-TB10.4-myc |
| TB-FL | Ag85A-X-Ag85B-X-TB10.4 |
| TB-FLM | Ag85A-X-Ag85B-X-TB10.4-myc |

ALV = Avian Leukosis Virus protease;
dig* = a protease recognition site recognized by a cellular protease;
dig = protease recognition site recognized by the ALV protease;
X = flexible linker, not being a protease recognition site;
myc = myc-tag.

Construction of pAdApt35Bsu-Based Adapter Plasmids Containing Three TB Antigens

The heterologous nucleic acids of the invention encode the three *M. tuberculosis* antigens Ag85A, Ag85B and TB10.4 as a poly-protein from one mRNA. All fusion sequences indicated with an "M" contain a myc epitope (myc-tag: SKKTEQKLISEEDL; SEQ ID NO:9) attached to the 3' end of the sequence to allow analysis of expression using myc-specific antibodies in case the antibodies specific for the separate TB antigens do not recognize the fusions properly. Thus, the "M" in the names of all constructs described below relates to the myc-tag, whereas, all constructs were also made without a myc-tag.

In a first embodiment (TB-SM), the three antigens are expressed as a direct fusion polyprotein: Ag85A-Ag85B-TB10.4-myc (TB-S=Ag85A-Ag85B-TB10.4).

In a second embodiment (TB-LM), the polyprotein precursor contains a protease, which cleaves the three antigens intra-cellularly on incorporated digestion sites that separate them: linker/digestion site sequence: PPSKSKKG-GAAAMSSAIQPL VMAVVNRERDGQTG (SEQ ID NO:21). This digestion occurs through a sequence-specific protease fused to the N-terminus of the fusion protein. This protease, derived from the gag gene of the Avian Leukosis Virus (ALV), is also cleaved resulting in four separate proteins after protease digestion. The polyprotein may be as follows: ALV-dig*-Ag85A-dig-Ag85B-dig-TB10.4-myc (in which "dig*" relates to the digestion site separating the protease from the antigens (GSSGPWPAPEPPAV SLAMTMEHRDRPLV; SEQ ID NO:22) of the protease and "dig" relates to the digestion site between the antigens, see above; TB-L=ALV-dig*-Ag85A-dig-Ag85B-dig-TB10.4). Both protease-cleavable linkers, as well as self-cleavage linkers, may be used in the vectors of the invention and are encompassed herein. The use of self-processing cleavage sites has been described in WO 2005/017149.

In a third embodiment, the poly-protein (TB-FLM) comprises the mentioned *M. tuberculosis* antigens separated by a linker sequence that is not cleaved (as in the second embodiment described above) but allows proper and independent folding of each of the three antigens: Ag85A-X-Ag85B-X-TB10.4-myc (in which "X" relates to a flexible linker: GTGGSGGTGSGTGGSV; SEQ ID NO:23). All these fusion proteins were also made without the myc-tag (referred to as TB-S, TB-L and TB-FL, respectively) using similar construction methods (see below).

The desired protein sequences were assembled using the above indicated published protein sequences for the *M. tuberculosis* antigens, the ALV protease PR p15 sequence as published in Genbank (Acc. No.CAA86524) and the protease digestion site as in Genbank Acc. No. AAK13202 amino acids 476-500. The three protein sequences were then back translated to DNA coding sequences optimized for expression in humans and subsequently synthesized, assembled and cloned in pCR-Script vectors by Geneart (Germany).

The codon-optimized DNA sequences for TB-LM are provided (FIG. 19; SEQ ID NO:3), TB-SM (FIG. 20; SEQ ID NO:4) and TB-FLM (FIG. 21; SEQ ID NO:5), as well as the protein sequences for TB-LM (FIG. 22; SEQ ID NO:6), TB-SM (FIG. 23; SEQ ID NO:7) and TB-FLM (FIG. 24; SEQ ID NO:8). The myc epitope is contained within the C-terminal sequence SKKTEQKLISEEDL (SEQ ID NO:9) in each of the fusion proteins, which sequence is not present in the case of TB-L, TB-S and TB-FL, respectively.

Figure 2:
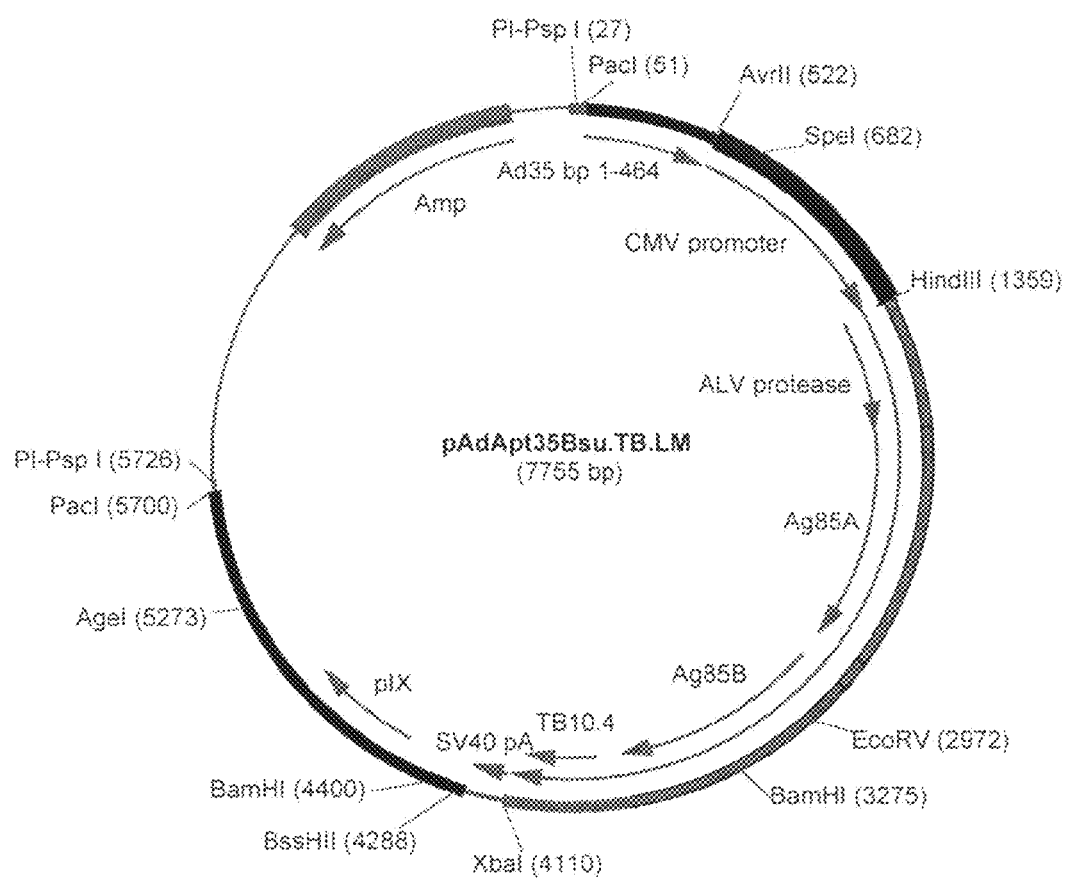
FIG. 2: Map of pAdApt35Bsu.TB.LM.
Figure 3:
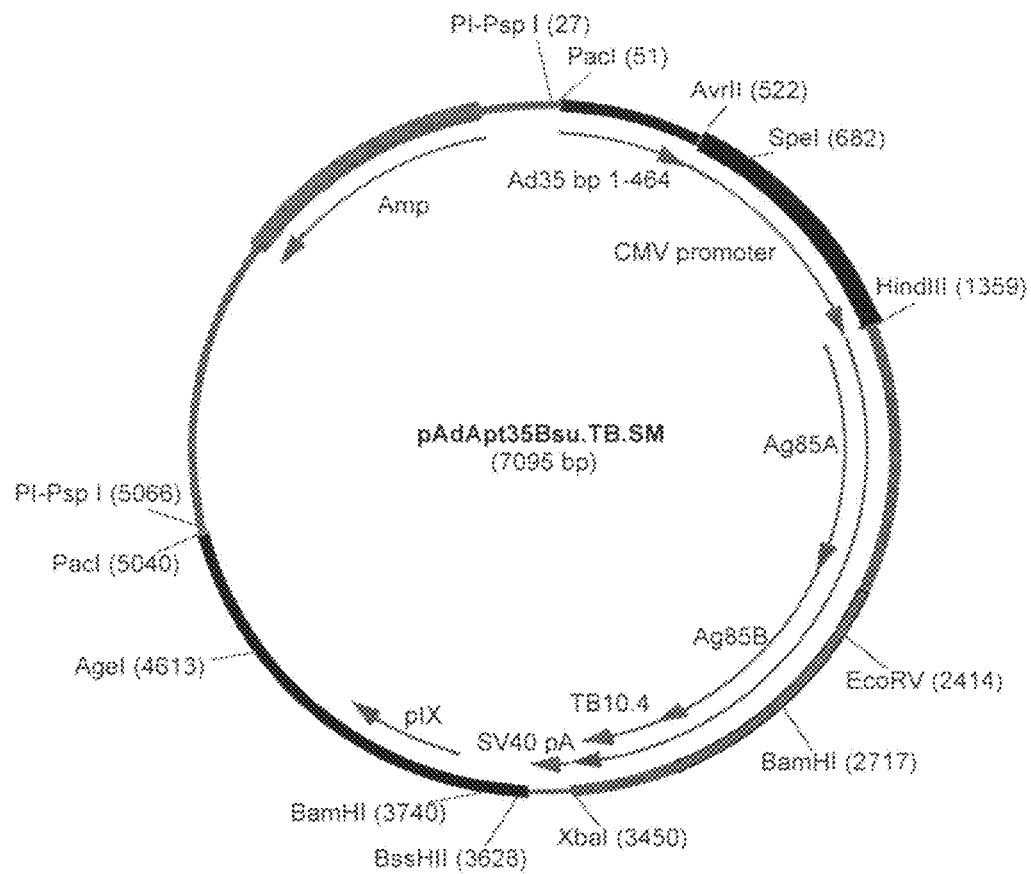
FIG. 3: Map of pAdApt35Bsu.TB.SM.
Figure 4:
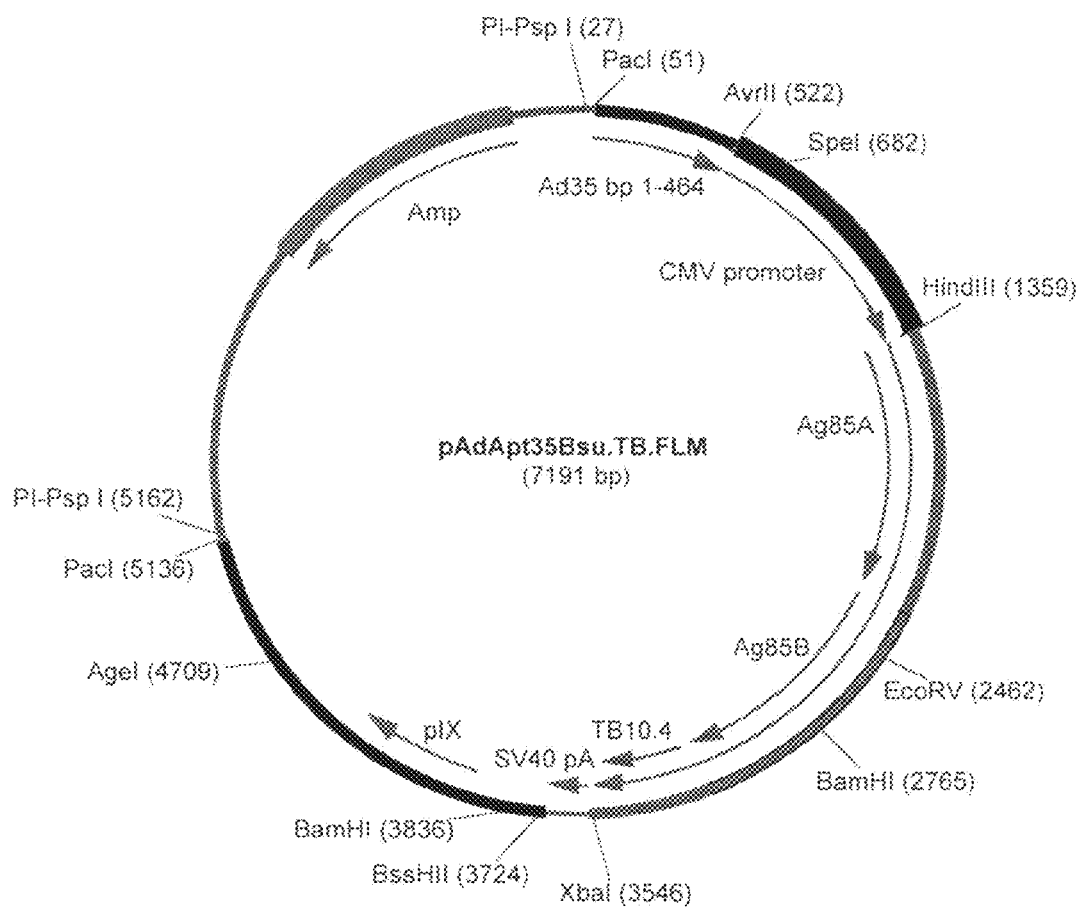
FIG. 4: Map of pAdApt35Bsu.TB.FLM.

The cloned fusion genes were then digested with HindIII, XbaI and ApaLI after which the 2.7 kb (TB-L), 2.2 kb (TB-FL) and 2.1 kb (TB-S) fragments were isolated from agarose gel as described above. ApaLI digestion was done to digest the plasmid vector in fragments that were better separable from the inserts. Plasmid pAdApt35Bsu was also digested with HindIII and XbaI and the vector-containing fragment was isolated from gel as above. The isolated pAdApt35Bsu vector was ligated in separate reactions to each of the isolated fragments containing the TB sequences and transformed into DH5α-competent bacteria (Invitrogen). Resulting colonies were analyzed by digestion with HindIII and XbaI and plasmid clones containing the expected insert were selected. This resulted in pAdApt35Bsu.TB.LM (FIG. 2), pAdApt35Bsu.TB.SM (FIG. 3) and pAdApt35Bsu.TB.FLM (FIG. 4), all containing a myc-tag. To generate adapter plasmids expressing the fusion genes without myc-tag, the inserts are first PCR-amplified using the following primers and templates:

Fragment TB-L
ALVprot.FW: (SEQ ID NO:10) and 10.4.RE.stop: (SEQ ID NO:11) with TB-LM as template.

Fragment TB-FL and TB-S
85A.FW: (SEQ ID NO:12) and 10.4.RE.stop with TB-FLM or TB-SM as template.

The amplifications were done with PHUSION® DNA polymerase (Bioke) according to the manufacturer's instructions. The following program was used: two minutes at 98° C. followed by 30 cycles of (20 seconds at 98° C., 30 seconds at 58° C. and two minutes plus 30 seconds at 72° C.) and ended by ten minutes at 72° C. The resulting fragments were purified using a QIAQUICK® PCR purification kit column (Qiagen) and digested with HindIII and XbaI. The digested fragments were then again purified over a QIAQUICK® PCR purification column as above and ligated with pAdApt35Bsu digested with the same enzymes and purified over a QIAQUICK® PCR purification column. Transformation into competent DH5a bacteria (Invitrogen) and selection of the clones containing the correct inserts using HindIII and XbaI as diagnostic enzymes results in pAdApt35Bsu.TB-L, pAdApt35Bsu.TB-S and pAdApt35Bsu.TB-FL. These constructs differ from the constructs presented in FIGS. 2, 3 and 4 in that they do not contain the myc epitope at the C-terminal end.

Construction of pAdApt35Bsu-Based Adapter Plasmids Containing Two TB Antigens

Here, the construction of adapter plasmids containing two TB antigens using Ag85A and Ag85B as an example is also described. Obvious to the person with general skill in the art, other combinations and a different order of *M. tuberculosis* antigens can be made using the general strategy outlined herein. The fusions that are described here are TB-3M: ALV-dig*-Ag85A-dig-Ag85B-myc and TB-4M: Ag85A-Ag85B-myc, and the same constructs without the myc-tag. Specific primers were designed to amplify the Ag85A and Ag85B sequences from the above described TB-LM and TB-SM fusion proteins (see below). Fusions are generated with and without (TB-3 and TB-4, respectively) myc-tag as above. Hereto, different primer sets and templates are used.

Fragment TB.3M:
ALVprot.FW and 85B.RE myc: (SEQ ID NO:13) with TB-LM as template.

Fragment TB.4M:
85A.FW.TB.L: (SEQ ID NO:14) and 85B.RE myc (see above) with TB-SM as template.

Figure 5:
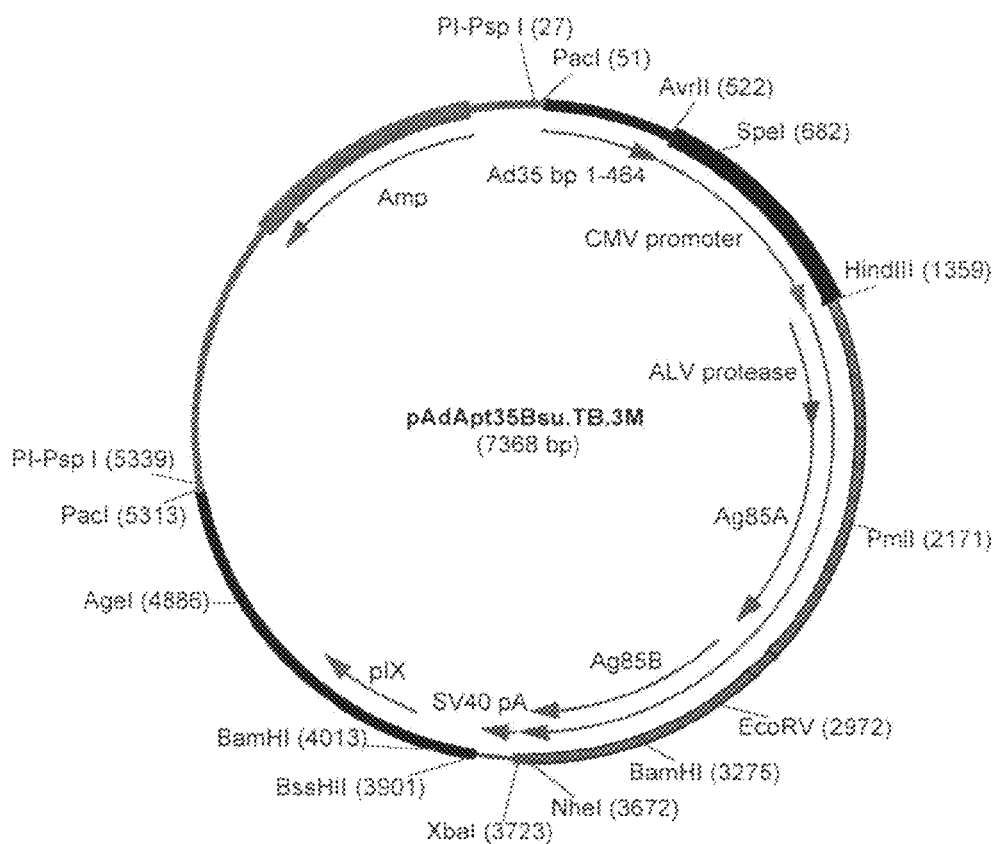
FIG. 5: Map of pAdApt35Bsu.TB.3M.
Figure 6:
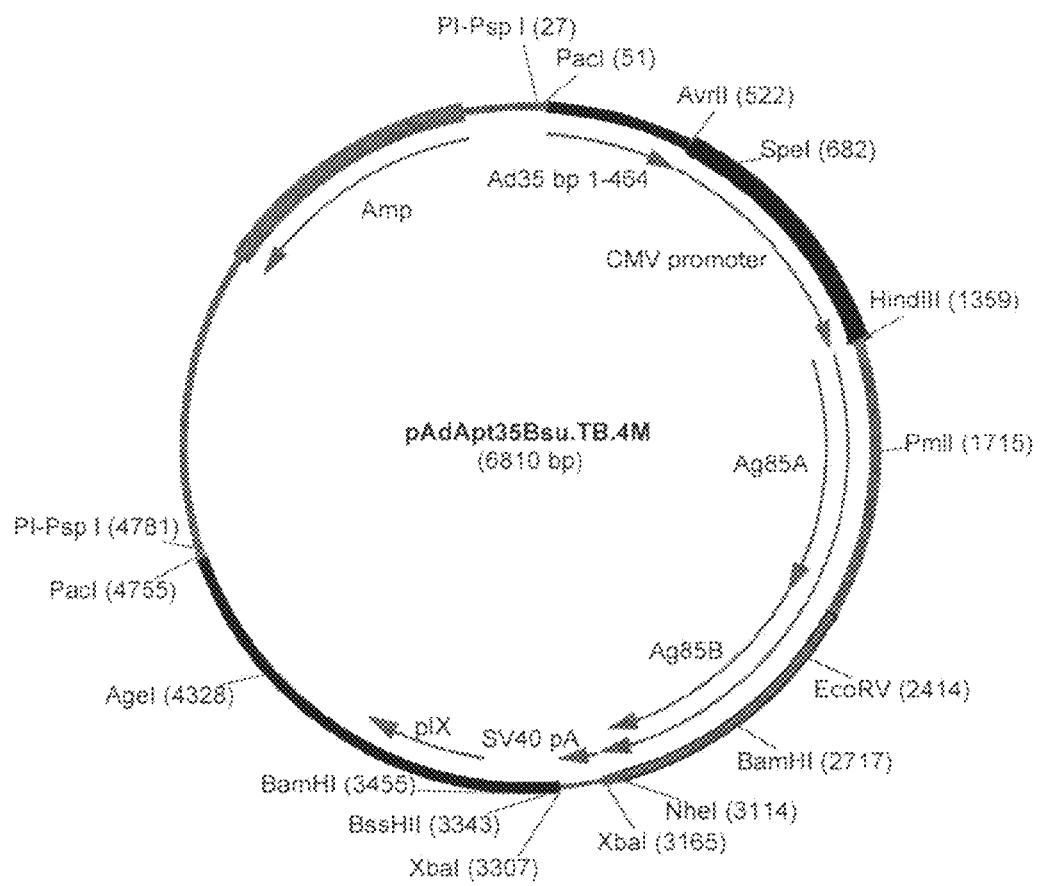
FIG. 6: Map of pAdApt35Bsu.TB.4M.

All reactions were done using PHUSION® (Bioke) DNA polymerase with the conditions as described above. PCR fragments were purified using a QIAQUICK® PCR purification kit column, digested with HindIII and NheI and again purified using the PCR purification kit. The amplified fragments were subsequently ligated into plasmid pAdApt35Bsu.myc that was digested with the same enzymes. After transformation into competent DH5α bacteria (Invitrogen), clones were selected that contained an insert of the correct length. This resulted in constructs pAdApt35Bsu.TB.3M (FIG. 5) and pAdApt35Bsu.TB.4M (FIG. 6).

Fragments TB.3 and TB.4 were generated using the same forward primers and templates indicated above for fragments TB.3M and TB.4M but using a different reverse primer named 85B.RE.stop: (SEQ ID NO:15). Amplified fragments were purified as above, digested with HindIII and XbaI, and again purified as described intra and cloned into pAdApt35Bsu using HindIII and XbaI as cloning sites. This gave pAdApt35Bsu.TB.3 and pAdApt35Bsu.TB.4 that only differ from the constructs in FIGS. 5 and 6 in that they have no myc-epitope at the C-terminus.

Other combinations that may be useful but not described in detailed cloning procedures herein are:
 ALV-dig*-Ag85B-dig-Ag85A-myc
 ALV-dig*-Ag85A-dig-TB10.4-dig-Ag85B-myc
 ALV-dig*-TB10.4-dig-Ag85A-dig-Ag85B-myc
 ALV-dig*-TB10.4-dig-Ag85B-dig-Ag85A-myc
 ALV-dig*-Ag85B-dig-Ag85A-dig-TB10.4-myc
 ALV-dig*-Ag85B-dig-TB10.4-dig-Ag85A-myc
 ALV-dig*-Ag85A-dig-TB10.4-myc
 ALV-dig*-Ag85B-dig-TB10.4-myc
 ALV-dig*-TB10.4-dig-Ag85A-myc
 ALV-dig*-TB10.4-dig-Ag85B-myc
 Ag85B-Ag84A-myc
 Ag85A-TB10.4-myc
 Ag85B-TB10.4-myc
 TB10.4-Ag85A-myc
 TB10.4-Ag85B-myc
 Ag85A-X-Ag85B-myc
 Ag85B-X-Ag85A-myc
 Ag85A-X-TB10.4-myc
 Ag85B-X-TB10.4-myc
 TB10.4-X-Ag85A-myc
 TB10.4-X-Ag85B-myc
 Ag85A-X-TB10.4-X-Ag85B-myc
 Ag85B-X-Ag85A-X-TB10.4-myc
 Ag85B-X-TB10.4-X-Ag85A-myc
 TB10.4-X-Ag85A-X-Ag85B-myc
 TB10.4-X-Ag85B-X-Ag85A-myc Dig*, dig, myc and X all relate to the same features as outlined above. It is to be understood that these constructs may also be produced without the myc-tag.

Construction of pAdApt35Bsu-Based Adapter Plasmids Containing Single TB Antigens Here, the Ad35 adapter plasmids containing single TB antigens are also described. As above, proteins are expressed with or without myc-tag. Hereto, the appropriate coding regions were amplified from the TB-L and TB-S templates using specific primers sets:
 Fragment TB.5M:
  85A.FW.TB.L and 85A.RE myc: (SEQ ID NO:16) using TB-LM as template.
 Fragment TB.6M:
  85B.FW: (SEQ ID NO:17) and 85B.RE myc using TB-LM as template.
 Fragment TB.7M:
  10.4.FW: (SEQ ID NO:18) and 10.4.RE myc: (SEQ ID NO:19) using TB-LM as template.

Figure 7:
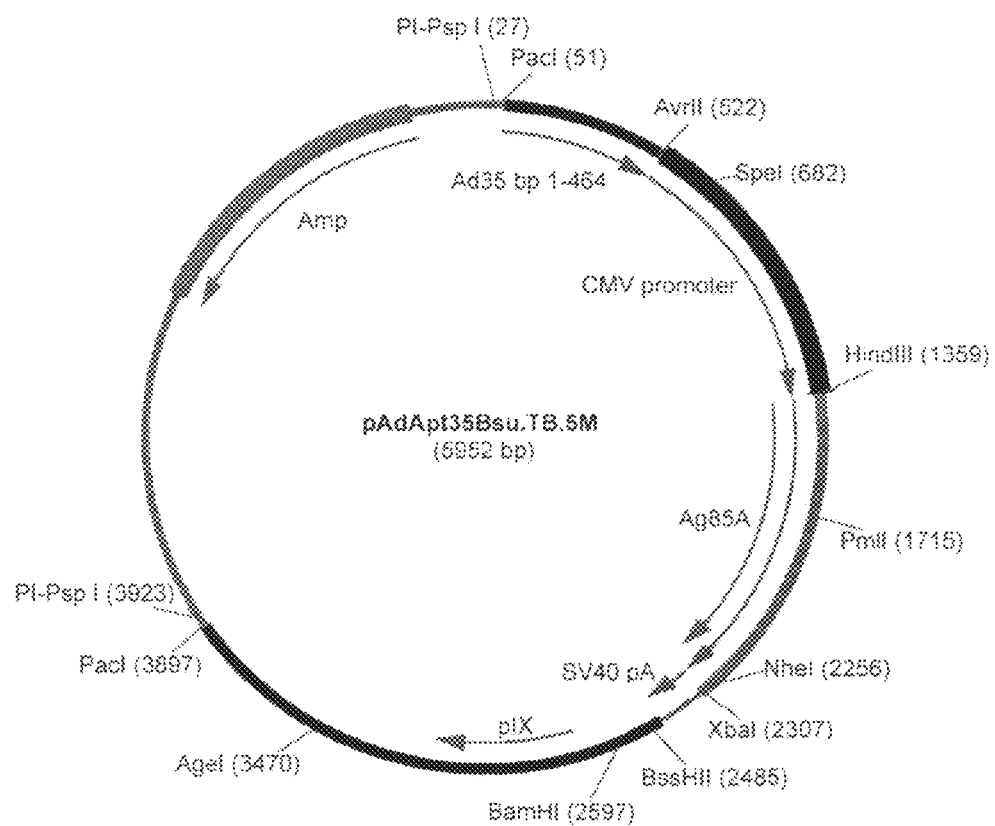
FIG. 7: Map of pAdApt35Bsu.TB.5M.
Figure 8:
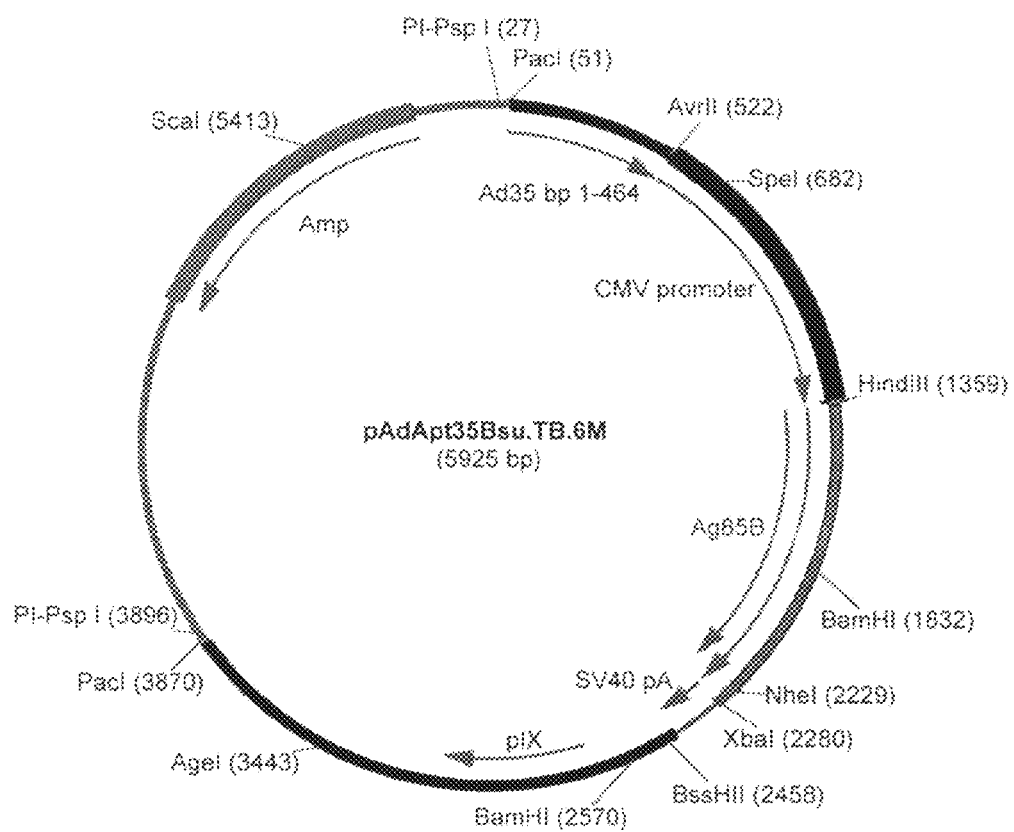
FIG. 8: Map of pAdApt35Bsu.TB.6M.
Figure 9:
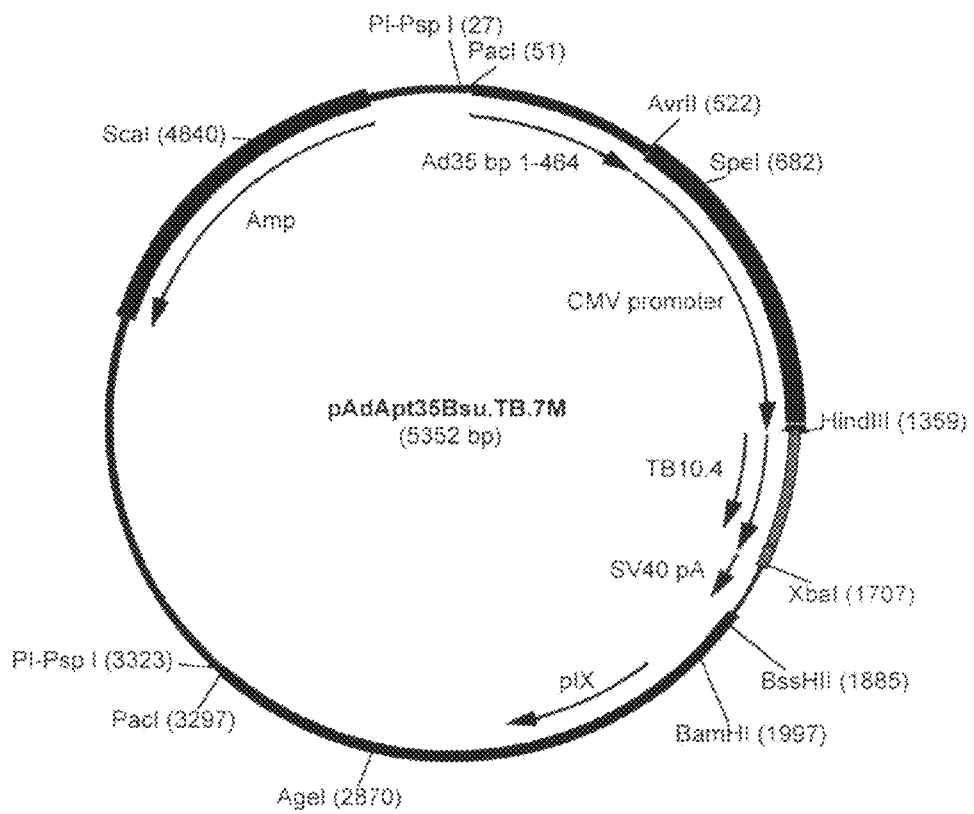
FIG. 9: Map of pAdApt35Bsu.TB.7M.

The fragments without myc-tag were generated with the same forward primers but with different reverse primers: 85A.RE.stop (for TB.5): (SEQ ID NO:20), 85B.RE.stop (for TB.6), and 10.4.RE.stop (for TB.7). All reactions were done with PHUSION® DNA polymerase (Bioke) as described above. All amplified fragments were purified using the QIAQUICK® PCR purification kit. The fragments TB-5M and TB-6M were then digested with HindIII and NheI and after purification as described above, cloned into pAdApt35Bsu.myc digested with the same enzymes. The fragments TB-7M, TB-5, TB-6 and TB-7 were digested with HindIII and XbaI. After purification as above, fragments were ligated into pAdApt35Bsu digested with the indicated restriction enzymes. This resulted in pAdApt35Bsu.TB.5M (FIG. 7), pAdApt35Bsu.TB.6M (FIG. 8), pAdApt35Bsu.TB.7M (FIG. 9), pAdApt35B su.TB.5, pAdApt35Bsu.TB.6 and pAdApt35Bsu.TB.7. The latter three differ only from the ones in FIGS. 7, 8 and 9 in that no myc-tag is present at the C-terminus.

Example 2

Generation of Replication-Deficient Ad35 Viruses Carrying Nucleic Acids Encoding TB Antigens Methods to generate stable replication defective recombinant Ad35 based adenoviral vectors carrying heterologous expression cassettes are well known to the person of skill in the art and were previously described in published patent applications WO 00/70071, WO 02/40665, WO 03/104467 and WO 2004/001032. This example describes the generation of Ad35 based TB vectors using PER.C6® human embryonic retinoblast cells and Ad35 viruses comprising the Ad5 derived E4 Orf6 and E4 Orf6/7 genes replacing the homologous E4 Orf6 and 6/7 sequences in the Ad35 backbone (generally as described in WO 03/104467 and WO 2004/001032). For the purposes of the invention, PER.C6® human embryonic retinoblast cells refer to cells as deposited on Feb. 29, 1996, as patent deposit under no. 96022940 at the European Collection of Cell Cultures (ECACC) at the Centre of Applied Microbiology & Research (CAMR), Porton Down, Salisbury, Wiltshire, SP4 0JG United Kingdom.

The generated adapter plasmids described herein, containing the different TB antigens were digested with Pi-PspI to liberate the Ad35 sequences and transgene cassette (adapter fragment) from the plasmid backbone. Construct pWE.Ad35.pIX-EcoRV (see WO 03/104467 and WO 2004/001032) was digested with NotI and EcoRV (fragment 2) and construct pBr.Ad35.ΔE3.PR5Orf6 (see WO 03/104467 and WO 2004/001032) was digested with PacI and NotI (fragment 3). The digested DNA mixes were incubated at 65° C. to inactivate the enzymes.

For each transfection, digested adapter fragment (360 ng), fragment 2 (1.4 µg) and fragment 3 (1 µg) were mixed to a (maximum) volume of 15 µl and adjusted to 25 µl with DMEM (culture medium, Invitrogen). A second mixture was prepared by mixing 14.4 µl LIPOFECTAMINE™ reagent (Invitrogen) with 10.6 µl DMEM, after which the two mixes were added together and mixed by tapping the tube. The resulting DNA Lipofectamine mixture was then incubated 30 to 40 minutes at room temperature after which 4.5 ml DMEM was added to the tube. During incubation, PER.C6® human embryonic retinoblast cells that were seeded the day before in six well plates at 1.5×106 cells/well in DMEM containing 10% FBS (Invitrogen/GIBCO) and 10 mM $MgCl_2$, were washed with DMEM. Then, to the first two wells, 0.5 ml DMEM was added and 0.5 ml of the incubated transfection mixture. To the second two wells, 0.25 ml medium and 0.75 ml of the transfection mixture was added.

The last two wells received 1 ml of the transfection mixture. The six well plate was then incubated at 37 C and 10% CO2 for four hours after which an agar overlay was placed as follows. Thirty minutes before the end of the four hour incubation period, a mixture containing 9 ml 2×MEM (Invitrogen), 0.36 ml FBS, 0.18 ml 1M $MgCl_2$ and 1.3 ml PBS was prepared and placed at 37 C. A sterile pre made solution of 2.5% agarose (SEAPLAQUE® agarose; Cambrex) in $H_2O$ was melted and also kept at 37 C (at least 15 minutes prior to use). The transfection medium was then removed from the cells and cells were washed with PBS once. Then, 7.5 ml of the agar solution was added to the MEM medium mixture, mixed and 3 ml was quickly added to each well. The overlay was allowed to coagulate in the flow after which the plates were incubated at 37 C/10% $CO_2$ for at least seven days. When large enough, single plaques were picked from the wells with the lowest number of plaques using pipettes with sterile filter tips (20 µl). The picked plaques were mixed in 200 µl culture medium each and 100 µl of this was used to inoculate PER.C6® human embryonic retinoblast cells in six well plates. Upon CPE and after one more amplification of the viruses on PER.C6®, human embryonic retinoblast cells in T25 flasks cells and medium were harvested and freeze/ thawed once and stored as crude lysates. These virus stocks were used to confirm the presence of the correct transgene by PCR on isolated virus DNA and to test expression. One of the amplified plaques was then chosen to generate virus seed stocks and to produce batches of purified virus according to procedures known in the art using a two step CsCl purification method. The concentration of purified viruses was typically determined by HPLC as described by Shabram et al. (1997).

Example 3

Analysis of Expression of TB Antigens Upon Infection with Ad35 Viral Vectors

The expression of the fused TB antigens was determined by western blotting. Hereto, A549 cells were infected with the different Ad35 viruses containing the genes encoding the TB antigens. Forty-eight hours post infection, cells were washed twice with PBS (NPBI), lysed and scraped in lysis buffer (20 mM Tris-HCl pH 7.5, 150 mM NaCl, 0.5% DOC, 1% TWEEN®-20 in $dH_2O$ supplemented with 1% SDS and Protease inhibitor added as a pill (Roche)). After five to ten minutes in lysis buffer on ice, lysates were collected and cleared by centrifugation. Equal amounts of whole-cell extract were fractionated by using 4-12% Bis-Tris NuPAGE® Pre-Cast Gels (Invitrogen). Proteins were transferred onto Immobilon-P membranes (Millipore) and incubated with a polyclonal antibody directed to the Culture Filtrate Protein of *M. tuberculosis*. This polyclonal serum was raised in rabbits against an *M. tuberculosis* culture comprising secreted proteins. In principle, the polyclonal serum contains antibodies against Ag85A, Ag85B and TB10.4, which are all secreted proteins. The secondary antibody was a horseradish-peroxidase-conjugated goat-anti-rabbit antibody (Biorad). The western blotting procedure and incubations were performed according to general methods known in the art. The complexes were visualized with the ECL detection system (Amersham) according to the manufacturer's protocol.

Figure 10A:
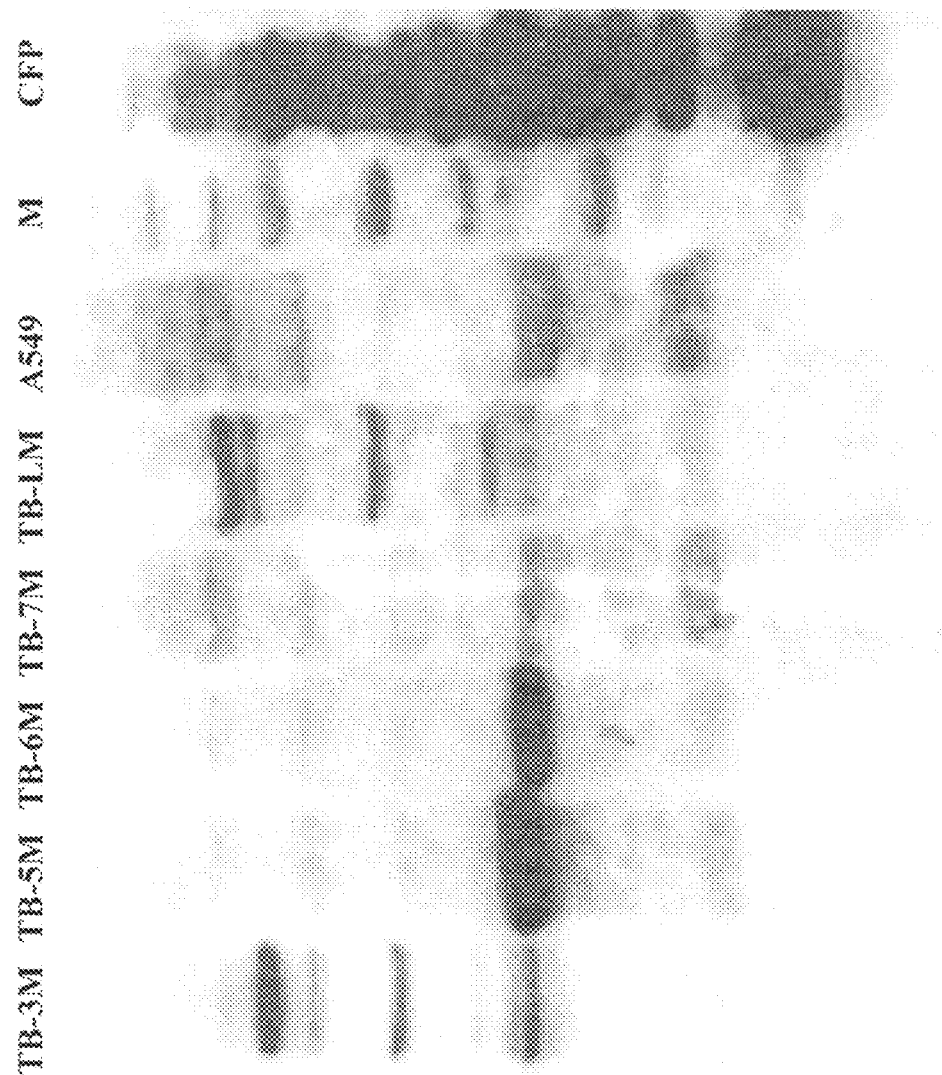
FIG. 10: Western blot with anti-TB antigen polyclonal on lysates from A549 cells infected with Ad35 viruses comprising nucleic acids encoding different sets of TB antigens with the myc-tag (FIG. 10A) and without the myc-tag (FIG. 10B).
FIG. 10C is similar to FIG. 10B, with molecular weight markers. See for notation Table I.
Figure 10B:
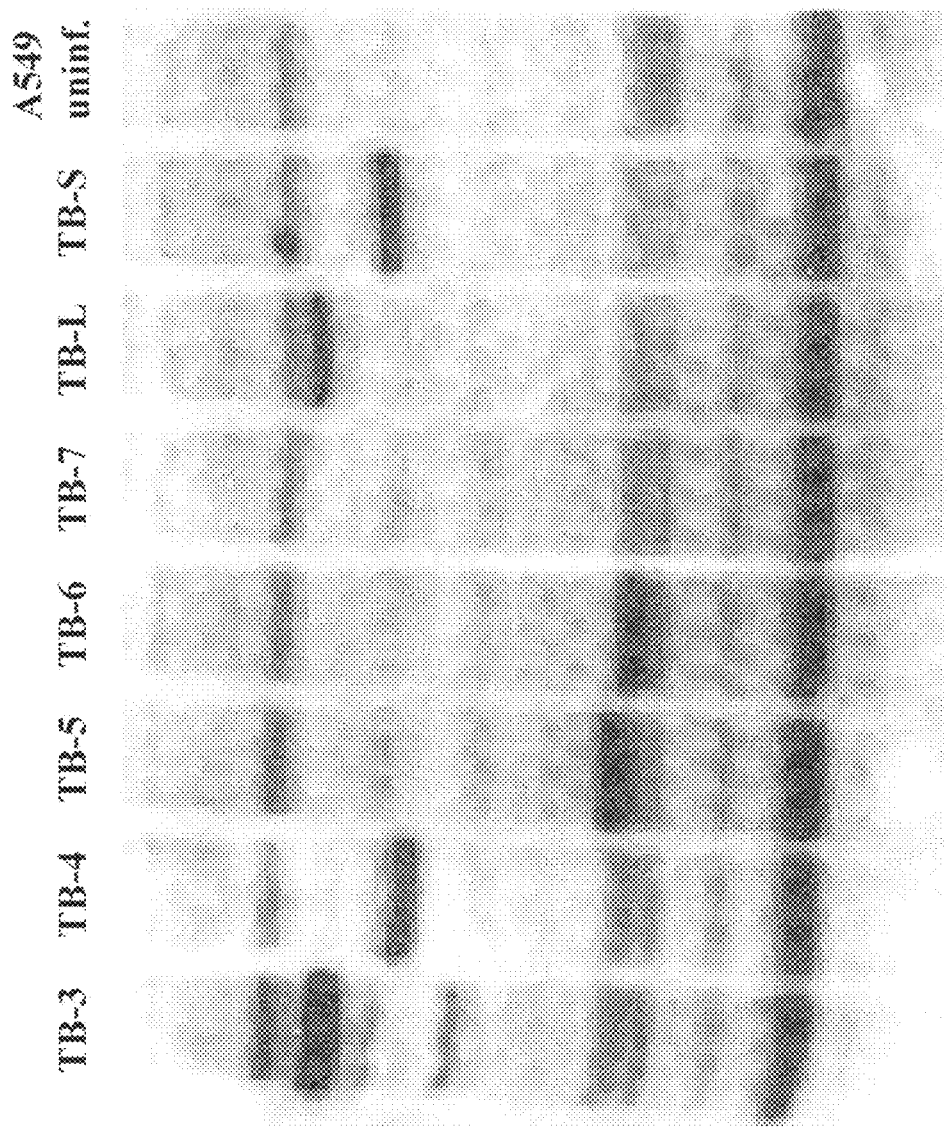
Figure 10C:
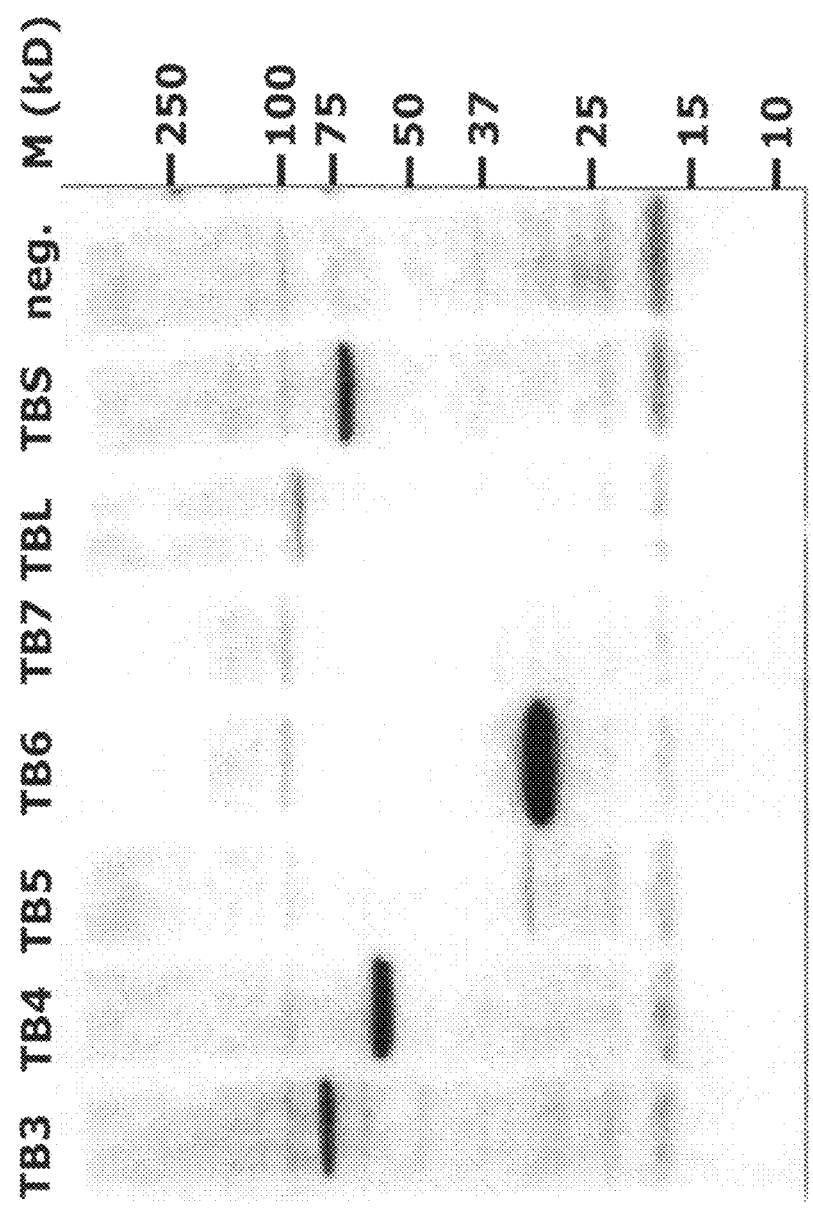

FIG. 10A shows the results using Ad35 viruses carrying the TB-encoding nucleic acids including the myc epitope as described herein. The different lanes in FIG. 10A show the different viral vectors used and Table I indicates which name refers to what insert. In the same way, expression of the TB antigens from the Ad35 viruses that do not contain a myc epitope was measured (FIG. 10B). FIG. 10C shows a similar result, with the molecular weight indicated on the right-hand side. Specific TB (fusion) proteins expressed from Ad35 viruses are detected by this method and, in addition, certain cleavage products of TB-3 and TB-L. From FIG. 10A it can be concluded that the polyprotein including all three TB antigens is expressed, since a higher band in lane TB-LM is present as compared to TB-3M (and the band in lane TB-S is higher than the specific band in TB-4M). Since the TB10.4 is the most C-terminal polypeptide in the TB-LM and TB-SM polyproteins, this indicates that the entire polyproteins are translated. It is also noted that cleavage is not complete, although cleavage products can be seen in lanes TB-3M and TB-LM. The Ag85A and Ag85B antigens (lanes TB-5(M) and TB-6(M), respectively) are expressed. No specific staining is found in lanes TB-7(M) related to the TB10.4 antigen. It may be that the antigen is not recognized in a western blot setting by the CFP polyclonal, whereas it may also be that the protein has run from the gel or that is poorly expressed in A549 cells when present in a single expression construct (TB-7M), while present in a triple construct (as TB-LM, TB-L and TB-S). In FIG. 10A, lane TB-LM, a slightly shorter band is visible under the highest (probably non-cleaved) band. This suggests cleavage of the TB10.4 antigen from the remaining portion of the polyprotein.

Further experiments should reveal the physical presence of the protein, although it is clear that the TB10.4 antigen contributes to the immune response (see below), strongly indicating that the antigen is present and actively involved in the immune response.

Example 4

Immunogenicity of Vectors Encoding *M. Tuberculosis* Antigens in Mice

First, the immunogenicity of the adapter plasmids as described in Example 1 (DNA constructs) was studied in mice. The constructs encoded one, two or three TB antigens: Ag85A, Ag85B and TB10.4. The DNA constructs encoding for the multiple TB antigens were designed in two ways as described above, i.e., expressing a polyprotein comprising direct fusions not containing the myc tag and expressing a polyprotein comprising a sequence encoding a protease and the protease recognition sites resulting in the cleavage of the polyprotein (also not containing the myc tag) into discrete polypeptides. The following DNA constructs were used (see Example 1):

Single antigen constructs
TB-5 (Ag85A), TB-6 (Ag85B) and TB-7 (TB10.4)
Double antigen constructs
TB-3 (ALV-dig*-Ag85A-dig-Ag85B) and TB-4 (Ag85A-Ag85B direct fusion)
Triple antigen constructs
TB-L (ALV-dig*-Ag85A-dig-Ag85B-dig-TB10.4) and TB-S (Ag85A-Ag85B-TB10.4 direct fusion).

Figure 11:
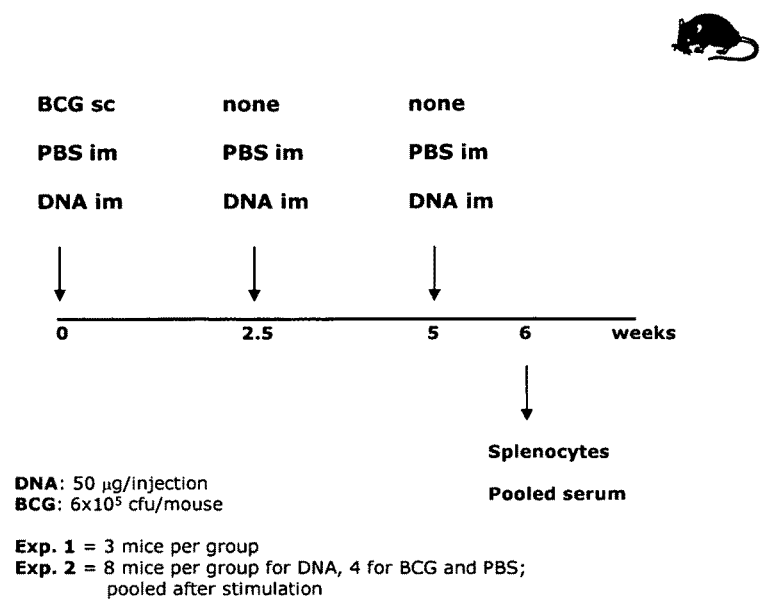
FIG. 11: Experimental design of immunization protocol using seven different adenoviral vectors (DNA) harboring different sets of nucleic acids encoding tuberculosis antigens.

The experimental set up is given in FIG. 11. Seven groups of mice were immunized with individual TB DNA constructs (two experiments, see below). For each immunization, DNA was injected intramuscularly three times (3×50 µg) with intervals of 2.5 weeks. As a negative control, one group of mice received three injections of PBS. Additional control group received single dose of $6 \times 10^5$ cfu BCG (strain SSI1331) subcutaneously.

One week after the last DNA immunization and six weeks after the BCG immunization, the mice were sacrificed. Spleens were isolated to serve as a source of cells for cellular immunological assays. Sera, required for humoral response analysis, were collected by heart punction and pooled per group.

The level of specific cellular immune response was determined using intracellular IFNγ staining (ICS) FACS assay, by measuring the frequency of IFNγ+ CD4+ and IFNγ+ CD8+ splenocytes after in vitro re-stimulation with peptide pools of corresponding antigens. The immune sera were tested using immunofluorescence of A549 cells transduced with adenovirus encoding for corresponding antigen.

Two independent immunization experiments were performed. For the first experiment, three mice per group were used and the immune response was analyzed for each mouse individually. For the second experiment, eight mice per group were used for DNA immunizations and four mice per group for control immunizations. After in vitro stimulation with peptides, samples of two-by-two mice from the same group were pooled and stained for FACS analysis. Similar results were obtained in both experiments and the data were brought together for statistical analysis.

The intracellular IFNγ staining (ICS) was performed as follows. Splenocytes ($10^6$ per well of 96-well plate) were stimulated in duplicate with appropriate peptide pool as indicated (final concentration 2 μg/ml per peptide), in the presence of co-stimulatory antibodies: anti-mouse-CD49d and anti-mouse-CD28 (Pharmingen) in a final dilution of 1:1000. Peptide pools consisted of 15-mer peptides spanning whole antigens, with 10-mer (Ag84B) or 11-mer (Ag85A, TB10.4) overlapping sequences, or adjusted for Ag85B with peptide p1 and p2 from Ag85A, as outlined below in Examples 6 and 7.

Samples from BCG- and PBS-immunized mice were stimulated additionally with CFP (Culture Filtrate Protein; final concentration 10 μg/ml) and PPD (Purified Protein Derivative; final concentration 10 μg/ml), which are antigens commonly used for in vitro stimulation upon BCG immunization. As a positive control, samples were stimulated with PMA/ionomycin (final concentrations: 50 ng/ml and 2 μg/ml, respectively), whereas the incubation with medium served as a negative control (no stimulation). After one-hour stimulation at 37° C., secretion blocker GolgiPlug was added (Pharmingen; final dilution 1:200) and the incubation was continued for an additional time period of five hours. The corresponding duplicate samples were pooled and processed for FACS analysis. Briefly, cells were washed with PBS containing 0.5% BSA and incubated with FcR Blocker (Pharmingen; dilution 1:50) for ten minutes on ice. After a washing step, the cells were incubated with CD4-FITC (Pharmingen; dilution 1:250) and CD8-APC (Pharmingen; dilution 1:50) for 30 minutes on ice. Upon washing, cells were fixed and permabilized with Cytofix/Cytoperm (Pharmingen) for 20 minutes on ice, followed by a washing step with Perm/Wash buffer (Pharmingen). Intracellular IFNγ was stained using anti-IFNγ-PE (Pharmingen; dilution 1:100) for 30 minutes on ice.

After final washing steps, cells were resuspended in CellFix (BD) and analyzed using flow cytometer. At least 10,000 CD8+ cells were measured for each individual sample. Results are expressed as a percentage of CD4+ or CD8+ cells that express IFNγ.

An overview of the in vitro re-stimulation samples is given in Table II. The results of the ICS are presented in FIGS. 12-16.

FIG. 12, Panels A and B, show that background levels were very low when the cells were not stimulated. FIG. 13, Panel A, shows a high frequency of IFNγ+ CD4+ splenocytes after stimulation with peptides of the Ag85A pool. There is a clear cross-reactivity with CD4+ cells obtained from mice injected with the construct harboring the Ag85B encoding gene, which is not unexpected due to the high structural homology between Ag85A and Ag85B. In contrast to what was found for CD4+ cells, no stimulation of CD8+ splenocytes (see FIG. 13, Panel B) was detected of cells from mice injected with constructs encoding either Ag85A alone or in the context of Ag85B (lanes Ag85A, Ag85B, TB-3L and TB-4S). However, there was a striking increase in IFNγ+ CD8+ splenocytes in mice injected with the triple constructs TB-L and TB-S, clearly indicating an important role of the additional antigen (TB10.4) present in these constructs. Apparently, in this setting, the TB10.4 antigen is able to strongly increase the frequency of CD8+ splenocytes reactive towards the Ag85A peptides, where Ag85A alone (or in combination with Ag85B) provides no responses.

FIG. 14, Panel A shows that Ag85B in all settings in which it was present is able to increase the frequency of IFNγ+ CD4+ splenocytes, whereas the effect on IFNγ+ CD8+ splenocytes is minimal (see FIG. 14, Panel B). Also here, cross-reactivity is found between Ag85B and Ag85A (FIG. 14, Panel A) as discussed above. FIG. 15, Panel A shows that the frequency of IFNγ+ CD4+ splenocytes responding to the TB10.4 related peptide pool is present, where no real difference can be found between mice injected with either a construct with TB10.4 alone or a construct comprising the triple inserts. However, as shown in FIG. 15, Panel B, the frequency of IFNγ+ CD8+ splenocytes from mice that were injected with constructs comprising the gene encoding the TB10.4 antigen, is dramatically increased upon stimulation with TB10.4 related peptides, especially in the context of the triple inserts (Note the y-axis, indicating that an average of 1.5% of the splenocytes was reactive).

The results are summarized in FIG. 16, Panel A (triple insert in TB-L: with protease and protease digestion sites) and FIG. 16, Panel B (TB-S: direct-linked antigens). Clearly, the different antigens contribute in different manners to the immune response: Ag85A induces both CD4 and CD8 responses; Ag85B only induces a strong CD4 response and hardly any CD8 response. In contrast to Ag85B, the TB10.4 antigen invokes a strong CD8 response and a minor CD4 response. This indicates the clear beneficial subsidiary effect of the different antigens encoded by the sequences present in the triple inserts.

The BCG immunization did not result in significant ICS response. However, splenocytes of BCG-immunized mice

TABLE II

Overview of the in vitro re-stimulation samples.

| Immunization | In vitro antigen stimulation | | | | | | |
| --- | --- | --- | --- | --- | --- | --- | --- |
| | Ad85A | Ad85B | TB10.4 | CFP | PPD | PMA | Medium |
| Ad85A (TB-5) | X | X | | | | X | X |
| Ad85B (TB-6) | X | X | | | | X | X |
| TB10.4 (TB-7) | | | X | | | X | X |
| Ad85A.Ad85B (TB-3) | X | X | | | | X | X |
| Ad85A.Ad85B (TB-4) | X | X | | | | X | X |
| Ad85A.Ad85B.TB10.4 (TB-L) | X | X | X | | | X | X |
| Ad85A.Ad85B.TB10.4 (TB-S) | X | X | X | | | X | X |
| BCG | X | X | X | X | X | X | X |
| PBS | X | X | X | X | X | X | X | did produce high levels of IFNγ after 72 hours stimulation with CFP or PPD, as determined using an IFNγ ELISA kit, which indicates that mice were immunized efficiently (data not shown).

To determine whether any antigen-specific antibodies were actually raised in the mice injected with the different DNA constructs, A549 cells were transduced with Ad35 recombinant adenoviruses encoding the TB antigens in 96-well plates. The adenoviruses were produced as described in Example 2. For this, $1 \times 10^4$ cells were seeded per well and viruses were infected with a multiplicity of infection of 5000. Two days after infection, cells were fixed with Cytofix/Cytoperm (20 minutes at 4° C.), followed by a washing step with Perm/Wash buffer. Cells were incubated with immunized mice sera, diluted 1:2 in Perm/Wash buffer, for one hour at 37° C. Upon washing, goat anti-mouse-FITC, diluted 1:5 in Perm/Wash buffer, was added and incubated for 30 minutes at 37° C. After a final wash, cells were analyzed using a fluorescence microscope.

The immunofluorescence analysis revealed strong antigen-specific staining of cells with sera obtained from mice immunized with TB-6 (Ag85B alone), TB-3 (ALV-dig*-Ag85A-dig-Ag85B), TB-4 (Ag85A-Ag85B direct fusion) and TB-L (ALV-dig*-Ag85A-dig-Ag85B-dig-TB10.4). Weak staining was observed with sera from mice immunized with TB-S (Ag85A-Ag85B-TB10.4 direct fusion), while sera obtained upon immunization with TB-5 (Ag85A alone) and TB-7 (TB10.4 alone), did not exhibit any staining. This indicates that at least some of the antigens are able to elicit an antibody response. Full cleavage of the protease from the remaining part of the polyprotein and expression levels of the separate antigens was not determined in this experiment.

Example 5

Construction of rAd Vectors Encoding an Antigen and an Adjuvant

Here, a novel recombinant replication-defective adenoviral vector is constructed, herein designated Ad35-X-A1$_{K63}$, which co-expresses an antigen (referred to as X) and a mutant derivative of CtxA1 that harbors a lysine substitution at amino acid no. 63 (i.e., herein referred to as $A1_{K63}$) in place of the serine that is present in the parental CtxA1.

The construction of adapter plasmids suitable to generate E1-deleted Ad35-based vectors capable of expressing X and $A1_{K63}$ is achieved by introducing PCR-amplified X using standard PCR procedures known to persons skilled in the art, and introducing appropriate cloning restriction sites. The resultant PCR-generated DNA fragment is digested with the respective restriction endonuclease(s) and annealed to an adapter plasmid generally as described above for Ag85A, Ag85 and TB10.4. Additional analysis by restriction endonuclease digestion, PCR and sequencing of the cloned PCR fragment are conducted to verify that the DNA was not altered during construction.

DNA encoding $A1_{K63}$ is amplified from plasmid pOGL1-A comprising a copy of CtxA1. The nucleotide sequence of ctxA1 is available in GenBank (Accession #A16422) and modified by replacing the serine-63 TCA codon (nt 187-189) with a lysine codon AAA. The mutant derivative is generated using the QuikChange® Site-Directed Mutagenesis Kit (Stratagene). The site-directed mutagenesis process entails whole-plasmid PCR using pOGL1-A1 DNA as template, forward primer 5'-TGT TTC CCA CCA AAA TTA GTT TGA GAA GTG C-3' (SEQ ID NO:24) and reverse primer 5'-CAA ACT AAT TTT GGT GGA AAC ATA TCC ATC-3' (SEQ ID NO:25). This procedure modifies nucleotides 187-189 by replacing the TCA codon with an AAA codon (see underlined sequences). The resultant PCR-generated plasmid is digested with DpnI to remove the template DNA and the digested DNA is introduced into *E. coli* by chemical transformation and grown on agar at 30° C. for 16 hours. Isolated colonies are selected and DNA was extracted from overnight liquid cultures. Plasmid PCR using primers specific for $A1_{K63}$, and agarose gel electrophoresis are conducted to screen for an appropriate derivative. The mutant insert is cloned thereafter into the same adapter plasmid that contains X, either upstream or downstream of X and adenoviruses are produced as described above.

Example 6

Dose Response of Ad35.TB Vectors in Mice

Ad35-recombinant viruses expressing the different single and fused TB antigens were used to test antigenicity in mice. Methods to quantify T-cells that produce interferon-gamma (IFN-γ) after stimulation with proteins or peptide pools are typically performed using methods known in the art and, for example, described in WO 2004/037294, Sander et al. (1991) and Jung et al. (1993). Details are described below.

The triple insert vector TB-S was used in a dose-response immunogenicity test. Four different doses of viral particles ($10^7$, $10^8$, $10^9$ and $10^{10}$ vp) were injected intramuscularly in different groups of C57BL/6 mice (five mice per group), whereas three mice served as a negative control and were injected with $10^{10}$ vp of the empty viral vector. Two weeks after immunization, the mice were sacrificed and splenocytes were isolated to serve as the source of cells for cellular immunological studies. The level of antigen-specific cellular immune responses was determined using the intracellular IFNγ staining (ICS) FACS assay, by measuring the frequency of IFNγ CD4+ and CD8+ splenocytes as described above. The results are shown in FIG. 17. Clearly, the Ad35-based TB-S vector induces an antigen-specific immune response in a dose-dependent manner, especially in relation to the increase in response with Ag85B-specific CD4 cells (FIG. 17C). No response was found related to TB10.4-specific CD4 cells FIG. 17E), and no response was found related to Ag85B-specific CD8 cells (FIG. 17D). While hardly any responses were detected with the $10^7$ and $10^8$ doses in respect to Ag85A- and TB10.4-specific CD8 cells (FIGS. 17B and 17F, respectively), a marked increase was found using the $10^9$ and $10^{10}$ doses. The $10^7$ dose did not give any significant effects in any of the settings, while the $10^8$ dose also resulted in an increase in Ag85A- and Ag85B-specific CD4 cells (FIGS. 17A and 17C, respectively). Similar data were found using the TB-L construct (data not shown).

During an assessment for the CD8 immunodominant sequence epitope mapping of *M. tuberculosis* antigens in mice, it was found that the peptides referred to as p1 (FSRPGLPVEYLQVPS; SEQ ID NO:26) and p2 (GLPVEYLQVPSPSMG; SEQ ID NO:27) of Ag85A were the only CD8 immunodominant epitopes for C57BL/6 mice. The underlined stretch should theoretically fit in the MHC molecules of C57BL/6 mice. The sequence of the Ag85A antigen in this region of the protein (amino acids 1-19: FSRPGLPVEYLQVPSPSMG; SEQ ID NO:28) is identical to the sequence of Ag85B in the same region. However, the peptides p1 and p2 from the Ag85B pool, although comprised of the same sequence as peptides from Ag85A, did not give any CD8 response (see FIG. 17D). This suggests that the peptides p1 and p2 from Ag85B were not in order, perhaps due to production effects or contaminations.

Figure 17A:
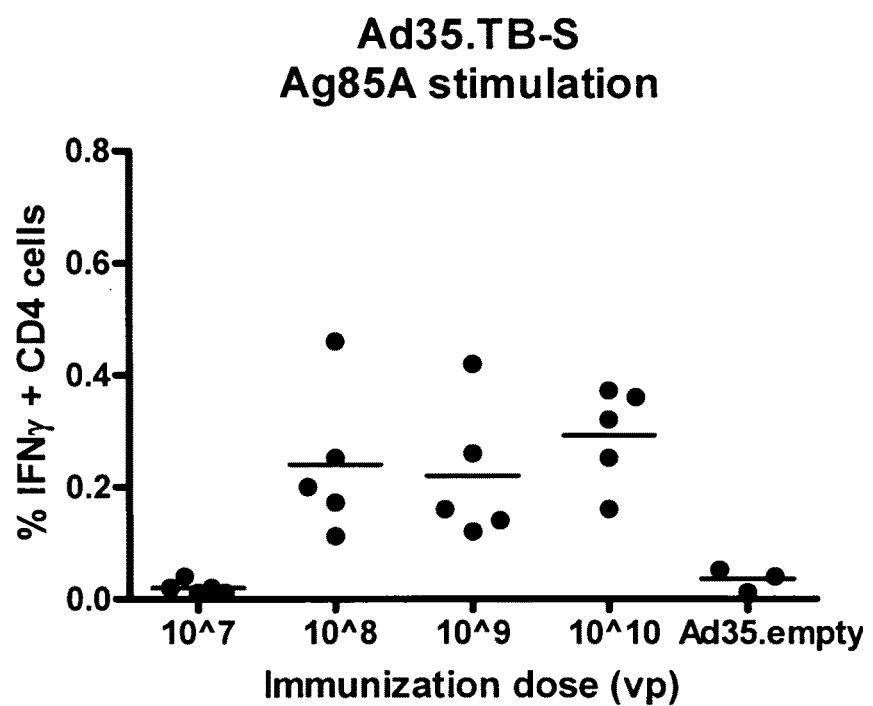
FIG. 17: Dose response effect using different doses of TB-S comprising a nucleic acid encoding Ag85A, Ag85B and Tb10.4 antigens. CD4 response towards Ag85A (FIG. 17A), Ag85B (FIG. 17C) and TB10.4 (FIG. 17E). CD8 response towards Ag85A (FIG. 17B), Ag85B (FIG. 17D) and TB10.4 (FIG. 17F).
FIG. 17G shows the CD8 response towards Ag85B with the adjusted peptide pool (see Example 6): left graph, upon TB-L infection; right graph, upon TB-S infection.
Figure 17B:
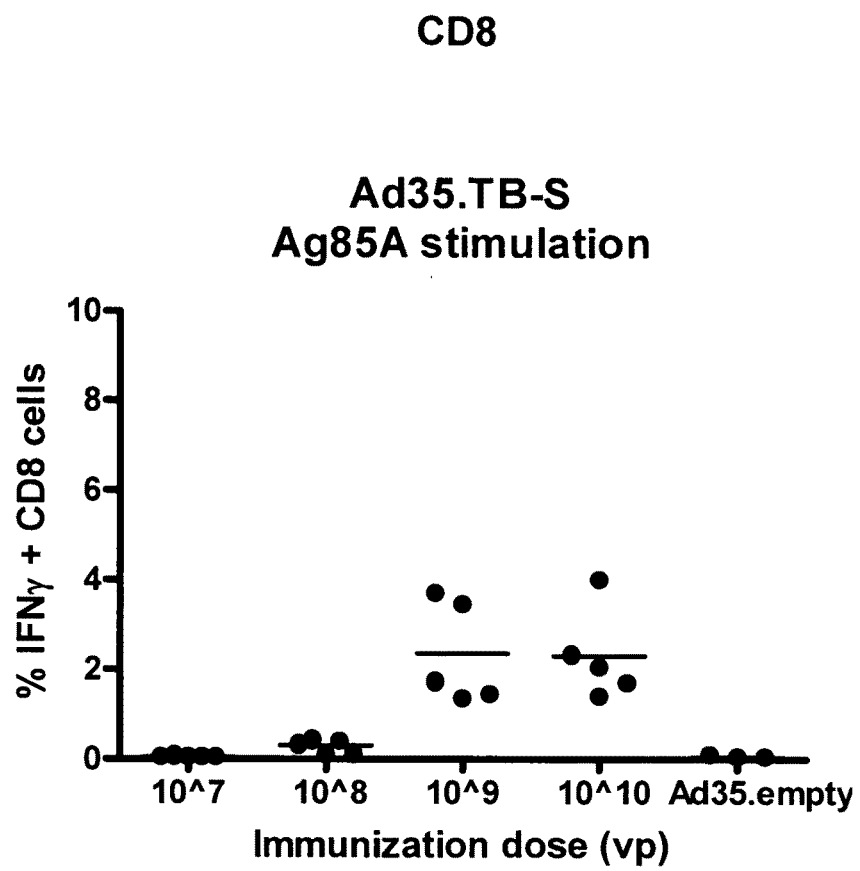
Figure 17C:
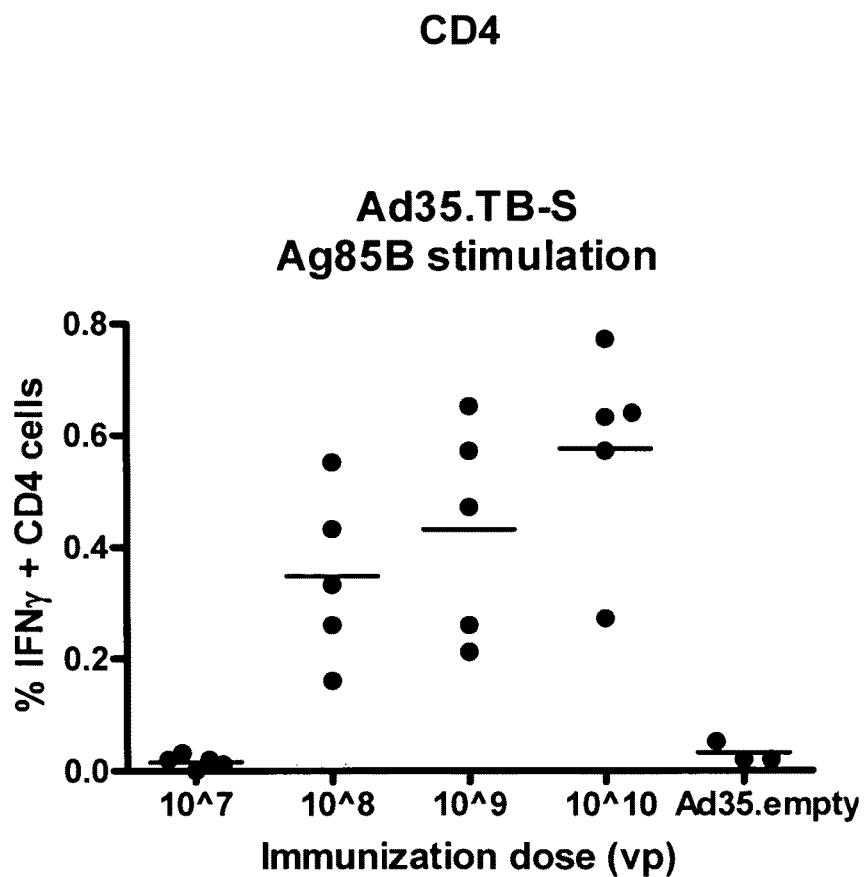
Figure 17D:
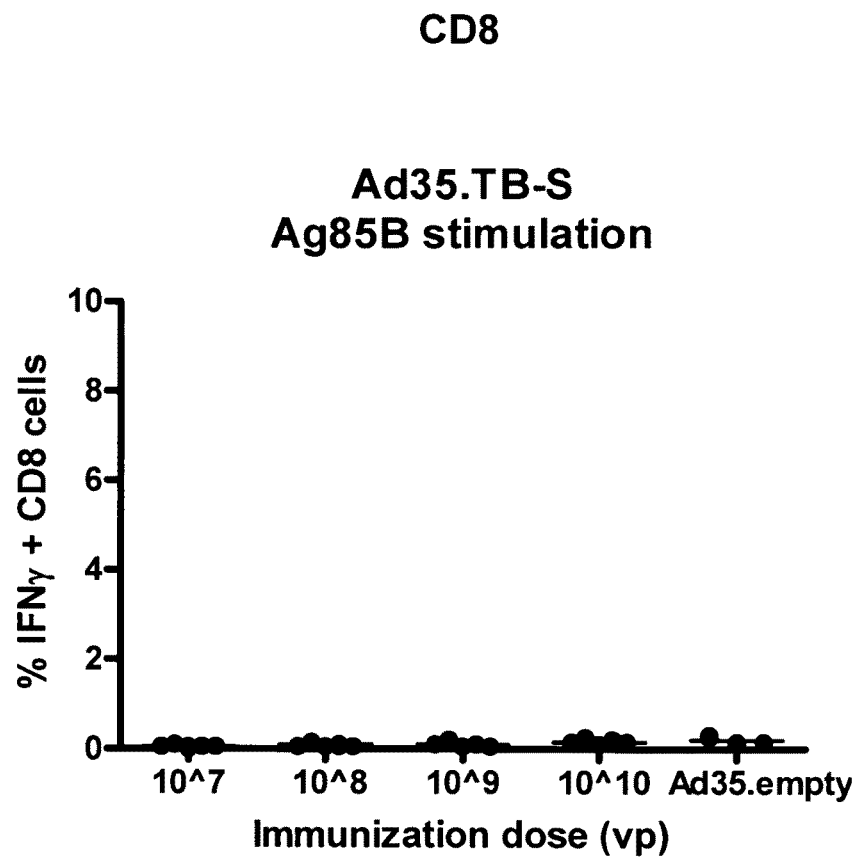
Figure 17E:
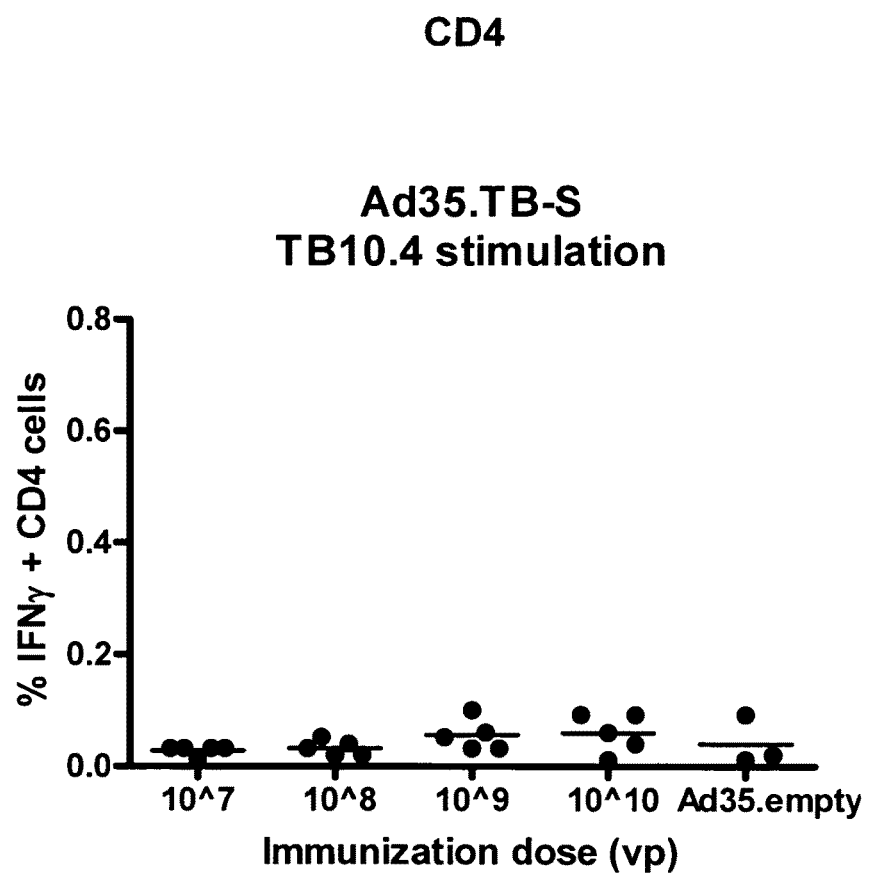
Figure 17F:
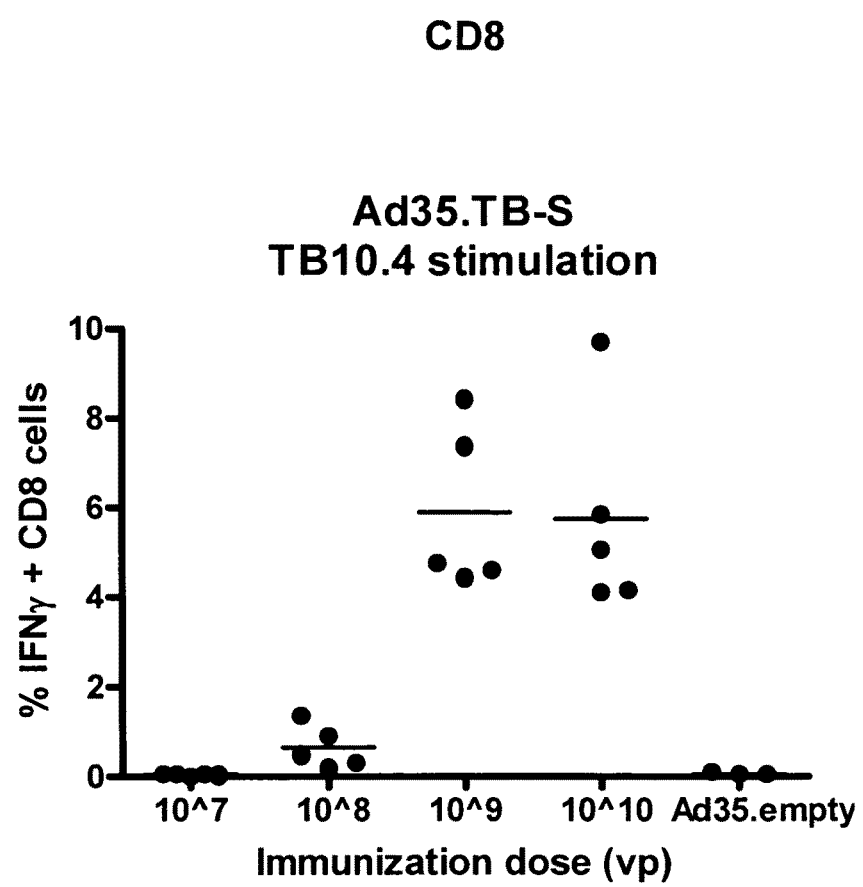
Figure 17G:
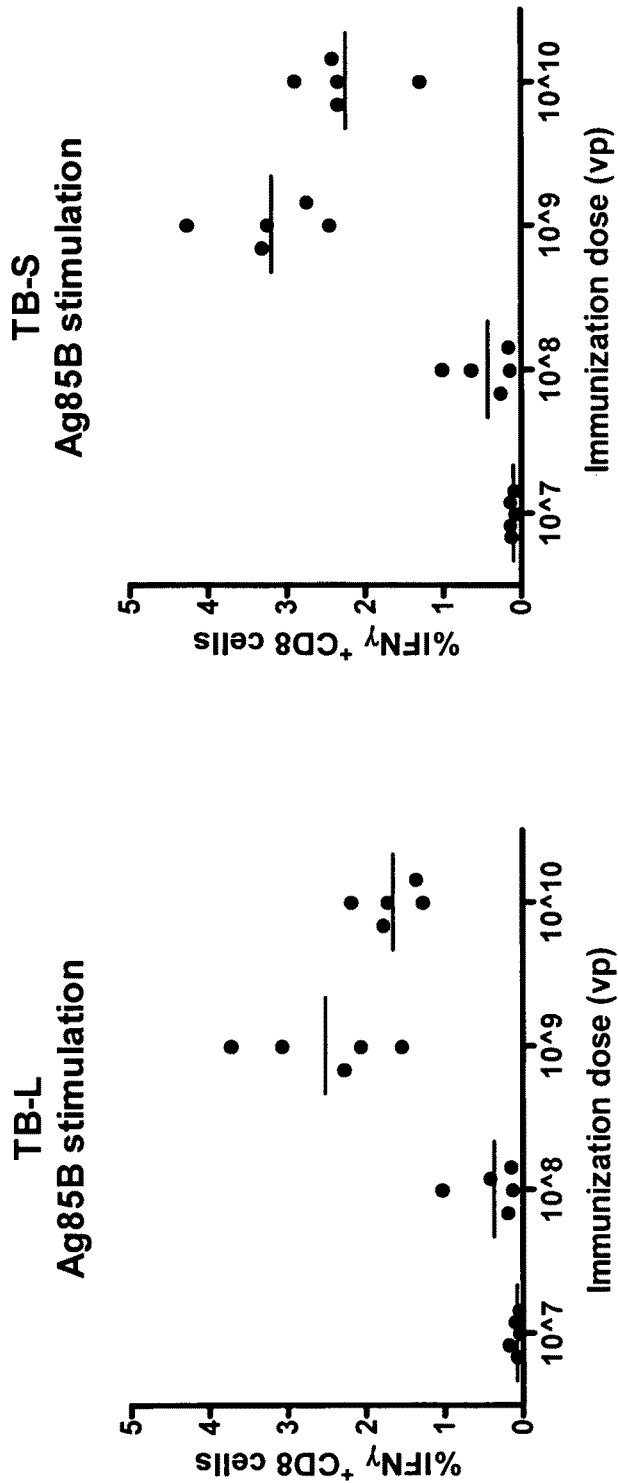

Therefore, an additional dose response experiment was performed in which the in vitro stimulation peptide pool of Ag85B was reconstituted with p1 and p2 from the Ag85A pool. The experiment was performed with both TB-S and TB-L vectors, using doses of $10^7$, $10^8$, $10^9$, and $10^{10}$ vp. The T cell response was determined two weeks after immunization, generally as described above. As negative controls, one group of mice was injected with PBS, while one group was injected with an empty Ad35 virus ($10^{10}$ vp). The results with respect to CD8 cells are presented in FIG. 17G (TB-L, left graph, TB-S, right graph). Clearly, CD8-positive cells were measured upon in vitro stimulation with the adjusted Ag85B pool, although the peptides from the Ag85A antigen were identical to the peptides of the Ag85B antigen, which were originally used and did not provide any positive results. These observations, nevertheless, also show that the Ag85B protein as encoded by the Ad35-based adenoviruses can induce a CD8-positive T cell response after infection of the viruses.

Example 7

Ad35-Based TB Vectors Used as a Boost Upon Priming with BCG

In another experiment, Ad35 vectors expressing TB antigens were tested as a boosting agent for BCG immunization. Hereto, groups of mice were injected subcutaneously with BCG vaccine (Bacilli Calmette-Guerin; reference standard FDA and generally known in the art of tuberculosis vaccination) according to protocols delivered by the FDA (standards and testing section CBER).

Four groups of mice (eight mice per group) were primed with BCG ($6 \times 10^5$ cfu/mouse) subcutaneously ten weeks prior to infection with the adenoviral vectors based on Ad35 carrying the three directly linked TB antigens (TB-S) or with the adenoviral Ad35 vectors carrying the following combinations of antigens:

TB-4 alone (comprising the Ag85A and Ag85B direct fusion)
TB-4+TB-7 (comprising TB10.4 alone)
TB-5 (comprising Ag85A alone)+TB-6 (comprising Ag85B alone)+TB-7.

Figure 18A:
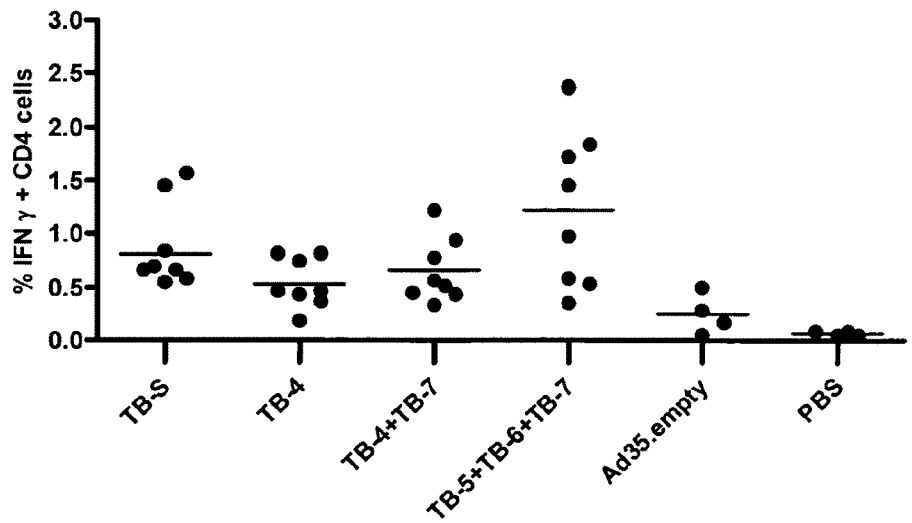
FIG. 18: CD4 and CD8 responses after priming with BCG and boosting with different Ad-TB vectors. CD4 response towards Ag85A (FIG. 18A), Ag85B (FIG. 18C) and TB10.4 (FIG. 18E). CD8 response towards Ag85A (FIG. 18B), Ag85B (FIG. 18D) and TB10.4 (FIG. 18F).
Figure 18B:
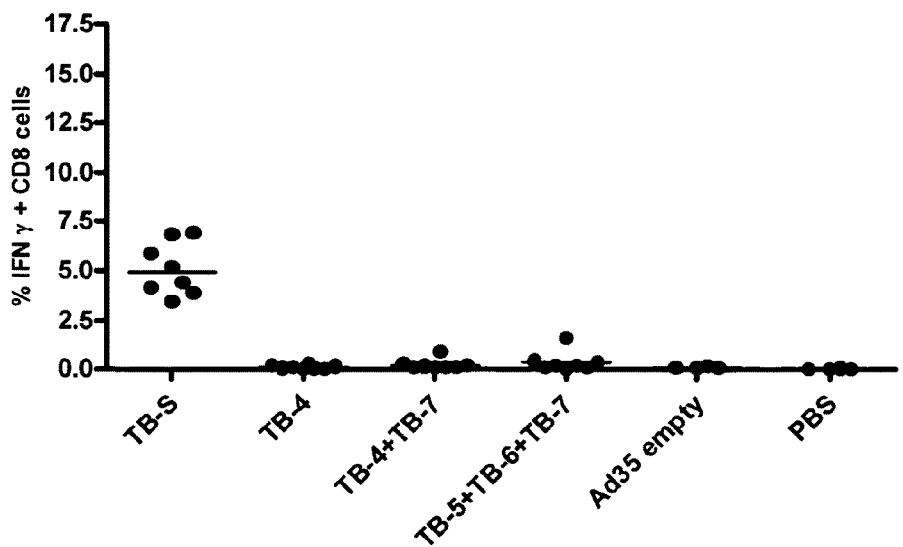

Two control groups (four mice per group) were primed with PBS or with BCG, whereafter the PBS group received PBS as mock-immunization, and the BCG-primed control group received $10^9$ vp of the empty Ad35 vector. Injections with the Ad35-based vectors were performed in all cases with $10^9$ vp, intramuscularly. Four weeks post-infection (14 weeks after prime), mice were sacrificed and splenocytes were isolated and used as described above. The results are shown in FIG. 18. The presence of the Ag85A antigen resulted in a significant effect towards Ag85A-specific CD4 cells (FIG. 18A). As expected (see also FIG. 13, Panel B), the triple construct TB-S induced an Ag85A-specific CD8 response, while the TB-4 vector did not induce such a response (FIG. 18B).

Similar results were found earlier (FIG. 13, Panel B), indicating that the presence of Ag85A alone or in combination with Ag85B does not give a CD8 response, whereas such a response is found when TB10.4 is present. Interestingly, no effect was determined when the separate vectors were injected but in a single shot (TB-4/TB-7 or TB-5/TB-6/TB-7 in FIG. 18B), indicating that the TB10.4 antigen cannot induce an Ag85A-specific CD8 response when co-injected, but rather that the antigen should be present in the same construct or at least in the same cell. The mechanism for the adjuvant effect of TB10.4 is yet unclear.

Figure 18C:
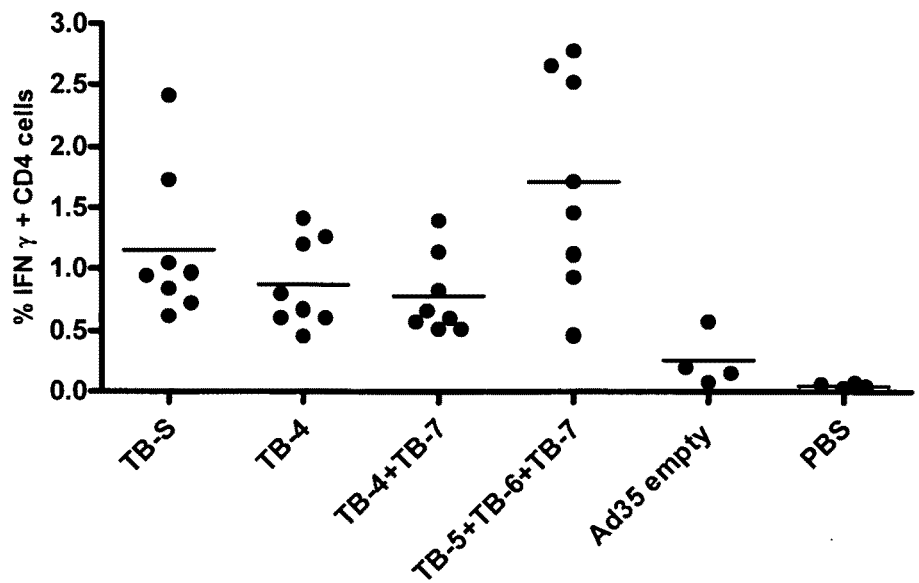
Figure 18D:
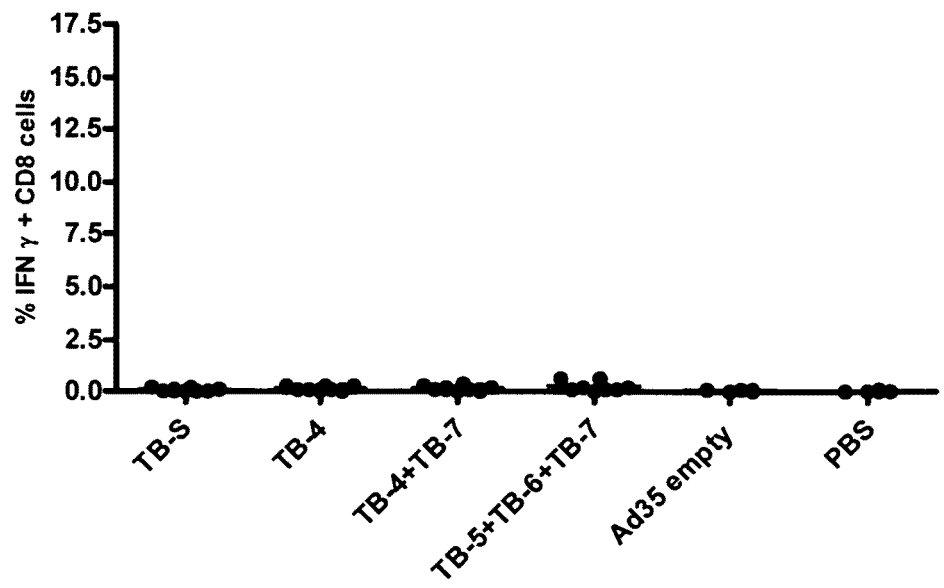

The effects seen with the Ag85B antigen are in concert with what was found earlier (FIGS. 18C and 18D). It must be noted that the presence of the TB10.4 antigen in the triple construct TB-S does not give rise to an Ag85B-specific CD8 response, in contrast to what is found with Ag85A. Both antigens are well expressed from the constructs, as was shown in FIG. 10B. The negative effect may be due to a corrupted peptide pool used to measure any CD8 response towards Ag85B (see Example 6 and below).

Figure 18E:
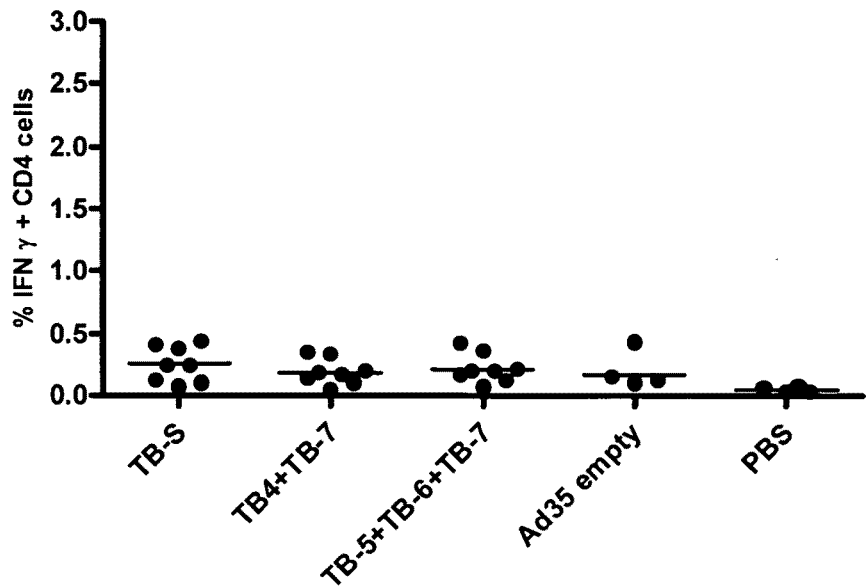
Figure 18F:
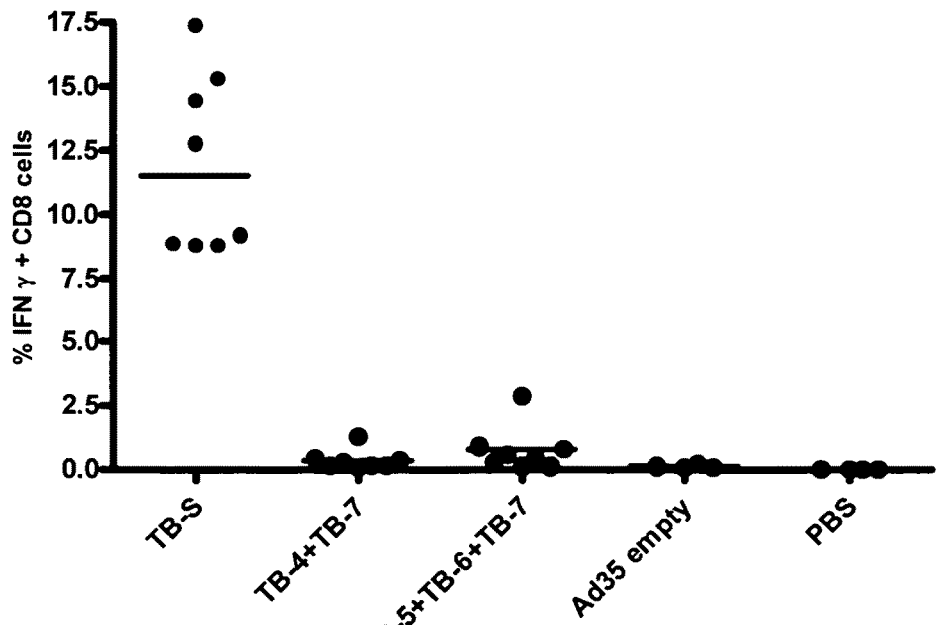

The induction of CD4+ cells using TB10.4 is very low (FIG. 18E). The induction of CD8+ cells using TB10.4 in a separate vector (TB-5/TB-6/TB-7) is significant (note the scale on the y-axis; see also FIG. 15, Panel B). The induction of TB10.4-specific CD8 cells using TB-S is very high (FIG. 18F), with an average of around 12% IFNγ positive CD8 cells.

It can be concluded that the TB10.4 antigen is capable of inducing a CD8 response towards an antigen that as a single construct does not give rise to a CD8 response (Ag85A). It is known that activation of CD8 cells requires a somewhat higher antigenic threshold than the activation of CD4 cells, which is at least partly due to complex machinery involved in antigen processing and presentation by MHC class I molecules (Storin and Bachmann, 2004). Here, it was found that when TB10.4 was coupled to antigens Ag85A and Ag85B in a triple-antigen construct, strong CD8 responses were triggered, not only against TB10.4 itself but also against Ag85A. It is likely that the physical presence of TB10.4 in the construct increases the efficiency of transport of the fusion protein to the proteosome, which is necessary for the efficient presentation to and activation of CD8 cells. The reason for the higher TB10.4-specific CD8 cell response is most likely due to an increased expression level of the triple construct in comparison to the vector carrying the TB10.4 antigen alone. Although the CD8 response towards TB10.4 alone was also significant, no expression levels of TB10.4 could be determined due to lack of TB10.4-specific antisera for western blotting.

The increased targeting to the proteosome might be the result of the presence of specific sites in the TB10.4 molecule, such as sequences involved in binding of ubiquitin (or other molecules responsible for labeling the proteins destined for processing), or transporter proteins, or sequences that otherwise increase processing and presentation in the context of MHC class I molecules (Wang et al. 2004).

Alternatively, the presence of TB10.4 protein in the construct might physically destabilize the fusion protein, leading to increased degradation rate of the molecule. Increased level of antigen processing leads in general to increased CD8 cell activation. Furthermore, if much protein ends up in the proteosome for class I presentation, less will be present in cytosol and extracellularly and, thus, not be available for activation of B cells. It has been reported that an inverse correlation exists between antigen processing (i.e., CD8 activation) and antigen-specific antibody titer (Delogu et al. 2000). It is interesting to mention that a much stronger antigen-immunofluorescence was observed in sera from mice immunized with double-antigen constructs rather than from the triple-antigen construct-immunized mice. This finding suggests that our triple-antigen molecules containing TB10.4 are highly susceptible to proteosome degradation and CD8 cell activation and, thus, less available for antibody induction. As a strong T cell response is a preferable response against tuberculosis, it is concluded that an Ad35-based triple-antigen vector, which comprises a nucleic acid encoding the TB10.4 antigen and at least one other TB antigen, preferably Ag85A and more preferably, both Ag85A and Ag85B, is very suited to be used in a vaccine against tuberculosis. The found effects may be even further increased by using BCG as a priming agent, as indicated by the results shown in FIG. 18.

Figure 25:
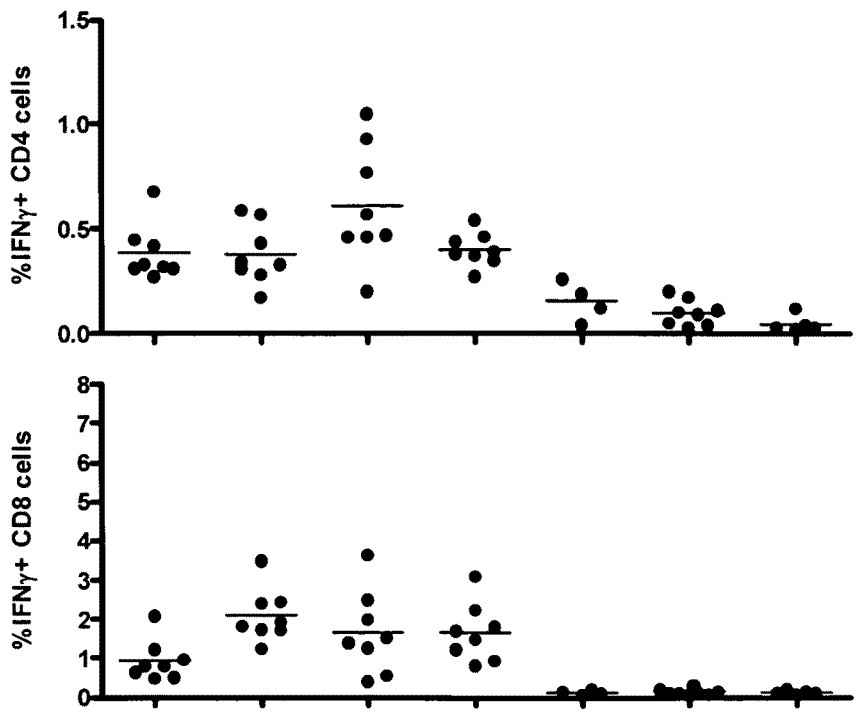
FIG. 25: Ag85A stimulation in a BCG prime/Ad35-TB boost experiment with a long-term read-out. Upper panel: CD4 response; lower panel: CD8 response. Ad35.E=empty Ad35 virus.
Figure 26:
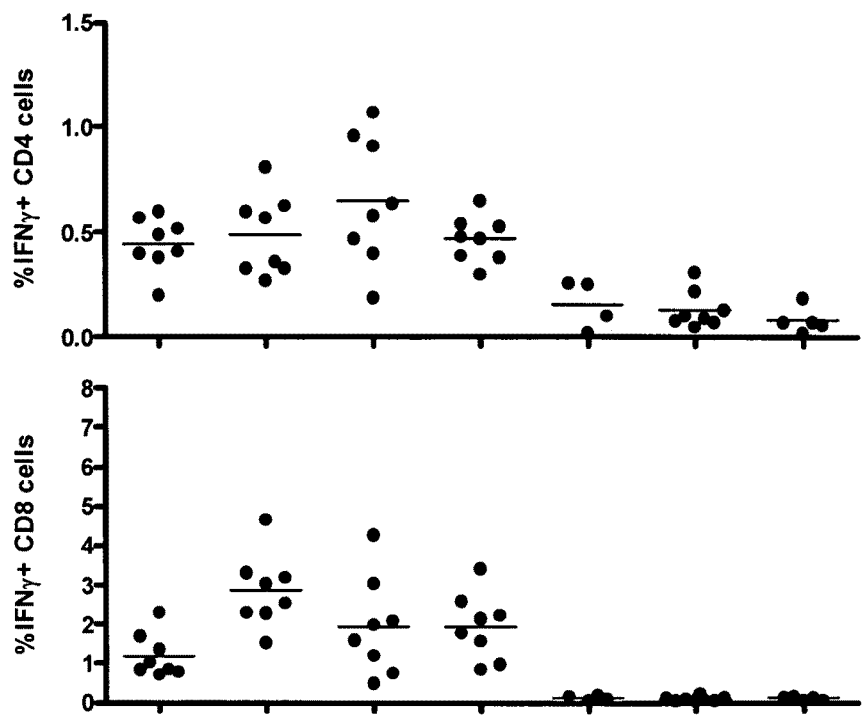
FIG. 26: Ag85B stimulation in a BCG prime/Ad35-TB boost experiment with a long-term read-out. Upper panel: CD4 response; lower panel: CD8 response. Ad35.E=empty Ad35 virus.
Figure 27:
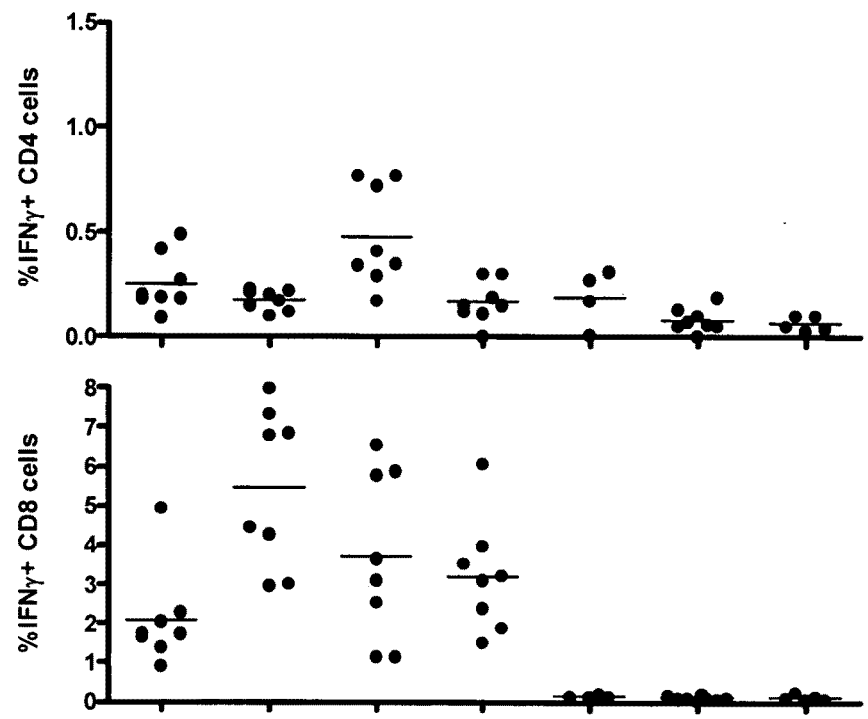
FIG. 27: TB10.4 stimulation in a BCG prime/Ad35-TB boost experiment with a long-term read-out. Upper panel: CD4 response; lower panel: CD8 response. Ad35.E=empty Ad35 virus.

Using the new peptide pool for Ag85B with the peptides p1 and p2 of Ag85A added (as described in Example 6), also the prime/boost study with BCG prime, Ad35-TB boost was repeated, although now the splenocytes were removed from mice that were sacrificed 26 weeks after prime (16 weeks after immunization). Mice (eight per group) were immunized with PBS, Ad35.Empty, Ad35.TB-S, or Ad35.TB-L with either $10^9$ or $10^{10}$ vp of the respective viral vectors. Results are shown in FIG. 25 (Ag85A stimulation), FIG. 26 (Ag85B stimulation) and FIG. 27 (TB10.4 stimulation). The results clearly indicate that significant CD4 and CD8 responses can still be measured after prolonged period of time.

Example 8

Prime-Boost-Challenge Experiment in Guinea Pigs

In a subsequent experiment, it was investigated whether priming, with BCG, followed by a boost with Ad35-based TB vectors, would protect against a *Mycobacterium tuberculosis* infection in a challenging set-up.

Guinea pigs were initially primed with BCG typically as indicated above ($6 \times 10^5$ cfu per animal). After 14 weeks, the animals were either immunized with $10^{10}$ vp Ad35.TB-S (Ag85A-Ag85B-TB10.4) or Ad35.TB-4 (Ag85A-Ag85B) recombinant viruses, or injected with PBS (control group). Eight weeks later, the animals were challenged with ~100 cfu *M. tuberculosis* per animal. The animals are monitored up to approximately 78 weeks post-prime for survival. Intermediate observations suggest that the BCG prime followed by an Ad35-TB boost ensures a higher survival rate than BCG alone.

References

Delogu G. et al. (2000). DNA vaccination against tuberculosis: expression of a ubiquitin-conjugated tuberculosis protein enhances antimycobacterial immunity. *Infect. Immun.* 68:3097-3102.

Jung T. et al. (1993). Detection of intracellular cytokines by flow cytometry. *J. Immunol. Meth.* 159:197-207.

Kaufmann S. H. E. (2000). Is the development of a new tuberculosis vaccine possible? *Nat. Med.* 6:955-960.

Kronenberg M. and L. Gapin (2002). The unconventional lifestyle of NKT cells. *Nat. Rev. Immunol.* 2:557-568.

Sander B. et al. (1991). Differential regulation of lymphokine production in mitogen-stimulated murine spleen cells. *Eur. J. Immunol.* 21:1887-1892.

Shabram P. W. et al. (1997). Analytical anion-exchange HPLC of recombinant type-5 adenoviral particles. *Hum. Gene Ther.* 8:453-465.

Skalka A. M. (1989). Retroviral proteases: first glimpses at the anatomy of a processing machine. *Cell* 56:911-913.

Storin T. and M. F. Bachmann (2004). Loading of MHC class I and II presentation pathways by exogenous antigens: a quantitative in vivo comparison. *J. Immunol.* 172:6129-6135.

Wang J. and Z. Xing (2002). Tuberculosis vaccines: the past, present and future. *Expert Rev. Vaccines* 1(3):341-354.

Wang Q.-M. et al. (2004). Epitope DNA vaccines against tuberculosis: spacers and ubiquitin modulates cellular immune responses elicited by epitope DNA vaccine. *Scand. J. Immunol.* 60:219-225.

What is claimed is:

1. A recombinant nucleic acid molecule comprising:
a nucleic acid sequence encoding Ag85A, Ag85B and TB10.4 antigens of *Mycobacterium tuberculosis* under control of a promoter, wherein the encoded antigens are a fusion protein comprising amino acids 1-676 of SEQ ID NO:7.

2. The recombinant nucleic acid molecule of claim 1, wherein the nucleic acid sequence encoding the antigens comprises nucleotides 13-2043 of SEQ ID NO:4.

3. A recombinant, replication-deficient adenovirus comprising:
the recombinant nucleic acid molecule of claim 1,
wherein the adenovirus is a bovine adenovirus, a canine adenovirus, or a simian adenovirus.

4. The recombinant, replication-deficient adenovirus of claim 3, wherein the nucleic acid sequence encoding the antigens comprises nucleotides 13-2043 of SEQ ID NO:4.

5. The recombinant, replication-deficient adenovirus of claim 4, wherein the adenovirus is simian adenovirus isolated from a chimpanzee.

6. A tuberculosis vaccine comprising:
the recombinant, replication-deficient adenovirus of claim 5, and
a pharmaceutically acceptable excipient.

7. A tuberculosis vaccine comprising:
the recombinant, replication-deficient adenovirus of claim 4, and
a pharmaceutically acceptable excipient.

8. The recombinant, replication-deficient adenovirus of claim 3, wherein the adenovirus is simian adenovirus isolated from a chimpanzee.

9. A tuberculosis vaccine comprising:
the recombinant, replication-deficient adenovirus of claim 8, and
a pharmaceutically acceptable excipient.

10. A tuberculosis vaccine comprising:
the recombinant, replication-deficient adenovirus of claim 3, and
a pharmaceutically acceptable excipient.

11. The tuberculosis vaccine of claim 10, further comprising:
an adjuvant.

12. A recombinant, replication-deficient adenovirus comprising:
a recombinant nucleic acid molecule comprising:
a nucleic acid sequence encoding Ag85A, Ag85B and TB10.4 antigens of *Mycobacterium tuberculosis*,
wherein the nucleic acid sequence comprises, in the 5' to 3' direction, an expression control sequence, the Ag85A coding sequence, the Ag85B coding sequence, and the TB10.4 coding sequence,
wherein the adenovirus is a bovine, a canine, or a simian adenovirus.

13. The recombinant, replication-deficient adenovirus of claim 12, wherein the adenovirus is simian adenovirus isolated from a chimpanzee.

14. The recombinant, replication-deficient adenovirus of claim 13, which is a C68 (also known as Pan9), a Pan5, a Pan6, or a Pan7 adenovirus.

15. A tuberculosis vaccine comprising:
the recombinant, replication-deficient adenovirus of claim 13, and
a pharmaceutically acceptable excipient.

16. A tuberculosis vaccine comprising:
the recombinant, replication-deficient adenovirus of claim 12, and
a pharmaceutically acceptable excipient.

17. The tuberculosis vaccine of claim 16, further comprising:
an adjuvant.

18. The recombinant, replication-deficient adenovirus of claim 12, further comprising:
an adjuvant.

* * * * *

SEQUENCE LISTING

```
<160> NUMBER OF SEQ ID NOS: 28

<210> SEQ ID NO 1
<211> LENGTH: 51
<212> TYPE: DNA
<213> ORGANISM: Artificial
<220> FEATURE:
<223> OTHER INFORMATION: Synthetic oligonucleotide Myc-oligo 1

<400> SEQUENCE: 1
ctagcaagaa aaccgagcag aagctgatct ccgaggagga cctgtgataa t          51

<210> SEQ ID NO 2
<211> LENGTH: 51
<212> TYPE: DNA
<213> ORGANISM: Artificial
<220> FEATURE:
<223> OTHER INFORMATION: Synthetic oligonucleotide Myc-oligo 2

<400> SEQUENCE: 2
ctagattatc acaggtcctc ctcggagatc agcttctgct cggttttctt g          51

<210> SEQ ID NO 3
<211> LENGTH: 2757
<212> TYPE: DNA
<213> ORGANISM: Artificial
<220> FEATURE:
<223> OTHER INFORMATION: Codon-optimized Mycobacterium tuberculosis
      antigen TB-LM
<220> FEATURE:
```

<221> NAME/KEY: misc_feature
<222> LOCATION: (1)..(6)
<223> OTHER INFORMATION: HindIII cloning site
<220> FEATURE:
<221> NAME/KEY: misc_feature
<222> LOCATION: (7)..(12)
<223> OTHER INFORMATION: Kozak
<220> FEATURE:
<221> NAME/KEY: misc_feature
<222> LOCATION: (13)..(471)
<223> OTHER INFORMATION: ALV protease
<220> FEATURE:
<221> NAME/KEY: misc_feature
<222> LOCATION: (472)..(1356)
<223> OTHER INFORMATION: Ag85A mature coding sequence
<220> FEATURE:
<221> NAME/KEY: misc_feature
<222> LOCATION: (1357)..(1458)
<223> OTHER INFORMATION: linker/digestion sequence
<220> FEATURE:
<221> NAME/KEY: misc_feature
<222> LOCATION: (1459)..(2313)
<223> OTHER INFORMATION: Ag85B mature coding sequence
<220> FEATURE:
<221> NAME/KEY: misc_feature
<222> LOCATION: (2314)..(2415)
<223> OTHER INFORMATION: linker/digestion sequence
<220> FEATURE:
<221> NAME/KEY: misc_feature
<222> LOCATION: (2416)..(2703)
<223> OTHER INFORMATION: TB10.4 coding sequence
<220> FEATURE:
<221> NAME/KEY: misc_feature
<222> LOCATION: (2704)..(2745)
<223> OTHER INFORMATION: myc tag
<220> FEATURE:
<221> NAME/KEY: terminator
<222> LOCATION: (2746)..(2751)
<220> FEATURE:
<221> NAME/KEY: misc_feature
<222> LOCATION: (2752)..(2757)
<223> OTHER INFORMATION: XbaI cloning site

<400> SEQUENCE: 3

| | | | | | |
|---|---|---|---|---|---|
| aagcttgcca | ccatgctggc | catgaccatg | gagcaccggg | accggcccct | ggtgagagtg | 60 |
| atcctgacca | acaccggcag | ccaccccgtg | aagcagcgga | gcgtgtacat | caccgccctg | 120 |
| ctggacagcg | gagccgacat | caccatcatc | agcgaggagg | actggcccac | cgactggccc | 180 |
| gtggtggaca | ccgccaaccc | ccagatccac | ggcatcggcg | gaggcatccc | catgcggaag | 240 |
| agccgggaca | tgatcgagct | gggcgtgatc | aaccgggacg | gcagcctgga | gcggcccctg | 300 |
| ctgctgttcc | ccgccgtggc | catggtgcgg | ggcagcatcc | tgggccggga | ctgcctgcag | 360 |
| ggcctgggcc | tgcggctgac | caacctgggc | agcagcggcc | cctggcctgc | ccccgagccc | 420 |
| cctgccgtga | gcctggctat | gacaatggaa | cacagagaca | gacccctggt | gttcagcaga | 480 |
| cccggcctgc | ccgtggagta | cctgcaggtg | cccagcccca | gcatgggccg | ggacatcaaa | 540 |
| gtgcagttcc | agagcggcgg | agccaacagc | cctgccctgt | acctgctgga | cggcctgcgg | 600 |
| gcccaggacg | acttcagcgg | ctgggacatc | aacacccccg | ccttcgagtg | gtacgaccag | 660 |
| agcggcctga | gcgtggtgat | gcccgtgggc | ggcagagca | gcttctacag | cgactggtat | 720 |
| cagccccgcct | gcggcaaggc | cggctgccag | acctacaagt | gggagacctt | cctgaccagc | 780 |
| gagctgcccg | gctggctgca | ggccaaccgg | cacgtgaagc | ccaccggcag | cgccgtggtg | 840 |
| ggcctgagca | tggccgccag | cagcgccctg | accctggcca | tctaccaccc | ccagcagttc | 900 |
| gtgtacgccg | agccatgag | cggcctgctg | accccagcc | aggccatggg | ccccaccctg | 960 |
| atcggcctgg | ccatgggcga | cgccggaggc | tacaaggcca | cgacatgtg | ggcccccaag | 1020 |
| gaggaccccg | cctggcagcg | gaacgacccc | ctgctgaacg | tgggcaagct | gatcgccaac | 1080 |

| | |
|---|---|
| aacacccgcg tgtgggtgta ctgcggcaac ggcaagccca gcgacctggg cggcaacaac | 1140 |
| ctgcccgcca agttcctgga gggcttcgtg cggaccagca acatcaagtt ccaggacgcc | 1200 |
| tacaacgccg gaggcggcca caacggcgtg ttcgacttcc ccgacagcgg cacccacagc | 1260 |
| tgggagtact ggggagccca gctgaacgcc atgaagcccg acctgcagcg ggccctgggc | 1320 |
| gccacccca acaccggccc tgccccccag ggcgctcccc ccagcaagag caagaagggc | 1380 |
| ggagccgccg ctatgagcag cgccatccag cccctggtga tggccgtggt gaaccgggag | 1440 |
| cgggacggcc agaccggctt cagccggcct ggcctgcctg tggaatatct gcaggtgccc | 1500 |
| tccccctcta tgggccgcga tattaaagtg cagtttcagt ccggcggcaa caatagccca | 1560 |
| gccgtgtatc tgctggatgg gctgagagcc caggacgatt acaatggctg gatatcaat | 1620 |
| acacctgcct ttgagtggta ctatcagtct ggcctgtcca tcgtgatgcc tgtgggagga | 1680 |
| cagtccagct tctactctga ctggtactct cctgcctgtg gcaaagccgg atgtcagaca | 1740 |
| tacaaatggg aaacatttct gacctccgag ctgccccagt ggctgagcgc caacagagcc | 1800 |
| gtgaagccta caggctctgc cgccatcggc ctgtctatgg ccggcagctc tgccatgatc | 1860 |
| ctggccgcct atcaccctca gcagtttatc tacgccggca gcctgtctgc cctgctggat | 1920 |
| ccctctcagg gcatgggccc ttctctgatt ggactggcta tggggacgc tggcggatac | 1980 |
| aaggccgccg atatgtgggg acccagcagc gaccctgcct gggagagaaa cgaccccacc | 2040 |
| cagcagatcc ccaaactggt ggccaacaat accaggctgt gggtgtactg tggaaatggc | 2100 |
| acccccaacg agctgggagg cgccaacatc cccgccgagt ttctggagaa cttcgtgaga | 2160 |
| agcagcaacc tgaagtttca ggatgcctat aatgccgccg aggccacaa tgccgtgttc | 2220 |
| aatttccccc ccaacggcac ccactcttgg gaatattggg gcgctcagct gaatgctatg | 2280 |
| aaggggacc tgcagagcag cctgggagcc ggccctccca gcaagtctaa gaaggaggc | 2340 |
| gccgctgcca tgtctagcgc cattcagcct ctggtgatgg ctgtggtgaa cagagagagg | 2400 |
| gacgggcaga ctggcatgag ccagatcatg tacaactacc ccgccatgct gggccacgcc | 2460 |
| ggcgacatgg ccggctacgc cggcacactg cagagcctgg gcgccgagat cgccgtggag | 2520 |
| caggccgccc tgcagtctgc ctggcagggc gacaccggca tcacctacca ggcctggcag | 2580 |
| gcccagtgga accaggccat ggaggacctg gtgcgggcct accacgccat gagcagcacc | 2640 |
| cacgaggcca acaccatggc catgatggcc cgggacaccg ccgaggccgc caagtgggc | 2700 |
| ggcagcaaga aaaccgagca gaagctgatc tccgaggagg acctgtgata atctaga | 2757 |

```
<210> SEQ ID NO 4
<211> LENGTH: 2097
<212> TYPE: DNA
<213> ORGANISM: Artificial
<220> FEATURE:
<223> OTHER INFORMATION: Synthetic codon-optimized Mycobacterium
      tuberculosis antigen TB-SM
<220> FEATURE:
<221> NAME/KEY: misc_feature
<222> LOCATION: (1)..(6)
<223> OTHER INFORMATION: HindIII cloning site
<220> FEATURE:
<221> NAME/KEY: misc_feature
<222> LOCATION: (7)..(12)
<223> OTHER INFORMATION: Kozak
<220> FEATURE:
<221> NAME/KEY: misc_feature
<222> LOCATION: (13)..(900)
<223> OTHER INFORMATION: Ag85A coding sequence
<220> FEATURE:
<221> NAME/KEY: misc_feature
<222> LOCATION: (901)..(1755)
```

```
<223> OTHER INFORMATION: Ag85B mature coding sequence
<220> FEATURE:
<221> NAME/KEY: misc_feature
<222> LOCATION: (1756)..(2043)
<223> OTHER INFORMATION: TB10.4 coding sequence
<220> FEATURE:
<221> NAME/KEY: misc_feature
<222> LOCATION: (2044)..(2085)
<223> OTHER INFORMATION: myc tag
<220> FEATURE:
<221> NAME/KEY: terminator
<222> LOCATION: (2086)..(2091)
<220> FEATURE:
<221> NAME/KEY: misc_feature
<222> LOCATION: (2092)..(2097)
<223> OTHER INFORMATION: XbaI cloning site

<400> SEQUENCE: 4
```

| | | | | | |
|---|---|---|---|---|---|
| aagcttgcca | ccatgttcag | cagacccggc | ctgcccgtgg | agtacctgca | ggtgcccagc | 60 |
| cccagcatgg | gccgggacat | caaagtgcag | ttccagagcg | gcggagccaa | cagccctgcc | 120 |
| ctgtacctgc | tggacggcct | gcgggcccag | gacgacttca | gcggctggga | catcaacacc | 180 |
| cccgccttcg | agtggtacga | ccagagcggc | ctgagcgtgg | tgatgccggt | gggcggccag | 240 |
| agcagcttct | acagcgactg | gtatcagccc | gcctgcggca | aggccggctg | ccagacctac | 300 |
| aagtgggaga | ccttcctgac | cagcgagctg | cccggctggc | tgcaggccaa | ccggcacgtg | 360 |
| aagcccaccg | gcagcgccgt | ggtgggcctg | agcatggccg | ccagcagcgc | cctgaccctg | 420 |
| gccatctacc | accccagca | gttcgtgtac | gccggagcca | tgagcggcct | gctggacccc | 480 |
| agccaggcca | tggcccccac | cctgatcggc | ctggccatgg | gcgacgccgg | aggctacaag | 540 |
| gccagcgaca | tgtggggccc | caaggaggac | ccgcctggc | agcggaacga | ccccctgctg | 600 |
| aacgtgggca | gctgatcgc | caacaacacc | cgcgtgtggg | tgtactgcgg | caacggcaag | 660 |
| cccagcgacc | tgggcggcaa | caacctgccc | gccaagttcc | tggagggctt | cgtgcggacc | 720 |
| agcaacatca | gttccagga | cgcctacaac | gccgaggcg | ccacaacgg | cgtgttcgac | 780 |
| ttccccgaca | gcggcaccca | cagctgggag | tactgggag | cccagctgaa | cgccatgaag | 840 |
| cccgacctgc | agcgggccct | gggcgccacc | cccaacaccg | ccctgccccc | cagggcgct | 900 |
| ttcagccggc | ctggcctgcc | tgtggaatat | ctgcaggtgc | cctccccctc | tatgggccgc | 960 |
| gatattaaag | tgcagtttca | gtccggcggc | aacaatagcc | cagccgtgta | tctgctggat | 1020 |
| gggctgagag | cccaggacga | ttacaatggc | tgggatatca | atacacctgc | ctttgagtgg | 1080 |
| tactatcagt | ctggcctgtc | catcgtgatg | cctgtgggag | acagtccag | cttctactct | 1140 |
| gactggtact | ctcctgcctg | tggcaaagcc | ggatgtcaga | catacaaatg | ggaaacattt | 1200 |
| ctgacctccg | agctgcccca | gtggctgagc | gccaacagag | ccgtgaagcc | tacaggctct | 1260 |
| gccgccatcg | gcctgtctat | ggccggcagc | tctgccatga | tcctggccgc | ctatcaccct | 1320 |
| cagcagttta | tctacgccgg | cagcctgtct | gccctgctgg | atccctctca | gggcatgggc | 1380 |
| ccttctctga | ttggactggc | tatggggac | gctggcggat | acaaggccgc | cgatatgtgg | 1440 |
| ggacccagca | gcgaccctgc | ctgggagaga | aacgacccca | cccagcagat | ccccaaactg | 1500 |
| gtggccaaca | ataccaggct | gtgggtgtac | tgtggaaatg | gcaccccaa | cgagctggga | 1560 |
| ggcgccaaca | tccccgccga | gtttctggag | aacttcgtga | agcagcaa | cctgaagttt | 1620 |
| caggatgcct | ataatgccgc | cggaggccac | aatgccgtgt | tcaatttccc | ccccaacggc | 1680 |
| acccactctt | gggaatattg | gggcgctcag | ctgaatgcta | tgaaggggga | cctgcagagc | 1740 |
| agcctgggag | ccggcatgag | ccagatcatg | tacaactacc | ccgccatgct | gggccacgcc | 1800 |
| ggcgacatgg | ccggctacgc | cggcacactg | cagagcctgg | gcgccgagat | cgccgtggag | 1860 |

-continued

```
caggccgccc tgcagtctgc ctggcagggc gacaccggca tcacctacca ggcctggcag    1920
gcccagtgga accaggccat ggaggacctg gtgcgggcct accacgccat gagcagcacc    1980
cacgaggcca acaccatggc catgatggcc cgggacaccg ccgaggccgc caagtggggc    2040
ggcagcaaga aaaccgagca gaagctgatc tccgaggagg acctgtgata atctaga      2097
```

```
<210> SEQ ID NO 5
<211> LENGTH: 2193
<212> TYPE: DNA
<213> ORGANISM: Artificial
<220> FEATURE:
<223> OTHER INFORMATION: Synthetic codon-optimized Mycobacterium
      tuberculosis antigen TB-FLM
<220> FEATURE:
<221> NAME/KEY: misc_feature
<222> LOCATION: (1)..(6)
<223> OTHER INFORMATION: HindIII cloning site
<220> FEATURE:
<221> NAME/KEY: misc_feature
<222> LOCATION: (7)..(12)
<223> OTHER INFORMATION: Kozak
<220> FEATURE:
<221> NAME/KEY: misc_feature
<222> LOCATION: (13)..(900)
<223> OTHER INFORMATION: Ag85A mature coding sequence
<220> FEATURE:
<221> NAME/KEY: misc_feature
<222> LOCATION: (901)..(948)
<223> OTHER INFORMATION: linker sequence
<220> FEATURE:
<221> NAME/KEY: misc_feature
<222> LOCATION: (949)..(1803)
<223> OTHER INFORMATION: Ag85B mature coding sequence
<220> FEATURE:
<221> NAME/KEY: misc_feature
<222> LOCATION: (1804)..(1851)
<223> OTHER INFORMATION: linker sequence
<220> FEATURE:
<221> NAME/KEY: misc_feature
<222> LOCATION: (1852)..(2138)
<223> OTHER INFORMATION: TB10.4 coding sequence
<220> FEATURE:
<221> NAME/KEY: misc_feature
<222> LOCATION: (2139)..(2181)
<223> OTHER INFORMATION: myc tag
<220> FEATURE:
<221> NAME/KEY: terminator
<222> LOCATION: (2182)..(2187)
<220> FEATURE:
<221> NAME/KEY: misc_feature
<222> LOCATION: (2188)..(2193)
<223> OTHER INFORMATION: XbaI cloning site

<400> SEQUENCE: 5
```

```
aagcttgcca ccatgttcag cagacccggc ctgcccgtgg agtacctgca ggtgcccagc      60
cccagcatgg gccgggacat caaagtgcag ttccagagcg gcggagccaa cagccctgcc     120
ctgtacctgc tggacggcct gcgggcccag gacgacttca gcggctggga catcaacacc     180
cccgccttcg agtggtacga ccagagcggc ctgagcgtgg tgatgcccgt gggcggccag     240
agcagcttct acagcgactg gtatcagccc gcctgcggca aggccggctg ccagacctac     300
aagtgggaga ccttcctgac cagcgagctg ccccggctgg ctgcaggccaa ccggcacgtg     360 aagcccaccg gcagcgccgt ggtgggcctg agcatggccg ccagcagcgc cctgaccctg     420
gccatctacc accccagca gttcgtgtac gccgagcca tgagcggcct gctggacccc     480
agccaggcca tgggcccac cctgatcggc ctggccatgg gcgacgccgg aggctacaag     540
gccagcgaca tgtggggccc caaggaggac ccgcctggc agcggaacga ccccctgctg     600
aacgtgggca agctgatcgc caacaacacc cgcgtgtggg tgtactgcgg caacggcaag     660
```

```
cccagcgacc tgggcggcaa caacctgccc gccaagttcc tggagggctt cgtgcggacc    720
agcaacatca agttccagga cgcctacaac gccggaggcg ccacaacgg cgtgttcgac    780
ttccccgaca gcggcaccca cagctgggag tactggggag cccagctgaa cgccatgaag    840
cccgacctgc agcgggccct gggcgccacc cccaacaccg ccctgcccc ccagggcgct    900
ggcaccggcg gcagcggcgg caccggcagc ggcacaggcg ctctgtgtt cagccggcct    960
ggcctgcctg tggaatatct gcaggtgccc tcccctcta tgggccgcga tattaaagtg   1020
cagtttcagt ccggcggcaa caatagccca gccgtgtatc tgctggatgg gctgagagcc   1080
caggacgatt acaatggctg ggatatcaat acacctgcct ttgagtggta ctatcagtct   1140
ggcctgtcca tcgtgatgcc tgtgggagga cagtccagct tctactctga ctggtactct   1200
cctgcctgtg gcaaagccgg atgtcagaca tacaaatggg aaacatttct gacctccgag   1260
ctgccccagt ggctgagcgc aacagagcc gtgaagccta caggctctgc cgccatcggc   1320
ctgtctatgg ccggcagctc tgccatgatc ctggccgcct atcaccctca gcagtttatc   1380
tacgccggca gcctgtctgc cctgctggat ccctctcagg gcatgggccc ttctctgatt   1440
ggactggcta tggggacgc tggcggatac aaggccgccg atatgtgggg acccagcagc   1500
gaccctgcct gggagagaaa cgaccccacc cagcagatcc ccaaactggt ggccaacaat   1560
accaggctgt gggtgtactg tggaaatggc accccccaacg agctgggagg cgccaacatc   1620
cccgccgagt ttctggagaa cttcgtgaga agcagcaacc tgaagtttca ggatgcctat   1680
aatgccgccg aggccacaa tgccgtgttc aatttccccc ccaacggcac ccactcttgg   1740
gaatattggg gcgctcagct gaatgctatg aaggggggacc tgcagagcag cctgggagcc   1800
ggcggcaccg gaggctctgg cggcacaggc tctggcaccg gcggatctgt gatgagccag   1860
atcatgtaca actaccccgc catgctgggc cacgccggcg acatggccgg ctacgccggc   1920
acactgcaga gcctgggcgc cgagatcgcc gtggagcagg ccgccctgca gtctgcctgg   1980
cagggcgaca ccggcatcac ctaccaggcc tggcaggccc agtggaacca ggccatggag   2040
gacctggtgc gggcctacca cgccatgagc agcacccacg aggccaacac catggccatg   2100
atggcccggg acaccgccga ggccgccaag tggggcggca gcaagaaaac cgagcagaag   2160
ctgatctccg aggaggacct gtgataatct aga                                2193
```

<210> SEQ ID NO 6
<211> LENGTH: 911
<212> TYPE: PRT
<213> ORGANISM: Mycobacterium tuberculosis
<220> FEATURE:
<221> NAME/KEY: MISC_FEATURE
<222> LOCATION: (1)..(153)
<223> OTHER INFORMATION: ALV protease
<220> FEATURE:
<221> NAME/KEY: MISC_FEATURE
<222> LOCATION: (126)..(153)
<223> OTHER INFORMATION: Auto-cleavage site of for the avian leucosis
     protease
<220> FEATURE:
<221> NAME/KEY: MISC_FEATURE
<222> LOCATION: (154)..(448)
<223> OTHER INFORMATION: Ag85A mature protein sequence
<220> FEATURE:
<221> NAME/KEY: MISC_FEATURE
<222> LOCATION: (449)..(482)
<223> OTHER INFORMATION: linker/digestion sequence
<220> FEATURE:
<221> NAME/KEY: MISC_FEATURE
<222> LOCATION: (483)..(767)
<223> OTHER INFORMATION: Ag85B mature protein sequence
<220> FEATURE:

-continued

```
<221> NAME/KEY: MISC_FEATURE
<222> LOCATION: (768)..(801)
<223> OTHER INFORMATION: linker/digestion sequence
<220> FEATURE:
<221> NAME/KEY: MISC_FEATURE
<222> LOCATION: (802)..(897)
<223> OTHER INFORMATION: TB10.4 protein sequence
<220> FEATURE:
<221> NAME/KEY: MISC_FEATURE
<222> LOCATION: (898)..(911)
<223> OTHER INFORMATION: myc tag

<400> SEQUENCE: 6

Met Leu Ala Met Thr Met Glu His Arg Asp Arg Pro Leu Val Arg Val
1               5                   10                  15

Ile Leu Thr Asn Thr Gly Ser His Pro Val Lys Gln Arg Ser Val Tyr
            20                  25                  30

Ile Thr Ala Leu Leu Asp Ser Gly Ala Asp Ile Thr Ile Ile Ser Glu
        35                  40                  45

Glu Asp Trp Pro Thr Asp Trp Pro Val Val Asp Thr Ala Asn Pro Gln
    50                  55                  60

Ile His Gly Ile Gly Gly Ile Pro Met Arg Lys Ser Arg Asp Met
65              70                  75                  80

Ile Glu Leu Gly Val Ile Asn Arg Asp Gly Ser Leu Glu Arg Pro Leu
                85                  90                  95

Leu Leu Phe Pro Ala Val Ala Met Val Arg Gly Ser Ile Leu Gly Arg
            100                 105                 110

Asp Cys Leu Gln Gly Leu Gly Leu Arg Leu Thr Asn Leu Gly Ser Ser
        115                 120                 125

Gly Pro Trp Pro Ala Pro Glu Pro Pro Ala Val Ser Leu Ala Met Thr
    130                 135                 140

Met Glu His Arg Asp Arg Pro Leu Val Phe Ser Arg Pro Gly Leu Pro
145                 150                 155                 160

Val Glu Tyr Leu Gln Val Pro Ser Pro Ser Met Gly Arg Asp Ile Lys
                165                 170                 175

Val Gln Phe Gln Ser Gly Gly Ala Asn Ser Pro Ala Leu Tyr Leu Leu
            180                 185                 190

Asp Gly Leu Arg Ala Gln Asp Asp Phe Ser Gly Trp Asp Ile Asn Thr
        195                 200                 205

Pro Ala Phe Glu Trp Tyr Asp Gln Ser Gly Leu Ser Val Val Met Pro
    210                 215                 220

Val Gly Gly Gln Ser Ser Phe Tyr Ser Asp Trp Tyr Gln Pro Ala Cys
225                 230                 235                 240

Gly Lys Ala Gly Cys Gln Thr Tyr Lys Trp Glu Thr Phe Leu Thr Ser
                245                 250                 255

Glu Leu Pro Gly Trp Leu Gln Ala Asn Arg His Val Lys Pro Thr Gly
            260                 265                 270

Ser Ala Val Val Gly Leu Ser Met Ala Ala Ser Ser Ala Leu Thr Leu
        275                 280                 285

Ala Ile Tyr His Pro Gln Gln Phe Val Tyr Ala Gly Ala Met Ser Gly
    290                 295                 300

Leu Leu Asp Pro Ser Gln Ala Met Gly Pro Thr Leu Ile Gly Leu Ala
305                 310                 315                 320

Met Gly Asp Ala Gly Gly Tyr Lys Ala Ser Asp Met Trp Gly Pro Lys
                325                 330                 335

Glu Asp Pro Ala Trp Gln Arg Asn Asp Pro Leu Leu Asn Val Gly Lys
            340                 345                 350
```

```
Leu Ile Ala Asn Asn Thr Arg Val Trp Val Tyr Cys Gly Asn Gly Lys
        355                 360                 365

Pro Ser Asp Leu Gly Gly Asn Asn Leu Pro Ala Lys Phe Leu Glu Gly
        370                 375                 380

Phe Val Arg Thr Ser Asn Ile Lys Phe Gln Asp Ala Tyr Asn Ala Gly
385                 390                 395                 400

Gly Gly His Asn Gly Val Phe Asp Phe Pro Asp Ser Gly Thr His Ser
                405                 410                 415

Trp Glu Tyr Trp Gly Ala Gln Leu Asn Ala Met Lys Pro Asp Leu Gln
                420                 425                 430

Arg Ala Leu Gly Ala Thr Pro Asn Thr Gly Pro Ala Pro Gln Gly Ala
            435                 440                 445

Pro Pro Ser Lys Ser Lys Lys Gly Ala Ala Ala Met Ser Ser Ala
        450                 455                 460

Ile Gln Pro Leu Val Met Ala Val Asn Arg Glu Arg Asp Gly Gln
465                 470                 475                 480

Thr Gly Phe Ser Arg Pro Gly Leu Pro Val Glu Tyr Leu Gln Val Pro
                485                 490                 495

Ser Pro Ser Met Gly Arg Asp Ile Lys Val Gln Phe Gln Ser Gly Gly
        500                 505                 510

Asn Asn Ser Pro Ala Val Tyr Leu Leu Asp Gly Leu Arg Ala Gln Asp
        515                 520                 525

Asp Tyr Asn Gly Trp Asp Ile Asn Thr Pro Ala Phe Glu Trp Tyr Tyr
        530                 535                 540

Gln Ser Gly Leu Ser Ile Val Met Pro Val Gly Gly Gln Ser Ser Phe
545                 550                 555                 560

Tyr Ser Asp Trp Tyr Ser Pro Ala Cys Gly Lys Ala Gly Cys Gln Thr
                565                 570                 575

Tyr Lys Trp Glu Thr Phe Leu Thr Ser Glu Leu Pro Gln Trp Leu Ser
                580                 585                 590

Ala Asn Arg Ala Val Lys Pro Thr Gly Ser Ala Ala Ile Gly Leu Ser
            595                 600                 605

Met Ala Gly Ser Ser Ala Met Ile Leu Ala Ala Tyr His Pro Gln Gln
        610                 615                 620

Phe Ile Tyr Ala Gly Ser Leu Ser Ala Leu Leu Asp Pro Ser Gln Gly
625                 630                 635                 640

Met Gly Pro Ser Leu Ile Gly Leu Ala Met Gly Asp Ala Gly Gly Tyr
                645                 650                 655

Lys Ala Ala Asp Met Trp Gly Pro Ser Ser Asp Pro Ala Trp Glu Arg
                660                 665                 670

Asn Asp Pro Thr Gln Gln Ile Pro Lys Leu Val Ala Asn Asn Thr Arg
            675                 680                 685

Leu Trp Val Tyr Cys Gly Asn Gly Thr Pro Asn Glu Leu Gly Gly Ala
        690                 695                 700

Asn Ile Pro Ala Glu Phe Leu Glu Asn Phe Val Arg Ser Ser Asn Leu
705                 710                 715                 720

Lys Phe Gln Asp Ala Tyr Asn Ala Ala Gly Gly His Asn Ala Val Phe
                725                 730                 735

Asn Phe Pro Pro Asn Gly Thr His Ser Trp Glu Tyr Trp Gly Ala Gln
                740                 745                 750

Leu Asn Ala Met Lys Gly Asp Leu Gln Ser Ser Leu Gly Ala Gly Pro
        755                 760                 765

Pro Ser Lys Ser Lys Lys Gly Gly Ala Ala Ala Met Ser Ser Ala Ile
770                 775                 780
```

```
Gln Pro Leu Val Met Ala Val Val Asn Arg Glu Arg Asp Gly Gln Thr
785                 790                 795                 800

Gly Met Ser Gln Ile Met Tyr Asn Tyr Pro Ala Met Leu Gly His Ala
            805                 810                 815

Gly Asp Met Ala Gly Tyr Ala Gly Thr Leu Gln Ser Leu Gly Ala Glu
                820                 825                 830

Ile Ala Val Glu Gln Ala Ala Leu Gln Ser Ala Trp Gln Gly Asp Thr
            835                 840                 845

Gly Ile Thr Tyr Gln Ala Trp Gln Ala Gln Trp Asn Gln Ala Met Glu
        850                 855                 860

Asp Leu Val Arg Ala Tyr His Ala Met Ser Ser Thr His Glu Ala Asn
865                 870                 875                 880

Thr Met Ala Met Met Ala Arg Asp Thr Ala Glu Ala Ala Lys Trp Gly
                885                 890                 895

Gly Ser Lys Lys Thr Glu Gln Lys Leu Ile Ser Glu Glu Asp Leu
                900                 905                 910

<210> SEQ ID NO 7
<211> LENGTH: 691
<212> TYPE: PRT
<213> ORGANISM: Mycobacterium tuberculosis
<220> FEATURE:
<221> NAME/KEY: MISC_FEATURE
<222> LOCATION: (1)..(296)
<223> OTHER INFORMATION: Ag85A mature protein sequence
<220> FEATURE:
<221> NAME/KEY: MISC_FEATURE
<222> LOCATION: (297)..(581)
<223> OTHER INFORMATION: Ag85B mature protein sequence
<220> FEATURE:
<221> NAME/KEY: MISC_FEATURE
<222> LOCATION: (582)..(676)
<223> OTHER INFORMATION: TB10.4 protein sequence
<220> FEATURE:
<221> NAME/KEY: MISC_FEATURE
<222> LOCATION: (677)..(691)
<223> OTHER INFORMATION: myc tag

<400> SEQUENCE: 7

Met Phe Ser Arg Pro Gly Leu Pro Val Glu Tyr Leu Gln Val Pro Ser
1               5                   10                  15

Pro Ser Met Gly Arg Asp Ile Lys Val Gln Phe Gln Ser Gly Gly Ala
            20                  25                  30

Asn Ser Pro Ala Leu Tyr Leu Leu Asp Gly Leu Arg Ala Gln Asp Asp
        35                  40                  45

Phe Ser Gly Trp Asp Ile Asn Thr Pro Ala Phe Glu Trp Tyr Asp Gln
50                  55                  60

Ser Gly Leu Ser Val Val Met Pro Val Gly Gly Gln Ser Ser Phe Tyr
65                  70                  75                  80

Ser Asp Trp Tyr Gln Pro Ala Cys Gly Lys Ala Gly Cys Gln Thr Tyr
                85                  90                  95

Lys Trp Glu Thr Phe Leu Thr Ser Glu Leu Pro Gly Trp Leu Gln Ala
            100                 105                 110

Asn Arg His Val Lys Pro Thr Gly Ser Ala Val Val Gly Leu Ser Met
        115                 120                 125

Ala Ala Ser Ser Ala Leu Thr Leu Ala Ile Tyr His Pro Gln Gln Phe
    130                 135                 140

Val Tyr Ala Gly Ala Met Ser Gly Leu Leu Asp Pro Ser Gln Ala Met
145                 150                 155                 160

Gly Pro Thr Leu Ile Gly Leu Ala Met Gly Asp Ala Gly Gly Tyr Lys
```

```
                    165                 170                 175
Ala Ser Asp Met Trp Gly Pro Lys Glu Asp Pro Ala Trp Gln Arg Asn
            180                 185                 190

Asp Pro Leu Leu Asn Val Gly Lys Leu Ile Ala Asn Thr Arg Val
        195                 200                 205

Trp Val Tyr Cys Gly Asn Gly Lys Pro Ser Asp Leu Gly Gly Asn Asn
        210                 215                 220

Leu Pro Ala Lys Phe Leu Glu Gly Phe Val Arg Thr Ser Asn Ile Lys
225                 230                 235                 240

Phe Gln Asp Ala Tyr Asn Ala Gly Gly His Asn Gly Val Phe Asp
                245                 250                 255

Phe Pro Asp Ser Gly Thr His Ser Trp Glu Tyr Trp Gly Ala Gln Leu
            260                 265                 270

Asn Ala Met Lys Pro Asp Leu Gln Arg Ala Leu Gly Ala Thr Pro Asn
                275                 280                 285

Thr Gly Pro Ala Pro Gln Gly Ala Phe Ser Arg Pro Gly Leu Pro Val
        290                 295                 300

Glu Tyr Leu Gln Val Pro Ser Pro Ser Met Gly Arg Asp Ile Lys Val
305                 310                 315                 320

Gln Phe Gln Ser Gly Gly Asn Asn Ser Pro Ala Val Tyr Leu Leu Asp
                325                 330                 335

Gly Leu Arg Ala Gln Asp Asp Tyr Asn Gly Trp Asp Ile Asn Thr Pro
            340                 345                 350

Ala Phe Glu Trp Tyr Tyr Gln Ser Gly Leu Ser Ile Val Met Pro Val
                355                 360                 365

Gly Gly Gln Ser Ser Phe Tyr Ser Asp Trp Tyr Ser Pro Ala Cys Gly
        370                 375                 380

Lys Ala Gly Cys Gln Thr Tyr Lys Trp Glu Thr Phe Leu Thr Ser Glu
385                 390                 395                 400

Leu Pro Gln Trp Leu Ser Ala Asn Arg Ala Val Lys Pro Thr Gly Ser
                405                 410                 415

Ala Ala Ile Gly Leu Ser Met Ala Gly Ser Ser Ala Met Ile Leu Ala
                420                 425                 430

Ala Tyr His Pro Gln Gln Phe Ile Tyr Ala Gly Ser Leu Ser Ala Leu
            435                 440                 445

Leu Asp Pro Ser Gln Gly Met Gly Pro Ser Leu Ile Gly Leu Ala Met
        450                 455                 460

Gly Asp Ala Gly Gly Tyr Lys Ala Ala Asp Met Trp Gly Pro Ser Ser
465                 470                 475                 480

Asp Pro Ala Trp Glu Arg Asn Asp Pro Thr Gln Gln Ile Pro Lys Leu
                485                 490                 495

Val Ala Asn Asn Thr Arg Leu Trp Val Tyr Cys Gly Asn Gly Thr Pro
                500                 505                 510

Asn Glu Leu Gly Gly Ala Asn Ile Pro Ala Glu Phe Leu Glu Asn Phe
            515                 520                 525

Val Arg Ser Ser Asn Leu Lys Phe Gln Asp Ala Tyr Asn Ala Ala Gly
        530                 535                 540

Gly His Asn Ala Val Phe Asn Phe Pro Pro Asn Gly Thr His Ser Trp
545                 550                 555                 560

Glu Tyr Trp Gly Ala Gln Leu Asn Ala Met Lys Gly Asp Leu Gln Ser
                565                 570                 575

Ser Leu Gly Ala Gly Met Ser Gln Ile Met Tyr Asn Tyr Pro Ala Met
            580                 585                 590
```

-continued

```
Leu Gly His Ala Gly Asp Met Ala Gly Tyr Ala Gly Thr Leu Gln Ser
            595                 600                 605

Leu Gly Ala Glu Ile Ala Val Glu Gln Ala Ala Leu Gln Ser Ala Trp
        610                 615                 620

Gln Gly Asp Thr Gly Ile Thr Tyr Gln Ala Trp Gln Ala Gln Trp Asn
625                 630                 635                 640

Gln Ala Met Glu Asp Leu Val Arg Ala Tyr His Ala Met Ser Ser Thr
                645                 650                 655

His Glu Ala Asn Thr Met Ala Met Met Ala Arg Asp Thr Ala Glu Ala
            660                 665                 670

Ala Lys Trp Gly Gly Ser Lys Lys Thr Glu Gln Lys Leu Ile Ser Glu
        675                 680                 685

Glu Asp Leu
    690

<210> SEQ ID NO 8
<211> LENGTH: 723
<212> TYPE: PRT
<213> ORGANISM: Mycobacterium tuberculosis
<220> FEATURE:
<221> NAME/KEY: MISC_FEATURE
<222> LOCATION: (1)..(296)
<223> OTHER INFORMATION: Ag85A mature protein sequence
<220> FEATURE:
<221> NAME/KEY: MISC_FEATURE
<222> LOCATION: (297)..(312)
<223> OTHER INFORMATION: linker sequence
<220> FEATURE:
<221> NAME/KEY: MISC_FEATURE
<222> LOCATION: (313)..(597)
<223> OTHER INFORMATION: Ag85B mature protein sequence
<220> FEATURE:
<221> NAME/KEY: MISC_FEATURE
<222> LOCATION: (598)..(613)
<223> OTHER INFORMATION: linker sequence
<220> FEATURE:
<221> NAME/KEY: MISC_FEATURE
<222> LOCATION: (614)..(709)
<223> OTHER INFORMATION: TB10.4 protein sequence
<220> FEATURE:
<221> NAME/KEY: MISC_FEATURE
<222> LOCATION: (710)..(723)
<223> OTHER INFORMATION: myc tag

<400> SEQUENCE: 8

Met Phe Ser Arg Pro Gly Leu Pro Val Glu Tyr Leu Gln Val Pro Ser
1               5                   10                  15

Pro Ser Met Gly Arg Asp Ile Lys Val Gln Phe Gln Ser Gly Gly Ala
            20                  25                  30

Asn Ser Pro Ala Leu Tyr Leu Leu Asp Gly Leu Arg Ala Gln Asp Asp
        35                  40                  45

Phe Ser Gly Trp Asp Ile Asn Thr Pro Ala Phe Glu Trp Tyr Asp Gln
    50                  55                  60

Ser Gly Leu Ser Val Val Met Pro Val Gly Gly Gln Ser Ser Phe Tyr
65                  70                  75                  80

Ser Asp Trp Tyr Gln Pro Ala Cys Gly Lys Ala Gly Cys Gln Thr Tyr
                85                  90                  95

Lys Trp Glu Thr Phe Leu Thr Ser Glu Leu Pro Gly Trp Leu Gln Ala
            100                 105                 110

Asn Arg His Val Lys Pro Thr Gly Ser Ala Val Val Gly Leu Ser Met
        115                 120                 125

Ala Ala Ser Ser Ala Leu Thr Leu Ala Ile Tyr His Pro Gln Gln Phe
    130                 135                 140
```

```
Val Tyr Ala Gly Ala Met Ser Gly Leu Leu Asp Pro Ser Gln Ala Met
145                 150                 155                 160

Gly Pro Thr Leu Ile Gly Leu Ala Met Gly Asp Ala Gly Gly Tyr Lys
                165                 170                 175

Ala Ser Asp Met Trp Gly Pro Lys Glu Asp Pro Ala Trp Gln Arg Asn
            180                 185                 190

Asp Pro Leu Leu Asn Val Gly Lys Leu Ile Ala Asn Thr Arg Val
        195                 200                 205

Trp Val Tyr Cys Gly Asn Gly Lys Pro Ser Asp Leu Gly Gly Asn Asn
    210                 215                 220

Leu Pro Ala Lys Phe Leu Glu Gly Phe Val Arg Thr Ser Asn Ile Lys
225                 230                 235                 240

Phe Gln Asp Ala Tyr Asn Ala Gly Gly His Asn Gly Val Phe Asp
                245                 250                 255

Phe Pro Asp Ser Gly Thr His Ser Trp Glu Tyr Trp Gly Ala Gln Leu
            260                 265                 270

Asn Ala Met Lys Pro Asp Leu Gln Arg Ala Leu Gly Ala Thr Pro Asn
        275                 280                 285

Thr Gly Pro Ala Pro Gln Gly Ala Gly Thr Gly Ser Gly Gly Thr
290                 295                 300

Gly Ser Gly Thr Gly Gly Ser Val Phe Ser Arg Pro Gly Leu Pro Val
305                 310                 315                 320

Glu Tyr Leu Gln Val Pro Ser Pro Ser Met Gly Arg Asp Ile Lys Val
                325                 330                 335

Gln Phe Gln Ser Gly Gly Asn Asn Ser Pro Ala Val Tyr Leu Leu Asp
                340                 345                 350

Gly Leu Arg Ala Gln Asp Asp Tyr Asn Gly Trp Asp Ile Asn Thr Pro
        355                 360                 365

Ala Phe Glu Trp Tyr Tyr Gln Ser Gly Leu Ser Ile Val Met Pro Val
        370                 375                 380

Gly Gly Gln Ser Ser Phe Tyr Ser Asp Trp Tyr Ser Pro Ala Cys Gly
385                 390                 395                 400

Lys Ala Gly Cys Gln Thr Tyr Lys Trp Glu Thr Phe Leu Thr Ser Glu
                405                 410                 415

Leu Pro Gln Trp Leu Ser Ala Asn Arg Ala Val Lys Pro Thr Gly Ser
            420                 425                 430

Ala Ala Ile Gly Leu Ser Met Ala Gly Ser Ser Ala Met Ile Leu Ala
            435                 440                 445

Ala Tyr His Pro Gln Gln Phe Ile Tyr Ala Gly Ser Leu Ser Ala Leu
        450                 455                 460

Leu Asp Pro Ser Gln Gly Met Gly Pro Ser Leu Ile Gly Leu Ala Met
465                 470                 475                 480

Gly Asp Ala Gly Gly Tyr Lys Ala Ala Asp Met Trp Gly Pro Ser Ser
            485                 490                 495

Asp Pro Ala Trp Glu Arg Asn Asp Pro Thr Gln Gln Ile Pro Lys Leu
            500                 505                 510

Val Ala Asn Asn Thr Arg Leu Trp Val Tyr Cys Gly Asn Gly Thr Pro
            515                 520                 525

Asn Glu Leu Gly Gly Ala Asn Ile Pro Ala Glu Phe Leu Glu Asn Phe
        530                 535                 540

Val Arg Ser Ser Asn Leu Lys Phe Gln Asp Ala Tyr Asn Ala Ala Gly
545                 550                 555                 560

Gly His Asn Ala Val Phe Asn Phe Pro Pro Asn Gly Thr His Ser Trp
            565                 570                 575
```

-continued

```
Glu Tyr Trp Gly Ala Gln Leu Asn Ala Met Lys Gly Asp Leu Gln Ser
            580                 585                 590

Ser Leu Gly Ala Gly Thr Gly Ser Gly Thr Gly Ser Gly
        595                 600                 605

Thr Gly Gly Ser Val Met Ser Gln Ile Met Tyr Asn Tyr Pro Ala Met
    610                 615                 620

Leu Gly His Ala Gly Asp Met Ala Gly Tyr Ala Gly Thr Leu Gln Ser
625                 630                 635                 640

Leu Gly Ala Glu Ile Ala Val Glu Gln Ala Ala Leu Gln Ser Ala Trp
            645                 650                 655

Gln Gly Asp Thr Gly Ile Thr Tyr Gln Ala Trp Gln Ala Gln Trp Asn
        660                 665                 670

Gln Ala Met Glu Asp Leu Val Arg Ala Tyr His Ala Met Ser Ser Thr
    675                 680                 685

His Glu Ala Asn Thr Met Ala Met Met Ala Arg Asp Thr Ala Glu Ala
    690                 695                 700

Ala Lys Trp Gly Gly Ser Lys Lys Thr Glu Gln Lys Leu Ile Ser Glu
705                 710                 715                 720

Glu Asp Leu

<210> SEQ ID NO 9
<211> LENGTH: 14
<212> TYPE: PRT
<213> ORGANISM: Artificial
<220> FEATURE:
<223> OTHER INFORMATION: Myc-epitope (myc-tag)

<400> SEQUENCE: 9

Ser Lys Lys Thr Glu Gln Lys Leu Ile Ser Glu Glu Asp Leu
1               5                   10

<210> SEQ ID NO 10
<211> LENGTH: 35
<212> TYPE: DNA
<213> ORGANISM: Artificial
<220> FEATURE:
<223> OTHER INFORMATION: Synthetic oligonucleotide ALVprot.FW

<400> SEQUENCE: 10
gcccaagctt gccaccatgc tggccatgac catgg                              35

<210> SEQ ID NO 11
<211> LENGTH: 32
<212> TYPE: DNA
<213> ORGANISM: Artificial
<220> FEATURE:
<223> OTHER INFORMATION: Syntehtic oligonucleotide 10.4.RE.stop

<400> SEQUENCE: 11
gctagtctag attatcagcc gccccacttg gc                                 32

<210> SEQ ID NO 12
<211> LENGTH: 25
<212> TYPE: DNA
<213> ORGANISM: Artificial
<220> FEATURE:
<223> OTHER INFORMATION: Synthetic oligonucleotide 85A.FW

<400> SEQUENCE: 12
gcccaagctt gccaccatgt tcagc                                         25
```

```
<210> SEQ ID NO 13
<211> LENGTH: 28
<212> TYPE: DNA
<213> ORGANISM: Artificial
<220> FEATURE:
<223> OTHER INFORMATION: Synthetic oligonucleottide 85B.RE myc

<400> SEQUENCE: 13
gcctagctag cgccggctcc caggctgc                                          28

<210> SEQ ID NO 14
<211> LENGTH: 37
<212> TYPE: DNA
<213> ORGANISM: Artificial
<220> FEATURE:
<223> OTHER INFORMATION: Synthetic oligonucleotide 85A.FW.TB.L

<400> SEQUENCE: 14
gcccaagctt gccaccatgt tcagcagacc cggcctg                                37

<210> SEQ ID NO 15
<211> LENGTH: 34
<212> TYPE: DNA
<213> ORGANISM: Artificial
<220> FEATURE:
<223> OTHER INFORMATION: Synthetic oligonucleotide 85B.RE.stop

<400> SEQUENCE: 15
gctagtctag attatcagcc ggctcccagg ctgc                                   34

<210> SEQ ID NO 16
<211> LENGTH: 22
<212> TYPE: DNA
<213> ORGANISM: Artificial
<220> FEATURE:
<223> OTHER INFORMATION: Synthetic oligonucleotide 85A.RE myc

<400> SEQUENCE: 16
gcctagctag cgccctgggg gg                                                22

<210> SEQ ID NO 17
<211> LENGTH: 37
<212> TYPE: DNA
<213> ORGANISM: Artificial
<220> FEATURE:
<223> OTHER INFORMATION: Synthetic oligonucleotide 85B.FW

<400> SEQUENCE: 17
gcccaagctt gccaccatgt tcagccggcc tggcctg                                37

<210> SEQ ID NO 18
<211> LENGTH: 42
<212> TYPE: DNA
<213> ORGANISM: Artificial
<220> FEATURE:
<223> OTHER INFORMATION: Synthetic oligonucleotide 10.4.FW

<400> SEQUENCE: 18
gcccaagctt gccaccatga gccagatcat gtacaactac cc                          42

<210> SEQ ID NO 19
<211> LENGTH: 30
<212> TYPE: DNA
<213> ORGANISM: Artificial
<220> FEATURE:
<223> OTHER INFORMATION: Synthetic oligonucleotide 10.4.RE myc

<400> SEQUENCE: 19
```

```
gctagtctag attatcacag gtcctcctcg                                         30
```

<210> SEQ ID NO 20
<211> LENGTH: 31
<212> TYPE: DNA
<213> ORGANISM: Artificial
<220> FEATURE:
<223> OTHER INFORMATION: Synthetic oligonucleotide 85A.RE.stop

<400> SEQUENCE: 20

```
gctagtctag attatcagcc ctgggggggca g                                      31
```

<210> SEQ ID NO 21
<211> LENGTH: 34
<212> TYPE: PRT
<213> ORGANISM: Artificial
<220> FEATURE:
<223> OTHER INFORMATION: Linker/digestion sequence for ALV protease

<400> SEQUENCE: 21

```
Pro Pro Ser Lys Ser Lys Lys Gly Gly Ala Ala Ala Met Ser Ser Ala
1               5                   10                  15

Ile Gln Pro Leu Val Met Ala Val Val Asn Arg Glu Arg Asp Gly Gln
            20                  25                  30

Thr Gly
```

<210> SEQ ID NO 22
<211> LENGTH: 28
<212> TYPE: PRT
<213> ORGANISM: Artificial
<220> FEATURE:
<223> OTHER INFORMATION: Avian leucosis protease cleavage site

<400> SEQUENCE: 22

```
Gly Ser Ser Gly Pro Trp Pro Ala Pro Glu Pro Pro Ala Val Ser Leu
1               5                   10                  15

Ala Met Thr Met Glu His Arg Asp Arg Pro Leu Val
            20                  25
```

<210> SEQ ID NO 23
<211> LENGTH: 16
<212> TYPE: PRT
<213> ORGANISM: Artificial
<220> FEATURE:
<223> OTHER INFORMATION: Flexible linker sequence

<400> SEQUENCE: 23

```
Gly Thr Gly Gly Ser Gly Gly Thr Gly Ser Gly Thr Gly Gly Ser Val
1               5                   10                  15
```

<210> SEQ ID NO 24
<211> LENGTH: 31
<212> TYPE: DNA
<213> ORGANISM: Artificial
<220> FEATURE:
<223> OTHER INFORMATION: Synthetic oligonucleotide forward primer for
      site-directed mutagenesis on plasmid pOGL1-A1

<400> SEQUENCE: 24

```
tgtttcccac caaaattagt ttgagaagtg c                                       31
```

<210> SEQ ID NO 25
<211> LENGTH: 30
<212> TYPE: DNA
<213> ORGANISM: Artificial

```
<220> FEATURE:
<223> OTHER INFORMATION: Synthetic oligonucleotide reverse primer for
      site-directed mutagenesis on plasmid pOGL1-A1.

<400> SEQUENCE: 25
caaactaatt ttggtggaaa catatccatc                                          30

<210> SEQ ID NO 26
<211> LENGTH: 15
<212> TYPE: PRT
<213> ORGANISM: Mycobacterium tuberculosis

<400> SEQUENCE: 26

Phe Ser Arg Pro Gly Leu Pro Val Glu Tyr Leu Gln Val Pro Ser
1               5                   10                  15

<210> SEQ ID NO 27
<211> LENGTH: 15
<212> TYPE: PRT
<213> ORGANISM: Mycobacterium tuberculosis

<400> SEQUENCE: 27

Gly Leu Pro Val Glu Tyr Leu Gln Val Pro Ser Pro Ser Met Gly
1               5                   10                  15

<210> SEQ ID NO 28
<211> LENGTH: 19
<212> TYPE: PRT
<213> ORGANISM: Mycobacterium tuberculosis

<400> SEQUENCE: 28

Phe Ser Arg Pro Gly Leu Pro Val Glu Tyr Leu Gln Val Pro Ser Pro
1               5                   10                  15

Ser Met Gly
```